United States Patent
Mansour et al.

(10) Patent No.: US 7,229,983 B2
(45) Date of Patent: Jun. 12, 2007

(54) 4-SUBSTITUTED OR UNSUBSTITUTED-7-HYDRO-1,4-THIAZEPINE-7-[BICYCLIC OR TRICYCLIC HETEROARYL] SUBSTITUTED-3,6-DICARBOXYLIC ACID DERIVATIVES AS β-LACTAMASE INHIBITORS

(75) Inventors: Tarek Suhayl Mansour, New City, NY (US); Aranapakam Mudumbai Venkatesan, Rego Park, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 170 days.

(21) Appl. No.: 10/834,301

(22) Filed: Apr. 28, 2004

(65) Prior Publication Data

US 2004/0214812 A1    Oct. 28, 2004

Related U.S. Application Data

(60) Provisional application No. 60/465,906, filed on Apr. 28, 2003.

(51) Int. Cl.
*A61P 31/04* (2006.01)
*A61K 31/55* (2006.01)
*C07D 281/10* (2006.01)

(52) U.S. Cl. ............................. 514/211.01; 514/211.15; 540/544

(58) Field of Classification Search ........... 514/211.01, 514/211.15; 540/544
See application file for complete search history.

(56) References Cited

FOREIGN PATENT DOCUMENTS

WO    WO 00/05246 A1    2/2000

OTHER PUBLICATIONS

Nigel J.P. Broom, et al., Studies of the Mechanism of Action (5*R*)-(Z)-6-(1-Methyl-1,2,3-triazol-4-ylmethylene)penem-3-carboxylic Acid (BRL 42715), a Potent Inhibitor of Bacterial β-Lactamase, *J. Chem. Soc.*, Chem. Communication, 1992, 1663-1664.
Giuseppina Visentin, et al., $\Delta^3$-Thiazolines $\Delta^4$-Thiazolines and Thiazoles from Penem Antibiotics, *Heterocycles*, vol. 33, No. 2, 859-891, 1992.
Keiko Tabei, et al., Mechanism of Inactivation of β-Lactamases by Novel 6-Methylidene Penems Elucidated Using Electrospray Ionization Mass Spectrometry, *J. Med. Chem.* 2004, 47, 3674-3688.
Michiyoshi Nukaga, et al., Inhibition of Class A and Class C β-Lactamases by Penems: Crystallographic Structures of a Novel 1,4-Thiazepine Intermediate, *Biochemistry* 2003, 42, 13152-13159.

*Primary Examiner*—Brenda Coleman
(74) *Attorney, Agent, or Firm*—John W. Hogan, Jr.

(57) ABSTRACT

The present invention relates to novel, low molecular weight broad spectrum compounds in particular to a class of 4-substituted or unsubstituted-7-hydro-1,4-thiazepine-7-[bicyclic or tricyclic heteroaryl] substituted-3,6-dicarboxylic acid or their derivatives which have β-lactamase inhibitory and antibacterial properties. The compounds are therefore useful in the treatment of antibacterial infections in humans or animals, either alone or in combination with other antibiotics.

21 Claims, No Drawings

4-SUBSTITUTED OR UNSUBSTITUTED-7-HYDRO-1,4-THIAZEPINE-7-[BICYCLIC OR TRICYCLIC HETEROARYL] SUBSTITUTED-3,6-DICARBOXYLIC ACID DERIVATIVES AS β-LACTAMASE INHIBITORS

This application claims priority from copending provisional application Ser. No. 60/465,906, filed Apr. 28, 2003, the entire disclosure of which is hereby incorporated by reference.

FIELD OF INVENTION

This invention relates to certain 4-substituted or unsubstituted-7-hydro-1,4-thiazepine-7-[bicyclic or tricyclic heteroaryl] substituted-3,6-dicarboxylic acid derivatives which act as a broad spectrum β-lactamase inhibitors. β-Lactamases hydrolyze β-lactam antibiotics, and as such serve as the primary cause of bacterial resistance. The compounds of the present invention when combined with β-lactam antibiotics will provide an effective treatment against life threatening bacterial infections.

BACKGROUND OF THE INVENTION

Penicillins and cephalosporins are the most frequently and widely used β-lactam antibiotics in the clinic. However, the development of resistance to β-lactam antibiotics by different pathogens has had a damaging effect on maintaining the effective treatment of bacterial infections. (Coleman, K. Expert *Opin. Invest. Drugs* 1995, 4, 693; Sutherland, R. *Infection* 1995, 23 (4) 191; Bush, K, *Cur. Pharm. Design* 1999, 5, 839–845) The most significant known mechanism related to the development of bacterial resistance to the β-lactam antibiotics is the production of class-A, class-B and class-C serine β-lactamases. These enzymes degrade the β-lactam antibiotics, resulting in the loss of antibacterial activity. Class-A enzymes preferentially hydrolyze penicillins where as Class-C lactamases have a substrate profile favoring cephalosporin hydrolysis. (Bush, K.; Jacoby, G. A.; Medeiros, A. A. *Antimicrob. Agents Chemother.* 1995, 39, 1211). To date over 250 different β-lactamases have been reported (Payne, D. J,: Du, W and Bateson, J. H. *Exp. Opin. Invest. Drugs* 2000, 247.) and there is a need for a new generation of broad spectrum β-lactamase inhibitors. Bacterial resistance to these antibiotics could be greatly reduced by administering the β-lactam antibiotic in combination with a compound which inhibits these enzymes.

The commercially available β-lactamase inhibitors such as clavulanic acid, sulbactam and tazobactam are all effective against class-A producing pathogens. Clavulanic acid is clinically used in combination with amoxicillin and ticarcillin; similarly sulbactam with ampicillin and tazobactam with piperacillin. However, these compounds are ineffective against class C producing organisms. The mechanism of inactivation of class-A β-lactamases (such as PCI and TEM-1) has been elucidated. (Bush, K.; *Antimicrob. Agents Chemother.* 1993, 37, 851; Yang, Y.; Janota, K.; Tabei, K.; Huang, N.; Seigal, M. M.; Lin, Y. I.; Rasmussen, B. A. and Shlaes, D. M. *J. Biol. Chem.* 2000, 35, 26674–26682).

In 1981, the Beecham group disclosed 6-alkylidine penems of general structure 1 as inhibitors of β-lactamases. [N. F. Osborne, U.S. Pat. No. 4,485,110 (1984); N. F. Osborne, Eur. Pat. Appl. 81 301683.9, 1981; N. F. Osborne, Eur. Pat. Appl. 84301255.0; N. F. Osborne, Eur. Pat. Appl. 85100520.7; Eur. Pat. Appl. 85100521.5; Eur. Pat. Appl. 85300456-2; N. J. P. Broom; F. P. Harrington, PCT WO 94/10178; K. Coleman; J. E. Neale PCT WO 95/28935; K. Coleman; J. E. Neale PCT WO 95/17184]

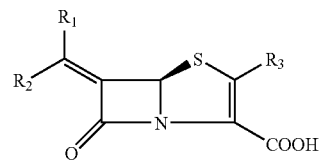

1

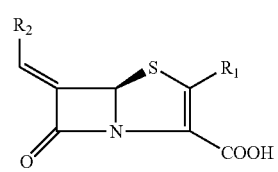

2

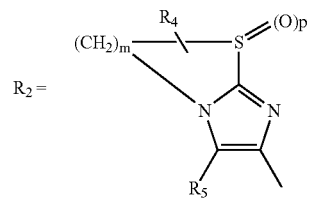

m = 2 or 3; p is 0, 1 or 2

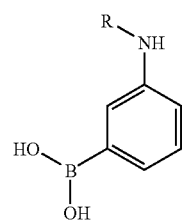

3

4

R=4-(Phenylsulfonyl)-thiophen-2-yl-sulfonyl 4-Carboxyphenylsulfamidophenyl-4yl-sulfonyl

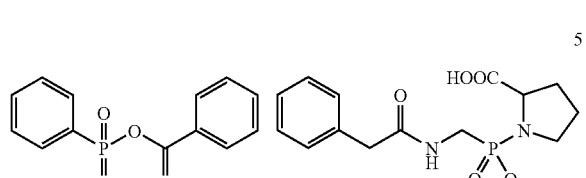

5

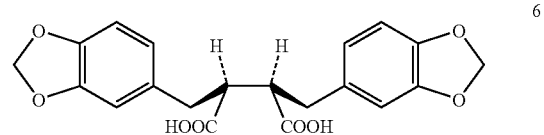

6

7

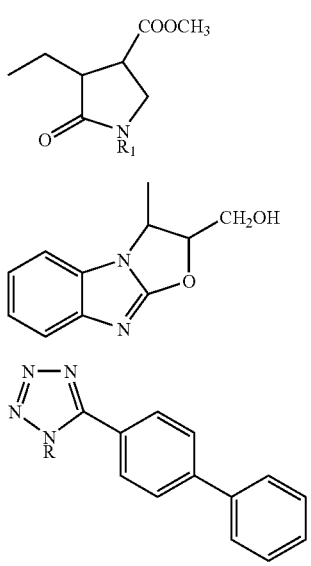

In addition to these methylidene based broad spectrum inhibitors, there were several transition state analogs based on boronic acids 3, 4 and acyl phosphanate 5 based inhibitors have been designed. [Martine, R.; Jones, J. B. *Tetrahedron Lett.* 1995, 36, 8399; Martine, R.; Gold, M.; Jones, J. B. *Bioorg. Med. Chem. Lett.* 1994, 4, 1229; Curley, K.; Pratt, R. F. *J. Am. Chem. Soc.* 1997, 119, 1529.; Rahil, J.; Pratt, R. F.; *Biochem. J.* 1991, 275, 793.; Rahil, J.; Pratt, R. F.; *Biochemistry* 1993, 32, 10763.]

The phosphonate based inhibitors were found to exclusively inhibit only the class C enzymes. In addition to these inhibitors several substituted succinic acid derivatives 6 were found to be potent inhibitors of metallo-β-lactamases. [Arakawa, Y.; Murakami, M.; Suzuki, K.; Ito, H.; Wacharotayankun, R.; Ohsuka, S.; Kato, N.; Ohta, M. *Antimicrob. Agents Chemother.*, 1996, 40, 349.] A number of compounds such as acrylonitrile derivatives 7, oxopyrrolidine carboxylate derivatives 8, 2H,3H-benzimidazo[2,1-b]oxazole derivatives 9 and biphenyl tetrazole are reported to have weak β-lactamase inhibitor activity. [For recent review ref. (a) Payne, D. J.; Du, W.; Bateson, J. H.; *Exp. Opin. Invest. Drugs* 2000, 9, 247: (b) Sandanayaka, V. P.; Prashad, A. S. *Current. Med. Chem.* 2002, 9,1145: (c) Micetich, R. G.; salama, S. M.; Maiti, S. N.; Reddy, A.V.N.; Singh, R. *Current. Med. Chem.* 2002, 1, 193.] How ever, to-date there is no known β-lactamase inhibitor having the molecular structure of 4,7-dihydro-1,4-thiazepine-7-[bicyclic or tricyclic heteroaryl] substituted-3,6-dicarboxylic acid or their derivatives. However 1,4-thiazepine derivatives have been prepared in the past by three groups. [(a) Broom, N. J .P.; Farmer, T. H.; Osborne, N. F.; Tyler, J. W. *J. Chem. Soc. Chem. Comm.* 1992,1663; (b) Visentin, G.; Perrone, E.; Borghi, D.; Rizzo, V.; Alpegiani, M.; Bedeschi, A.; Corigli, R.; Rivola, G.; Franceschi, G. *Heterocycles*, 1992, 33, 859; (c) Didier, B.; Pierre, D.; Dominique, L.; Eliane, M.; Antonio, U. PCT, WO 2000/005246.]

SUMMARY OF THE INVENTION

The present invention relates to novel, low molecular weight broad spectrum compounds in particular to a class of 4-substituted or unsubstituted-7-hydro-1,4-thiazepine-7-[bi- cyclic or tricyclic heteroaryl] substituted-3,6-dicarboxylic acid or their derivatives which have β-lactamase inhibitory and antibacterial properties. The compounds are therefore useful in the treatment of antibacterial infections in humans or animals, either alone or in combination with other antibiotics.

In accordance with the present invention there are provided compounds of general formula I or a pharmaceutically acceptable salt or in vivo hydrolyzable ester $R_5$ thereof:

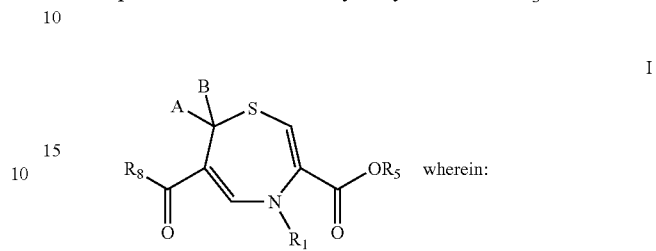

wherein:

One of A and B denotes hydrogen and the other an optionally substituted fused bicyclic or tricyclic heteroaryl group.

$R_1$ is H, optionally substituted —C1–C6 alkyl, optionally substituted -aryl, optionally substituted -heteroaryl or mono or bicyclic saturated heterocycles, optionally substituted —C3–C7 cycloalkyl, optionally substituted —C3–C6 alkenyl, optionally substituted —C3–C6 alkynyl with the proviso that both the double bond and the triple bond should not be present at the carbon atom which is directly linked to N; optionally substituted —C1–C6 per fluoro alkyl, —S(O)$_p$ optionally substituted alkyl or aryl where p is 2, optionally substituted —C═Oheteroaryl, optionally substituted —C═Oaryl, optionally substituted —C═O(C1–C6) alkyl, optionally substituted —C═O(C3–C6) cycloalkyl, optionally substituted —C═O mono or bicyclic saturated heterocycles, optionally substituted C1–C6 alkyl aryl, optionally substituted C1–C6 alkyl heteroaryl, optionally substituted aryl-C1–C6 alkyl, optionally substituted heteroaryl-C1–C6 alkyl, optionally substituted C1–C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1–C6alkyl aryloxyaryl, optionally substituted C1–C6 alkyl aryloxyheteroaryl, optionally substituted alkyl aryloxy alkylamines, optionally substituted alkoxy carbonyl, optionally substituted aryloxy carbonyl, optionally substituted heteroaryloxy carbonyl. Preferred $R_1$ groups are H, optionally substituted alkyl, optionally substituted aryl, —C═O(C1–C6)alkyl, C3–C6alkenyl, C3–C6alkynyl, optionally substituted cycloalkyl, SO$_2$alkyl, SO$_2$aryl, optionally substituted heterocycles, —CONR$_6$R$_7$, and optionally substituted heteroaryl.

$R_2$ is hydrogen, optionally substituted C1–C6 alkyl, optionally substituted C2–C6 alkenyl having 1 to 2 double bonds, optionally substituted C2–C6 alkynyl having 1 to 2 triple bonds, halogen, cyano, N—R$_6$R$_7$, optionally substituted C1–C6 alkoxy, hydroxy; optionally substituted aryl, optionally substituted heteroaryl, COOR$_6$, optionally substituted alkyl aryloxy alkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylene dioxy, optionally substituted aryloxy-C1–C6 alkyl amine, C1–C6 perfluoro alkyl, $S(O)_q$-optionally substituted C1–C6 akyl, $S(O)_q$—optionally substituted aryl where q is 0, 1 or 2, $CONR_6R_7$, guanidino or cyclic guanidino, optionally substituted C1–C6 alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, optionally substituted alkylaryloxyalkylamines, optionally substituted C3–C7 cycloalkyl, optionally substituted C3–C7 saturated or partially saturated heterocycle. Preferred $R_2$ groups are H, optionally substituted alkyl, optionally substituted alkoxy, optionally substituted heteroaryl, halogen, CN, hydroxy, optionally substituted heterocycle, —$CONR_6R_7$, $COOR_6$, optionally substituted aryl, $S(O)_q$-alkyl, and $S(O)_q$-aryl.

$R_3$ is hydrogen, C1–C6 alkyl, C3–C6 cycloalkyl, optionally substituted aryl, optionally substituted heteroaryl. Preferred $R_3$ groups are H or C1–C6 alkyl.

$R_4$ is H, optionally substituted C1–C6 alkyl, one of $R_4$ is OH, C1–C6 alkoxy, —S—C1–C6 alkyl, $COOR_6$, —$NR_6R_7$, —$CONR_6R_7$; or $R_4R_4$ may together be=O or $R_4R_4$ together with the carbon to which they are attached may form a spiro system of five to eight members with or without the presence of heteroatoms selected N, O, S=(O)n (where n=0 to 2), N—$R_1$; preferred $R_4$ groups are H, C1–C6 alkyl, $NR_6R_7$, or $R_4R_4$ together with the carbon to which they are attached forming a spiro system of five to eight members.

$R_5$ is H, an in vivo hydrolyzable ester such as C1–C6 alkyl, C5–C6 cycloalkyl, $CHR_3OCOC1$–C6 or salts such as Na, K, Ca; preferably $R_5$ is H or a salt;

$R_6$ and $R_7$ are independently H, optionally substituted C1–C6 alkyl, optionally substituted aryl, optionally substituted heteroaryl, optionally substituted C1–C6 alkyl aryl, optionally substituted arylalkyl, optionally substituted heteroarylalkyl, optionally substituted C1–C6 alkyl heteroaryl, $R_6$ and $R_7$ can be together to form a 3–7 membered saturated ring system optionally having one or two heteroatoms such as N—$R_1$, O, S=(O)$_n$ n=0–2. Preferred $R_6$ and $R_7$ groups are H, C1–C6 alkyl, arylalkyl, heteroarylalkyl or $R_6$ and $R_7$ together forming a 3–7 membered saturated ring system optionally having one or two heteroatoms.

$R_8$ is N—$R_6R_7$, optionally substituted C1–C6 alkoxy, hydroxy, optionally substituted —S—C1–C6 alkyl, optionally substituted —O-Aryl, optionally substituted —O—C1–C6-alkyl-aryl, optionally substituted —O-aryl alkyl(C1–C6), optionally substituted —S-Aryl, optionally substituted —S—C1–C6-alkyl-aryl, optionally substituted —S-aryl-alkyl(C1–C6), optionally substituted —O-Aryl-C1–C6-$NR_6R_7$, optionally substituted —S-Aryl-C1–C6-$NR_6R_7$, —S—optionally substituted C1–C6 alkyl-COO—H, —S—optionally substituted C1–C6 alkyl-COO—C1–C6 alkyl.

DETAILED DESCRIPTION OF THE INVENTION

In accordance with the present invention there are provided compounds of general formula I or a pharmaceutically acceptable salt or in vivo hydrolyzable ester $R_5$ thereof:

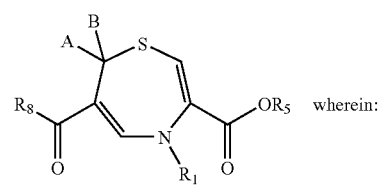

wherein:

One of A and B denotes hydrogen and the other an optionally substituted fused bicyclic heteroaryl group or an optionally substituted fused tricyclic heteroaryl group.

The expression "Fused tricyclic heteroaryl group" is used in the specification and claims to mean:

a group comprising three fused rings in which at least one ring has aromatic character (i.e meets Huckel's rule (4n+2)). The fused tricyclic heteroaryl group contains 1–6 heteroatoms selected from the group consisting of O, S, N and N—$R_1$. The fused tricyclic heteroaryl must be bonded through a carbon preferably in one of the at least one aromatic rings to the remainder of the formula I molecule. The fused tricyclic heteroaryl group may contain 1–3 aromatic rings and 0–2 non-aromatic rings. Each aromatic ring(s) in the fused tricyclic heteroaryl group may contain 5 to 7 ring atoms (including the bridgehead atoms) selected from $CR_2$, O, S, N, and N—$R_1$. Each of the aromatic ring(s) of the fused tricyclic heteroaryl group may contain 0 to 3 heteroatoms selected from O, S, N or N—$R_1$. The non-aromatic ring(s), if any, of the fused tricyclic heteroaryl group may contain 5–8 ring atoms (including bridgehead atoms) and contain 0–4 heteroatoms selected from N, N—$R_1$, O or $S(O)_n$, wherein n is 0–2. In each non-aromatic ring of the fused tricyclic heteroaryl group, one or two of the non-bridgehead carbon atoms may each be optionally substituted with one or two $R_4$, and each $R_4$ may be independently the same or different. Examples of fused tricyclic heteroaryl are optionally substituted ring systems such as imidazo[2,1-b][1,3]benzothiazole optionally substituted e.g., by for example C1–C6alkyl, C1–C6alkoxy or halo (such as chlorine or fluorine); imidazo[1,2-a]quinoline; 6,7-dihydro-5H-cyclopenta[d]imidazo[2,1-b][1,3]thiazole; imidazo[1,2-a]quinoxaline; 5,6,7,8-tetrahydro-[1,2,4]triazolo[1,5-a]pyridine dibenzo[b,f][1,4]-oxazepin-11(10H)-one optionally substituted e.g., by arylalkyl such as benzyl; 7,8-dihydro-6H-3,4,8b-triaza-as-indacene optionally substituted by C1–C6 alkoxy; 4H,10H-pyrazolo[5,1-c][1,4]benzoxazepine optionally substituted e.g., by C1–C6 alkoxy; 5H-Imidazo[2,1-a]isoindole; 5,8-dihydro-6H-imidazo[2,1-b]pyrano[4,3-d][1,3]thiazole; imidazo[2,1-b]benzothiazole; [1,3]thiazolo[3,2-a]benzimidazole; 7,8-dihydro-6H-cyclopenta[3,4]pyrazolo[5,1-b][1,3]thiazole; 5,6,7,8-tetrahydroimidazo[2,1-b][1,3]-benzothiazole; 9H-imidazo[1,2-a]benzimidazole optionally substituted e.g., by C1–C6alkyl; 4H-thieno[2',3':4,5]thiopyrano[2,3-b]pyridine; 7,8-dihydro-6H-cyclopenta[e][1,2,4]-triazolo[1,5-a]pyrimidine optionally substituted e.g., by C1–C6alkyl; 6,7,8,9-tetrahydropyrido[3,4-e][1,2,4]triazolo[1,5-a]pyrimidine optionally substituted e.g., by C2–C7alkoxycarbonyl; 8',9'-dihydro-6'H-spiro[1,3-dioxolane-2,7'-[1,2,4]triazolo[1,5-a]-quinazoline; 6,7,8,9-tetrahydro[1,2,4]triazolo[1,5-a]quinazoline optionally substituted e.g., by C1–C6alkyl; 7,8-dihydro-6H-cyclopenta[e]imidazo[1,2-a]pyrimidine optionally substituted e.g., by C1–C6alkoxy; 7,8-dihydro-6H-cyclopenta[e]imidazo[1,2-a]pyrimidinyl optionally substituted e.g., by arylalkyloxyalkyloxy; 3-dihydro[1,3]thiazolo[3,2-a]-benzimidazole; 2,3-dihydro[1,3]thiazolo[3,2-a]benzimidazole; 4-dihydro-2H-[1,3]thiazino[3,2-a]-benzimidazole; [1,3]thiazolo[3,2-a]benzimidazole; 7,8-dihydro-5H-pyrano[4,3-d]pyrazolo[5,1-b][1,3]-oxazole; 5,6,7,8-tetrahydropyrazolo[5,1-b][1,3]benzoxazole; and 5,6,7,8-tetrahydropyrazolo[5',1':2,3][1,3]oxazolo[5,4-c]pyridine optionally substituted e.g., by C2–C7alkoxycarbonyl.

Further examples of fused tricyclic heteroarylgroups are as follows:

Examples of fused tricyclic heteroarylgroup A and B:

Ring Size and Arrangements: (5-5-5)

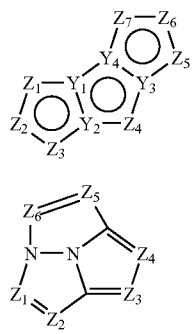

1-A

1-B

In both formula 1-A and 1-B $Z_1$, $Z_2$, $Z_3$, $Z_4$, $Z_5$, $Z_6$ and $Z_7$ are independently selected from $CR_2$, N, O, S or N—R, and as mentioned above one of $Z_{1-7}$ is a carbon atom to which the remainder of the molecule is attached. $Y_1$, $Y_2$, $Y_3$ and $Y_4$ may independently be C or N.

Ring Size and Arrangement: (5-5-6)

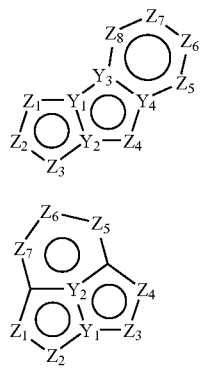

2-A

2-B

In both formula 2-A and 2-B $Z_1$, $Z_2$, $Z_3$, $Z_4$, $Z_5$, $Z_6$, $Z_7$ and $Z_8$ are independently selected from $CR_2$, N, O, S or N—$R_1$ and as mentioned above one of the $Z_1$–$Z_8$ is a carbon atom to which the remainder of the molecule is attached. $Y_1$, $Y_2$, $Y_3$ and $Y_4$ may be independently be C or N.

Ring Size and Arrangement: (5-6-5)

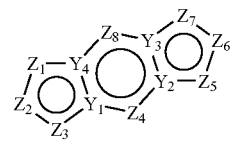

3-A

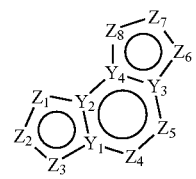

3-B

In both formula 3-A and 3-B $Z_1$, $Z_2$, $Z_3$, $Z_4$, $Z_5$, $Z_6$, $Z_7$ and $Z_8$ are independently selected from $CR_2$, N, O, S or N—$R_1$ and as mentioned above one of $Z_1$–$Z_8$ is a carbon atom to which the remainder of the molecule is attached. $Y_1$, $Y_2$, $Y_3$ and $Y_4$ may be C or N.

Ring Size and Arrangements: (5-6-6)

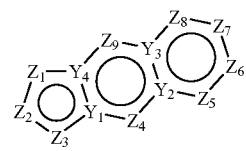

4-A

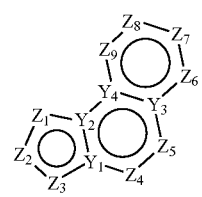

4-B

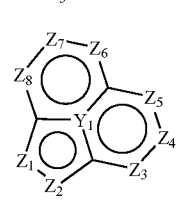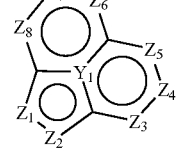

4-C

In formula 4-A, 4-B and 4-C $Z_1$, $Z_2$, $Z_3$, $Z_4$, $Z_5$, $Z_6$, $Z_7$ and $Z_8$ are independently selected from $CR_2$, N, O, S or N—$R_1$ and as mentioned above one of the $Z_1$–$Z_8$ is a carbon atom to which the remainder of the molecule is attached. $Y_1$, $Y_2$, $Y_3$ and $Y_4$ are independently C or N.

Ring Size and Arrangements: [5-5-(non-aromatic)]

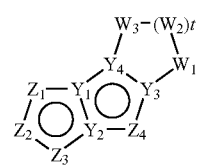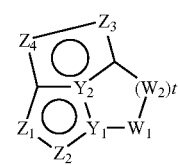

In both formula 5-A and 5-B $Z_1$, $Z_2$, $Z_3$ and 4 are indpendently selected from $CR_2$, N, O, S or N—$R_1$ and as mentioned above one of the $Z_1$–$Z_4$ is a carbon atom to which the remainder of the molecule is attached; $Y_1$, $Y_2$, $Y_3$ and $Y_4$ are independently C or N. $W_1$, $W_2$ and $W_3$ are independently selected from $CR_4R_4$, $S(O)r$ (r=0–2), O, N—$R_1$ with the proviso that no S—S, S—O or O—O bond formation can occur to form a saturated ring; and t=1 to 3.

Ring Size and Arrangement: [5-6-(non-aromatic)]

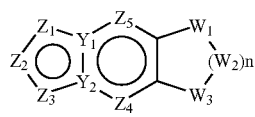

6-A

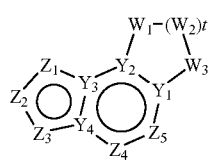

6-B

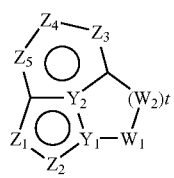

6-C

In formulae 6-A, 6-B and 6–C $Z_1$, $Z_2$, $Z_3$, $Z_4$ and $Z_5$ are indepedently selected from $CR_2$, N, O, S or N—$R_1$ and as mentioned above one of the $Z_1$–$Z_5$ is a carbon atom to which the remainder of the molecule is attached. $Y_1$, and $Y_2$ are independently C or N. $W_1$, $W_2$ and $W_3$ are independently $CR_4R_4$, $S(O)r$ (r=0–2), O, or N—$R_1$ with the proviso that no S—S, S—O or O—O bond formation can occur to form a saturated ring; and t=1 to 3.

Ring Size and Arrangement: [5-(non-aromatic)-5]

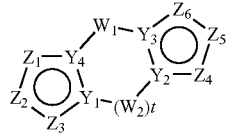

7-A

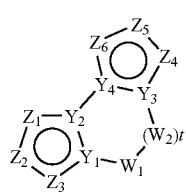

7-B

In formulae 7-A and 7-B $Z_1$, $Z_2$, $Z_3$, $Z_4$, $Z_5$ and $Z_6$ are independently selected from $CR_2$, N, O, S, and N—$R_1$; one of $Z_1$–$Z_6$ is a carbon atom to which the remainder of the molecule is attached. $Y_1$, $Y_2$, $Y_3$ and $Y_4$ are independently C or N. $W_1$ and $W_2$ are independently selected from $CR_4R_4$, $S(O)r$ (r=0–2), O, N—$R_1$ with the proviso that no S—S, S—O or O—O bond formation can occur to form a saturated ring; and t=1 to 3.

Ring Size and Arrangement: [5-(non-aromatic)-6]

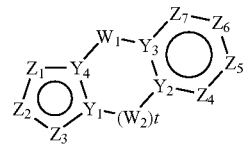

8-A

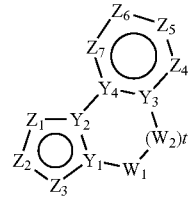

8-B

In formulae 8-A and 8-B $Z_1$, $Z_2$, $Z_3$, $Z_4$, $Z_5$, $Z_6$ and $Z_7$ are independently selected from $CR_2$, N, O, S and N—$R_1$ and as mentioned above one of the $Z_1$–$Z_7$ is a carbon atom to which the remainder of the molecule is attached. $Y_1$, $Y_2$, $Y_3$ and $Y_4$ are independently C or N. $W_1$ and $W_2$ are independently $CR_4R_4$, $S(O)r$ (r=0–2), O, or N—$R_1$ with the proviso that no S—S, S—O or O—O bond formation can occur to form a saturated ring; and t=0–3.

Ring Size and Arrangement [5-(non-aromatic)-(non-aromatic)]

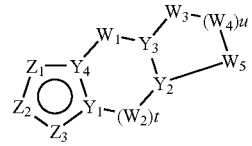

9-A

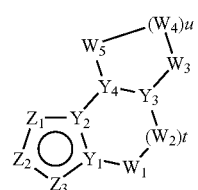

9-B

In formulae 9-A and 9-B $Z_1$, $Z_2$ and $Z_3$ are independently selected from $CR_2$ N, O, S or N—$R_1$; one of $Z_1$-$Z_3$ is a carbon atom to which the remainder of the molecule is attached. $Y_1$ and $Y_4$ are independently C or N; $Y_2$ and $Y_3$ are independently CH or N; $W_1$, $W_2$ $W_3$, $W_4$ and $W_5$ are independently $CR_4R_4$, $S(O)r$ (r=0–2), O, or N—$R_1$ with the proviso that no S—S, S—O or O—O bond formation can occur to form a saturated ring; t=0 to 2 and u=1 to 3.

Ring Size and Arrangement (6-5-6)

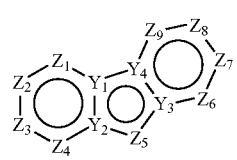

10-A

-continued

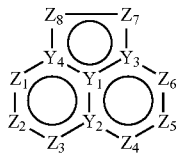

10-B

In formula 10-A and 10-B $Z_1$, $Z_2$, $Z_3$, $Z_4$, $Z_5$, $Z_6$, $Z_7$, $Z_8$ and $Z_9$ are independently selected from $CR_2$, N, O, S or N—$R_1$ and as mentioned above one of the $Z_1$–$Z_9$ is a carbon atom to which the remainder of the molecule is attached. $Y_1$, $Y_2$, $Y_3$ and $Y_4$ are independently C or N.

Ring Size and Arrangement (6-6-6)

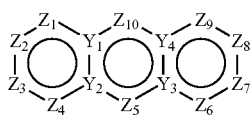

11-A

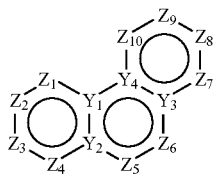

11-B

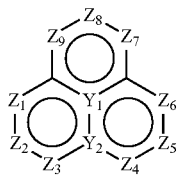

11-C

In formula 11-A, 11-B and 11-C $Z_1$, $Z_2$, $Z_3$, $Z_4$, $Z_5$, $Z_6$, $Z_7$, $Z_8$, $Z_9$ and $Z_{10}$ are independently $CR_2$, N, O, S or N—$R_1$; one of the $Z_1$–$Z_{10}$ is a carbon atom to which the remainder of the molecule is attached. $Y_1$, $Y_2$, $Y_3$ and $Y_4$ are independently C or N.

Ring Size and Arrangement [6-5-(non-aromatic)]

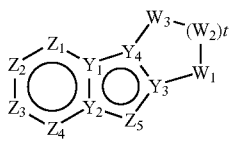

12-A

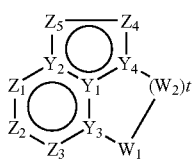

12-B

In formula 12-A and 12-B $Z_1$, $Z_2$, $Z_3$, $Z_4$ and $Z_5$ are independently $CR_2$, N, O, S or N—$R_1$ with the proviso that one of $Z_1$–$Z_5$ is a carbon atom to which the remainder of the molecule is attached. $Y_1$, $Y_2$, $Y_3$ and $Y_4$ are independently C or N; $W_1$, $W_2$, $W_3$ are independently $CR_4R_4$ O, N—$R_1$, or S=(O)$_r$ (r=0–2) with the proviso that no S—S, S—O or O—O bond formation can occur to form a saturated ring; and t=1–4.

Ring Size and Arrangement [6-6-(non-aromatic)]

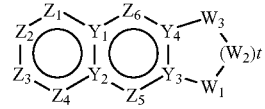

13-A

13-B

13-C

In formula 13-A, 13-B and 13-C $Z_1$, $Z_2$, $Z_3$, $Z_4$, $Z_5$ and $Z_6$ are independently $CR_2$, N, O, S or N—$R_1$; one of $Z_1$–$Z_6$ is a carbon atom to which the remainder of the molecule is attached. $Y_1$, $Y_2$, $Y_3$ and $Y_4$ are independently C or N; $W_1$, $W_2$ and $W_3$ are independently $CR_4R_4$, S(O)r (r=0–2), O, or N—$R_1$ with the proviso that no S—S, S—O or O—O bond formation can occur to form a saturated ring; and t=1 to 3.

Ring Size and Arrangement [6-(non-aromatic)-6]

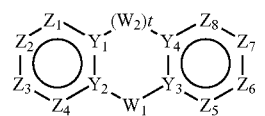

14-A

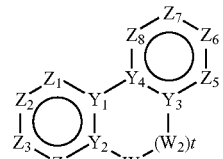

14-B

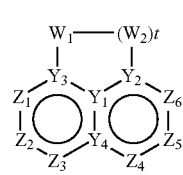

14-C

In formula 14-A, 14-B and 14-C $Z_1$, $Z_2$, $Z_3$, $Z_4$, $Z_5$, $Z_6$, $Z_7$ and $Z_8$ are independently $CR_2$, N, O, S or N—$R_1$; one of $Z_1$–$Z_8$ is a carbon atom to which the remainder of the molecule is attached. $Y_1$, $Y_2$, $Y_3$ and $Y_4$ are independently C or N; $W_1$, and $W_2$ are independently $CR_4R_4$, S(O)r (r=0–2), O, or N—$R_1$ with the proviso that no S—S, S—O or O—O bond formation can occur to form a saturated ring; and t=1 to 2.

Ring Size and Arrangement [6-(non-aromatic)-(non-aromatic)]

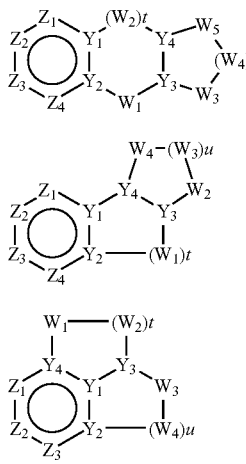

15-A

15-B

15-C

In formula 15-A, 15-B and 15-C $Z_1$, $Z_2$, $Z_3$ and $Z_4$ are independently $CR_2$, N, O, S or $N-R_1$; one of $Z_1-Z_4$ is a carbon atom to which the remainder of the molecule is attached. $Y_1$, $Y_2$, $Y_3$ and $Y_4$ are independently C or N; $W_1$, $W_2$, $W_3$, $W_4$ and $W_5$ are independently $CR_4R_4$, $S(O)r$ (r=0–2), O, or $N-R_1$ with the proviso that no S—S, S—O or O—O bond formation can occur to form a saturated ring; t=1 to 3 and u=1 to 3.

The preferred embodiments of formula 1-A are:

1. $Z_1$ is O, S, or $N-R_1$; $Z_2$, $Z_3$, $Z_4$, $Z_5$, $Z_6$ and $Z_7$ are independently $CR_2$, or N; $Y_1$, $Y_2$, $Y_3$, $Y_4$ are C; any one of $Z_2$, $Z_3$, $Z_4$, $Z_5$, $Z_6$, $Z_7$ is a carbon to which the remainder of the molecule is attached.
2. $Z_1$ is O, S, or $N-R_1$; $Z_2$, $Z_3$, $Z_4$, $Z_5$, $Z_6$ and $Z_7$ are independently $CR_2$; $Y_1$, $Y_2$, $Y_3$, and $Y_4$ are C; one of $Z_2$, $Z_3$, $Z_4$, $Z_5$, $Z_6$, $Z_7$ is a carbon to which the remainder of the molecule is attached.
3. $Z_2$ is O, S, or $N-R_1$; $Z_1$, $Z_3$, $Z_4$, $Z_5$, $Z_6$ and $Z_7$ are independently $CR_2$, or N ; $Y_1$, $Y_2$, $Y_3$, $Y_4$ are C; one of $Z_1$, $Z_3$, $Z_4$, $Z_5$, $Z_6$, $Z_7$ is a carbon to which the remainder of the molecule is attached.
4. $Z_2$ is O, S, or $N-R_1$; $Z_1$, $Z_3$, $Z_4$, $Z_5$, $Z_6$ and $Z_7$ are independently $CR_2$ ; $Y_1$, $Y_2$, $Y_3$, $Y_4$ are C; one of $Z_1$, $Z_3$, $Z_4$, $Z_5$, $Z_6$, $Z_7$ is a carbon to which the remainder of the molecule is attached.
5. $Z_3$ is O, S, or $N-R_1$; $Z_1$, $Z_2$, $Z_4$, $Z_5$, $Z_6$, $Z_7$ are independently $CR_2$, or N ; $Y_1$,$Y_2$, $Y_3$, $Y_4$ are C; one of $Z_1$, $Z_2$, $Z_4$, $Z_5$, $Z_6$, $Z_7$ is a carbon to which the remainder of the molecule is attached.
6. $Z_3$ is O, S, or $N-R_1$; $Z_1$, $Z_2$, $Z_4$, $Z_5$, $Z_6$, $Z_7$ are independently $CR_2$ ; $Y_1$,$Y_2$,$y_3$,$y_4$ are C; one of $Z_1$, $Z_3$, $Z_4$, $Z_5$, $Z_6$, or $Z_7$ is a carbon to which the remainder of the molecule is attached.
7. $Z_7$ is O, S, or $N-R_1$; $Z_1$, $Z_2$, $Z_3$, $Z_4$, $Z_5$ and $Z_6$ are independently $CR_2$ or N; $Y_1$, $Y_2$, $Y_3$, $Y_4$ are C; one of $Z_1$, $Z_2$, $Z_3$, $Z_4$, $Z_5$ and $Z_6$ is a carbon to which the remainder of the molecule is attached.
8. $Z_7$ is O, S, or $N-R_1$; $Z_1$, $Z_2$, $Z_3$, $Z_4$, $Z_5$ and $Z_6$ are independently $CR_2$ ; $y_1$, $Y_3$, $Y_3$, $Y_4$ are C; any of $Z_1$, $Z_2$, $Z_3$, $Z_4$, $Z_5$ and $Z_6$ is a carbon to which the remainder of the molecule is attached.
9. $Z_1$, $Z_4$, and $Z_6$ are independently O, S, or N—R; $Z_2$, $Z_3$, $Z_5$, $Z_7$ are independently $CR_2$, or N; $Y_1$, $Y_2$, $Y_3$, $Y_4$ are C; any one of $Z_2$, $Z_3$, $Z_5$, or $Z_7$ is a carbon to which the remainder of the molecule is attached.
10. $Z_1$, $Z_4$, and $Z_6$ are independently O, S, or $N-R_1$; $Z_2$, $Z_3$, $Z_5$, $Z_7$ are independently $CR_2$; $Y_1$, $Y_2$, $Y_3$, $Y_4$ are C; any one of $Z_2$, $Z_3$, $Z_5$, or $Z_7$ is a carbon to which the remainder of the molecule is attached.
11. $Z_3$, $Z_4$, and $Z_6$ are independently O, S, or $N-R_1$; $Z_1$, $Z_2$, $Z_5$, $Z_7$ are independently $CR_2$, or N; $Y_1$, $Y_2$, $Y_3$, $Y_4$ are C; any one of $Z_1$, $Z_2$, $Z_5$, or $Z_7$ is a carbon to which the remainder of the molecule is attached.
12. $Z_3$, $Z_4$, and $Z_6$ are independently O, S, or $N-R_1$; $Z_2$, $Z_3$, $Z_5$, $Z_7$ are independently $CR_2$; $Y_1$, $Y_2$, $Y_3$, $Y_4$ are C; any one of $Z_1$, $Z_2$, $Z_5$, or $Z_7$ is a carbon to which the remainder of the molecule is attached.
13. $Z_1$ is O, S, or $N-R_1$; $Z_2$, $Z_3$, $Z_4$, $Z_5$, $Z_6$ and $Z_7$ are independently $CR_2$, or N ; $Y_2$ is N; $Y_1$, $Y_3$, $Y_4$ are C; any one of $Z_2$, $Z_3$, $Z_4$, $Z_5$, $Z_6$, or $Z_7$ is a carbon to which the remainder of the molecule is attached.
14. $Z_1$ is O, S, or $N-R_1$; $Z_2$, $Z_3$, $Z_4$, $Z_5$, $Z_6$ and $Z_7$ are independently $CR_2$ ; $Y_2$ is N; $Y_1$, $Y_3$, $Y_4$ are C; one of $Z_2$, $Z_3$, $Z_4$, $Z_5$, $Z_6$, or $Z_7$ is a carbon to which the remainder of the molecule is attached.
15. $Z_2$ and $Z_4$ are independently O, S, or $N-R_1$; $Z_1$, $Z_3$, $Z_5$, $Z_6$, $Z_7$ are independently $CR_2$, N; $Y_1$ is N; $Y_2$, $Y_3$, $Y_4$ are C; any one of $Z_1$, $Z_3$, $Z_5$, $Z_6$, or $Z_7$ is a carbon to which the remainder of the molecule is attached.
16. $Z_2$ and $Z_4$ are independently O, S, or $N-R_1$; $Z_1$, $Z_3$, $Z_5$, $Z_6$, $Z_7$ are independently $CR_2$; $Y_1$ is N; $Y_2$, $Y_3$, $Y_4$ are C; any one of $Z_1$, $Z_3$, $Z_5$, $Z_6$, or $Z_7$ is a carbon to which the remainder of the molecule is attached
17. $Z_3$ and $Z_5$ are independently O, S, or $N-R_1$; $Z_1$, $Z_2$, $Z_4$, $Z_6$, $Z_7$ are independently $CR_2$, or N; $Y_1$ is N; $Y_2$, $Y_3$, $Y_4$ are C; any one of $Z_1$, $Z_3$, $Z_5$, $Z_6$, or $Z_7$ is a carbon to which the remainder of the molecule is attached.
18. $Z_3$ and $Z_5$ are independently O, S, or $N-R_1$; $Z_1$, $Z_2$, $Z_4$, $Z_6$, $Z_7$ are independently $CR_2$; $Y_1$ is N; $Y_2$, $Y_3$, $Y_4$ are C; any one of $Z_1$, $Z_3$, $Z_5$, $Z_6$, or $Z_7$ is a carbon to which the remainder of the molecule is attached.
19. $Z_1$ and $Z_5$ are independently O, S, or $N-R_1$; $Z_2$, $Z_3$, $Z_4$, $Z_6$, $Z_7$ are independently N, or $CR_2$ ; $Y_1$ is N; $Y_2$, $Y_3$, $Y_4$ are C; any one of $Z_2$, $Z_3$, $Z_4$, $Z_6$, $Z_7$ is a carbon to which the remainder of the molecule is attached.
20. $Z_1$ and $Z_5$ are independently O, S, or $N-R_1$; $Z_2$, $Z_3$, $Z_4$, $Z_6$, $Z_7$ are independently $CR_2$ ; $Y_1$ is N; $Y_2$, $Y_3$, $Y_4$ are C; any one of $Z_2$, $Z_3$, $Z_4$, $Z_6$, or $Z_7$ is a carbon to which the remainder of the molecule is attached.
21. $Z_3$ and $Z_7$ are independently O, S, or $N-R_1$; $Z_1$, $Z_2$, $Z_4$, $Z_5$, $Z_6$ are independently N, or $CR_2$ ; $Y_1$ is N; $Y_2$, $Y_3$, $Y_4$ are C; any one of $Z_1$, $Z_2$, $Z_4$, $Z_5$, or $Z_6$ is a carbon to which the remainder of the molecule is attached.
22. $Z_3$ and $Z_7$ are independently O, S, $N-R_1$; $Z_1$, $Z_2$, $Z_4$, $Z_5$, $Z_6$ are independently $CR_2$; $Y_1$ is N; $Y_2$, $Y_3$, $Y_4$ are C; Any one of $Z_1$, $Z_2$, $Z_4$, $Z_5$, or $Z_6$ is a carbon to which the remainder of the molecule is attached.
23. $Z_3$ and $Z_7$ are independently O, S, $N-R_1$; $Z_1$, $Z_2$, $Z_4$, $Z_5$, $Z_6$ are independently N, or $CR_2$; $Y_2$ is N; $Y_1$, $Y_3$, $Y_4$ are C; any one of $Z_1$, $Z_2$, $Z_4$, $Z_5$, or $Z_6$ is a carbon to which the remainder of the molecule is attached.
24. $Z_3$ and $Z_7$ are independently O, S, or $N-R_1$; $Z_1$, $Z_2$, $Z_4$, $Z_5$, $Z_6$ are independently $CR_2$; $Y_2$ is N; $Y_1$, $Y_3$, $Y_4$ are C; any one of $Z_1$, $Z_2$, $Z_4$, $Z_5$, or $Z_6$ is a carbon to which the remainder of the molecule is attached.
25. $Z_3$ and $Z_5$ are independently O, S, $N-R_1$; $Z_1$, $Z_2$, $Z_4$, $Z_6$, $Z_7$ are independently N, or $CR_2$; $Y_2$ is N; $Y_1$, $Y_3$, $Y_4$ are C; any one of $Z_1$, $Z_2$, $Z_4$, $Z_6$, or $Z_7$ is a carbon to which the remainder of the molecule is attached.

26. $Z_3$ and $Z_5$ are independently O, S, or N—$R_1$; $Z_1$, $Z_2$, $Z_4$, $Z_6$, $Z_7$ are independently $CR_2$; $Y_2$ is N; $Y_1$, $Y_3$, $Y_4$ are C; any one of $Z_1$, $Z_2$, $Z_4$, $Z_6$, or $Z_7$ is a carbon to which the remainder of the molecule is attached.

The preferred embodiment of formula 1-B is:

27. $Z_1$, $Z_2$, $Z_3$, $Z_4$, $Z_5$, $Z_6$ and $Z_7$ are independently $CR_2$.

The preferred embodiments of formula 2-A are:

28. $Z_1$ is $CR_2$; $Z_2$ is the carbon to which the remainder of the molecule is attached; $Z_3$ is N or $CR_2$; $Z_4$ is O, S, $CR_2$ or N—$R_1$; $Z_5$, $Z_6$, $Z_7$, $Z_8$ are independently $CR_2$ or N; $Y_1$ is N; $Y_2$, $Y_3$ and $Y_4$ are C.

29. $Z_2$ is $CR_2$; $Z_1$ is carbon to which the remainder of the molecule is attached; $Z_3$ is N or $CR_2$; $Z_4$ is O, S, $CR_2$ or N—$R_1$; $Z_5$, $Z_6$, $Z_7$, $Z_8$ are independently $CR_2$ or N; $Y_1$ is N; $Y_2$, $Y_3$ and $Y_4$ are C.

30. $Z_1$ is N, $Z_2$ is carbon to which the remainder of the molecule is attached; $Z_3$ is N or $CR_2$; $Z_4$ O, S, $CR_2$ or N—$R_1$; $Z_5$, $Z_6$, $Z_7$, $Z_8$ are independently $CR_2$ or N; $Y_1$ is N; $Y_2$, $Y_3$ and $Y_4$ are C.

31. $Z_1$, $Z_2$, $Z_3$ are independently $CR_2$ or N; $Z_4$ is O, S, $CR_2$ or N—$R_1$; $Z_5$, $Z_6$, $Z_7$, $Z_8$ are independently $CR_2$ or N and one of $Z_5$, $Z_6$, $Z_7$, or $Z_8$ is a carbon to which the remainder of the molecule is attached; $Y_1$ is N; $Y_2$, $Y_3$ and $Y_4$ is C.

32. $Z_1$ is $CR_2$ or N; $Z_2$ is $CR_2$: $Z_3$ is O, S or N—$R_1$; $Z_4$ is N or $CR_2$; $Z_5$, $Z_6$, $Z_7$, $Z_8$ are independently $CR_2$; $Y_1$ is N, or C; $Y_2$, $Y_3$ and $Y_4$ are C.

33. $Z_1$, $Z_2$, $Z_3$, $Z_4$, $Z_5$, $Z_6$, $Z_7$, $Z_8$ are independently N or $CR_2$; $Y_1$, $Y_2$, $Y_3$, $Y_4$ are C.

34. $Z_1$, $Z_2$, $Z_5$, $Z_6$, $Z_7$, $Z_8$ are independently N or $CR_2$; $Z_3$ and $Z_4$ are independently O, S, or N—$R_1$; $Y_1$, $Y_2$, $Y_3$, and $Y_4$ are C.

35. $Z_1$, $Z_2$, and $Z_3$ are independently $CR_2$ or N; $Z_4$ is O, S, $CR_2$ or N—$R_1$; $Z_5$, $Z_6$, $Z_7$, and $Z_8$ are independently $CR_2$ or N; $Y_1$ is N; $Y_2$, $Y_3$ and $Y_4$ are C.

36. $Z_1$ is N; $Z_2$ is $CR_2$; $Z_3$ is the carbon atom to which remainder of the molecule is attached; $Z_4$ is N; $Z_5$, $Z_6$, $Z_7$, $Z_8$ are independently N or $CR_2$; $Y_1$, $Y_2$, $Y_3$, $Y_4$ are independently N or C.

The preferred embodiment of formula 2-B is:

37. $Z_1$ and $Z_4$ are independently $CR_2$ or N; $Z_2$ and $Z_3$ are $CR_2$; $Z_5$, $Z_6$, $Z_7$ are independently $CR_2$ or N; $Y_1$ is C and $Y_2$ is N.

38. $Z_1$ is O, S, or N—$R_1$; $Z_2$ is $CR_2$; $Z_3$ is $CR_2$, or N; $Z_4$ is O, S, N—$R_1$, or $CR_2$: $Z_5$, $Z_6$, $Z_7$, $Z_8$ are independently N or $CR_2$; $Y_1$, $Y_2$, $Y_3$, and $Y_4$ are C; one of $Z_2$, $Z_3$, $Z_5$, $Z_6$, $Z_7$, or $Z_8$ is a carbon atom to which the remainder of the molecule is attached.

The preferred embodiments of formula 3-A are:

39. $Z_1$ is O, S, or N—$R_1$; $Z_2$ is N, or $CR_2$; $Z_3$ is $CR_2$; $Z_5$, $Z_6$, and $Z_7$ are independently N or $CR_2$; $Z_4$ and $Z_8$ are independently O, S, or N—$R_1$; $Y_1$, $Y_2$, $Y_3$, and $Y_4$ are C and one of $Z_2$, $Z_5$, $Z_6$, or $Z_7$ is a carbon atom to which the remainder of the molecule is attached.

40. $Z_3$ is O, S, or N—$R_1$; $Z_2$ is N, $CR_2$; $Z_1$ is $CR_2$; $Z_5$, $Z_6$, and $Z_7$ are independently N or $CR_2$; $Z_4$ and $Z_8$ are independently O, S, or N—$R_1$; $Y_1$, $Y_2$, $Y_3$, and $Y_4$ are C and one of $Z_2$, $Z_5$, $Z_6$, or $Z_7$ is a carbon atom to which the remainder of the molecule is attached.

The preferred embodiments of formula 3-B are:

41. $Z_1$ is O, S, or N—$R_1$; $Z_2$ is N or $CR_2$; $Z_3$ is $CR_2$; $Z_4$, $Z_5$, $Z_6$, $Z_7$ and $Z_8$ are independently N or $CR_2$; $Y_1$, $Y_2$, $Y_3$, and $Y_4$ are C; and one of $Z_2$, $Z_5$, $Z_6$, $Z_7$ is a carbon atom to which the remainder of the molecule is attached.

42. $Z_1$ is N or $CR_2$; $Z_2$ is $CR_2$; $Z_3$ is O, S, N—$R_1$ or $CR_2$; $Z_7$ is $CR_2$ or N; $Z_6$, and $Z_8$ are independently N or $CR_2$; $Z_4$ and $Z_5$ are $CR_2$ or N; $Y_1$, $Y_2$, and $Y_3$ are C; $Y_4$ is N and one of $Z_2$, $Z_4$, $Z_5$, $Z_6$ is a carbon atom to which the remainder of the molecule is attached.

43. $Z_1$ is N, or $CR_2$; $Z_2$ is $CR_2$; $Z_3$ is O, S, N—$R_1$ or $CR_2$; $Z_6$ is $CR_2$ or N; $Z_7$, and $Z_8$ are independently N or $CR_2$; $Z_4$ and $Z_5$ are independently $CR_2$ or N; $Y_1$, $Y_2$, $Y_3$ are C; $Y_4$ is N and one of $Z_2$, $Z_4$, $Z_5$, $Z_6$ is a carbon atom to which the remainder of the molecule is attached.

44. $Z_1$ is O, S, or N—$R_1$; $Z_2$ is N, or $CR_2$; $Z_3$ is $CR_2$; $Z_6$, $Z_7$, and $Z_8$ are N; $Z_4$ and $Z_5$ are independently $CR_2$ or N; $Y_1$, $Y_2$, $Y_4$ are C; $Y_3$ is N and one of $Z_2$, or $Z_3$ is a carbon atom to which the remainder of the molecule is attached.

45. $Z_1$ is N or $CR_2$; $Z_2$ is $CR_2$; $Z_3$ is O, S, N—$R_1$ or $CR_2$; $Z_6$, $Z_7$, and $Z_8$ and N; $Z_4$, and $Z_5$ are independently $CR_2$ or N; $Y_1$, $Y_2$, $Y_4$ are C; $Y_3$ is N and one of $Z_1$, $Z_2$ is a carbon atom to which the remainder of the molecule is attached.

46. $Z_1$ is N or $CR_2$; $Z_2$ is $CR_2$; $Z_3$ is O, S, N—$R_1$ or $CR_2$; $Z_6$, $Z_7$, and $Z_8$ are N; $Z_4$ and $Z_5$ are independently $CR_2$ or N; $Y_1$, $Y_2$, $Y_4$ are C; $Y_3$ is N and one of $Z_1$, $Z_2$, is a carbon atom to which the remainder of the molecule is attached.

47. $Z_1$ is N; $Z_2$, $Z_3$, $Z_4$ and $Z_5$ are independently $CR_2$; $Z_6$, $Z_7$, and $Z_8$ are independently O, S, N, N—$R_1$ or $CR_2$; $Y_2$, $Y_3$, and $Y_4$ are C; $Y_1$ is N; one of $Z_2$, $Z_3$, $Z_6$, $Z_6$, $Z_7$, $Z_8$ is a carbon atom to which the remainder of the molecule is attached.

48. $Z_3$ is N; $Z_2$ and $Z_1$ are independently $CR_2$; $Z_4$, and $Z_5$ are independently $CR_2$; $Z_6$, $Z_7$, $Z_8$ are independently O, S, N, N—$R_1$ or $CR_2$; $Y_2$, $Y_3$, and $Y_1$ are C; $Y_4$ is N; one of $Z_2$, $Z_1$, $Z_6$, $Z_6$, $Z_7$, $Z_8$ is a carbon atom to which the remainder of the molecule is attached.

49. $Z_1$ is N, or $CR_2$; $Z_2$ is $CR_2$; $Z_3$ is O, S, or N—$R_1$; $Z_4$ and $Z_5$ are independently $CR_2$; $Z_6$, $Z_7$, $Z_8$ are independently O, S, N, N—$R_1$, or $CR_2$; $Y_1$, $Y_2$, $Y_3$, and $Y_4$ are C; one of $Z_1$, $Z_2$, $Z_3$, $Z_6$, $Z_7$, $Z_8$ is a carbon atom to which the remainder of the molecule is attached.

The Preferred embodiments of formula 4-A

50. $Z_1$ and $Z_3$ are independently O, S, N—$R_1$, N, or $CR_2$; $Z_2$ is $CR_2$; $Z_4$, $Z_5$, $Z_6$, $Z_7$, $Z_8$, $Z_9$, are independently $CR_2$; $Y_1$, $Y_2$, $Y_3$, $Y_4$, are C.

51. $Z_1$ and $Z_3$ are independently O, S, N—$R_1$, N, or $CR_2$; $Z_2$ is $CR_2$; $Z_4$, and $Z_9$ are independently $CR_2$, or N; $Z_5$, $Z_6$, $Z_7$, $Z_8$ are independently $CR_2$; $Y_1$, $Y_2$, $Y_3$, $Y_4$, are C; One of $Z_1$, $Z_2$, $Z_3$, $Z_5$, $Z_6$, $Z_7$, $Z_8$ is a carbon atom to which the remainder of the molecule is attached.

52. $Z_1$ is S, O, or N—$R_1$; $Z_2$, $Z_3$, $Z_4$, $Z_5$, $Z_6$, $Z_7$, $Z_8$ are independent $Cr_2$; $Z_9$ is N; $Y_1$, $Y_2$, $Y_3$, $Y_4$, are C.

53. $Z_1$, and $Z_3$ are independently O, S, N—$R_1$, N, or $CR_2$; $Z_4$, and $Z_9$ are independently N or $CR_2$; $Z_5$, $Z_6$, $Z_7$, $Z_8$ are independently $CR_2$ or N; $Y_1$, $Y_2$, $Y_3$, $Y_4$, are C; $Z_2$ is the carbon to which the remainder of the molecule is attached.

54. $Z_1$ is N; $Z_2$, $Z_3$, and $Z_4$ are independently $CR_2$; $Z_5$, $Z_6$, $Z_7$, $Z_8$ are independently N or $CR_2$; $Z_9$ is $CR_2$ or N; $Y_1$ is N; $Y_2$, $Y_3$, and $Y_4$, are C; $Z_2$ or $Z_3$ is the carbon to which the remainder of the molecule is attached.

55. $Z_3$ is N; $Z_1$, $Z_2$, and $Z_4$ are independently $CR_2$; $Z_5$, $Z_6$, $Z_7$, and $Z_8$ are independently $CR_2$, or N; $Z_9$ is $CR_2$, or N; $Y_4$ is N; $Y_1$, $Y_2$, and $Y_3$ are C.

The Preferred embodiments of formula 4-B

56. $Z_1$ is N; $Z_2$, $Z_3$, $Z_4$, $Z_5$, $Z_6$, $Z_7$, $Z_8$, and $Z_9$ are independently $CR_2$; $Y_1$ is N; $Y_2$; $Y_3$, and $Y_4$ are C; one of $Z_2$, $Z_3$, $Z_6$, $Z_7$, $Z_8$, $Z_9$ is the carbon atom to which the remainder of the molecule is attached.

57. $Z_3$ is N; $Z_1$, $Z_2$, and $Z_4$ are independently $CR_2$; $Z_5$, $Z_6$, $Z_7$, $Z_8$, and $Z_9$ are independently $CR_2$ or N; $Y_1$, $Y_3$, $Y_4$ are C; $Y_2$ is N.

58. $Z_1$ is O, S, or N—$R_1$; $Z_2$, $Z_3$, and $Z_4$ are independently $CR_2$; $Z_5$ is $CR_2$ or N; $Z_6$, $Z_7$, $Z_8$, and $Z_9$ are independently $CR_2$, or N; one of $Z_6$, $Z_7$, $Z_8$, $Z_9$ is a carbon atom to which the remainder of the molecule is attached.

59. $Z_1$ and $Z_3$ are independently O, S, N—$R_1$, N, or $CR_2$; $Z_4$ is $CR_2$ or N; $Z_5$ is $CR_2$; $Z_6$, $Z_7$, $Z_8$, and $Z_9$ are independently $CR_2$, or N; $Y_1$, and $Y_2$ are independently C or N; $Y_3$ and $Y_4$ are C.

The Preferred embodiments of formula 4–C

60. $Z_1$ and $Z_2$ are independently N or $CR_2$; $Z_3$, $Z_4$, $Z_5$, $Z_6$, $Z_7$, and $Z_8$ are independently $CR_2$; $Y_1$ is C.

61. $Z_1$, and $Z_2$ are independently $CR_2$; $Z_3$, $Z_4$, $Z_5$, $Z_6$, $Z_7$, and $Z_8$ are independently N or $CR_2$; $Y_1$ is C.

62. $Z_1$, $Z_2$, $Z_3$, $Z_4$, $Z_5$, $Z_6$, $Z_7$, and $Z_8$ are independently N or $CR_2$; $Y_1$ is C.

The Preferred embodiments of formula 5-A

63. $Z_1$ is O, S, or N—$R_1$; $Z_2$, and $Z_3$ are independently $CR_2$; $Z_4$ is O, S, N—$R_1$, or $CR_2$; $Y_1$, and $Y_2$ are C; $Y_4$, and $Y_3$ are independently C, or N; $W_1$, $W_2$, $W_3$ are independently $CR_4R_4$; t=1 or 2.

64. $Z_1$ is O, S, or N—$R_1$; $Z_2$ and $Z_3$ are independently $CR_2$; $Z_4$ is O, S, N—$R_1$, or $CR_2$; $Y_1$, and $Y_2$ are C; $Y_4$, and $Y_3$ are independently C, or N; $W_1$, and $W_3$ are independently $CR_4R_4$; t=1 to 2; $W_2$ is O, S(O)r (r=0–2), N—$R_1$ or $CR_4R_4$.

65. $Z_3$ is N; $Z_2$ is $CR_2$; $Z_1$ is $CR_2$, or N; $Z_4$ is O, S, N—$R_1$, $W_1$, $W_2$, and $W_3$ are independently $CR_4R_4$; t=1 to 3; $Y_1$, $Y_3$, and $Y_4$ are C; $Y_2$ is N; one of $Z_1$, $Z_2$ or $Z_4$ is the carbon atom to which the remainder of the molecule is attached.

66. $Z_1$ is N; $Z_2$ is $CR_2$; $Z_3$ is $CR_2$, or N; $Z_4$ is O, S, or N—$R_1$; $W_1$, $W_2$, and $W_3$ are independently $CR_4R_4$; t=1 to 3; $Y_2$, $Y_3$, and $Y_4$ are C; $Y_1$ is N; one of $Z_2$, $Z_3$, $Z_4$ is the carbon atom to which the remainder of the molecule is attached.

67. $Z_3$ is N; $Z_2$ is $CR_2$; $Z_1$ is $CR_2$, or N; $Z_4$ is O, S, or N—$R_1$; $Y_1$, $Y_3$, and $Y_4$ are C; $Y_2$ is N; $W_1$, $W_2$, and $W_3$ are independently $CR_4R_4$, O S(O)r (r=0–2), or N—$R_1$ with the proviso that no S—S, S—O or O—O bond formation can occur to form a saturated ring; t=1 to 3; one of $Z_1$, $Z_2$ or $Z_4$ is the carbon atom to which the remainder of the molecule is attached.

68. $Z_1$ is N; $Z_2$ is $CR_2$; $Z_3$ is $CR_2$, or N; $Z_4$ is O, S, or N—$R_1$; $Y_2$, $Y_3$, and $Y_4$ are C; $Y_1$ is N; $W_1$, $W_2$, and $W_3$ are independently $CR_4R_4$, O, S═(O)r (r=0–2); or N—$R_1$, with the proviso that no S—S, S═O or O—O bond formation can occur to form a saturated ring; t=1–3; one of $Z_2$, $Z_3$, $Z_4$ is a carbon atom to which the remainder of the molecule is attached.

69. $Z_1$ is $CR_2$; $Z_2$ is the carbon atom to which the remainder of the molecule is attached; $Z_3$ is N; $Z_4$ is O, S, or N—$R_1$; $Y_1$ is C; $Y_2$ is N; $Y_3$, and $Y_4$ are C; $W_1$, $W_2$, and $W_3$ are independently $CR_4R_4$, O, S═(O)r (r=0–2), or N—$R_1$ with the proviso that no S—S, S═O or O—O bond formation can occur to form a saturated ring; t=1 to 3.

70. $Z_1$ is the carbon atom to which the remainder of the molecule is attached; $Z_2$ is $CR_2$; $Z_3$ is N; $Z_4$ is O, S, N—$R_1$; $Y_1$ is C; $Y_2$ is N; $Y_3$, and $Y_4$ are C; $W_1$, $W_2$, and $W_3$ are independently $CR_4R_4$, O, S═(O)r (r=0–2), or N—$R_1$ with the proviso that no S—S, S═O or O—O bond formation can occur to form a saturated ring; t=1–3.

71. $Z_1$, $Z_2$, and $Z_3$ are independently $CR_2$, or N; $Z_4$ is $CR_2$; $Y_1$, $Y_2$ are C; $Y_3$, $Y_4$ are N; $W_1$, $W_2$, and $W_3$ are independently $CR_4R_4$, O, S═(O)r (r=0–2), or N—$R_1$ with the proviso that no S—S, S—O or O—O bond formation can occur to form a saturated ring; t=1–3.

The Preferred embodiments of formula 5-B

72. $Z_1$, $Z_2$, $Z_3$, $Z_4$ are independently $CR_2$; $Y_1$, $Y_2$ are N; $W_1$, $W_2$ are independently O, S, N—$R_1$, or $CR_4R_4$; t=1–2.

73. $Z_1$, $Z_2$ are independently N, or $CR_2$; $Z_3$ is $CR_2$; $Z_4$ is O, S, or N—$R_1$; $W_1$, and $W_2$ are independently O, S, N—$R_1$, $CR_4R_4$; t=1–2.

The preferred embodiments of formula 6-A are:

74. $Z_1$ is O, S, N—$R_1$; $Z_2$, $Z_3$, $Z_4$, $Z_5$ are independently $CR_2$; $W_1$, $W_2$, $W_3$ are independently N—$R_1$, O, S═(O)r (r=0–2), or $CR_4R_4$; $Y_1$, $Y_2$ are C; t=1–3; one of $Z_2$, $Z_3$ is the carbon atom to which the remainder of the molecule is attached.

75. $Z_1$ is O, S, or N—$R_1$; $Z_3$ is N, O, or S; $Z_2$, $Z_4$, $Z_5$ are independently $CR_2$; $W_1$, $W_2$, $W_3$ are independently N—$R_1$, O, S═(O)r (r=0–2), or $CR_4R_4$; $Y_1$, and $Y_2$ are C; t1–3; $Z_2$ is the carbon atom to which the remainder of the molecule is attached.

76. $Z_1$ is $CR_2$; $Z_3$ is N; $Z_2$, $Z_4$, and $Z_5$ are independently $CR_2$; $W_1$, $W_2$, and $W_3$ are independently N—$R_1$, O, S═(O)r (r=0–2), or $CR_4R_4$; $Y_1$ is N; $Y_2$ is C; t=1–3; $Z_1$, or $Z_2$ is the carbon atom to which the remainder of the molecule is attached.

77. $Z_1$ is N; $Z_2$, $Z_3$, $Z_4$, $Z_5$ are independently $CR_2$; $W_1$, $W_2$, $W_3$ are independently N—$R_1$, O, S═(O)r (r=0–2), or $CR_4R_4$; $Y_1$ is C; $Y_2$ is N; t=1–3; $Z_2$, or $Z_3$ is the carbon atom to which the remainder of the molecule is attached.

78. $Z_1$ is O, S, or N—$R_1$; $Z_2$ is N, O, or S; $Z_3$, $Z_4$, and $Z_5$ are independently $CR_2$; $W_1$, $W_2$, and $W_3$ are independently N—$R_1$, O, S═(O)r (r=0–2), or $CR_4R_4$; $Y_1$, and $Y_2$ are C; t=1–3; one of $Z_3$ is a carbon atom to which the remainder of the molecule is attached.

79. $Z_1$ is O, S, or N—$R_1$; $Z_2$, and $Z_3$ are independently $CR_2$; $Z_4$, and $Z_5$ are independently $CR_2$, or N; $W_1$, $W_2$, and $W_3$ are independently N—$R_1$, O, S═(O)r (r=0–2), or $CR_4R_4$; $Y_1$, $Y_2$ are C; t=1–3; $Z_2$ or $Z_3$ is the carbon atom to which the remainder of the molecule is attached.

80. $Z_1$ is O, S, or N—$R_1$; $Z_3$ is N, O, or S; $Z_2$ is $CR_2$; $Z_4$, $Z_5$ are independently $CR_2$, are C; t=1–3; $Z_2$ is the carbon atom to which the remainder of the molecule is attached.

81. $Z_1$ is $CR_2$; $Z_3$ is N; $Z_2$ is $CR_2$; $Z_4$, $Z_5$ are independently N, or $CR_2$; $W_1$, $W_2$, $W_3$ are independently N—$R_1$, O, S═(O)r (r=0–2), or $CR_4R_4$; $Y_1$ is N; $Y_2$ is C; t=1–3; $Z_1$ or $Z_2$ is the carbon atom to which the remainder of the molecule is attached.

82. $Z_1$ is N; $Z_2$, and $Z_3$ are independently $CR_2$; $Z_4$, $Z_5$ are independently N or $CR_2$; $W_1$, $W_2$, $W_3$ are independently N—$R_1$, O, S═(O)r (r=0–2), or $CR_4R_4$; $Y_1$ is C; $Y_2$ is N; t=1–3; $Z_2$ or $Z_3$ is the carbon atom to which the remainder of the molecule is attached.

83. $Z_1$ is O, S, or N—$R_1$; $Z_2$ is N, O, or S; $Z_3$ is $CR_2$; $Z_4$, and $Z_5$ are independently N, or $CR_2$; $W_1$, $W_2$, $W_3$ are independently N—$R_1$, O, S═(O)r (r=0–2), or $CR_4R_4$; $Y_1$, $Y_2$ are C; t=1–3; $Z_3$ is the carbon atom to which the remainder of the molecule is attached.

The preferred embodiments of formula 6B are:

84. $Z_1$ is O, S, or N—$R_1$; $Z_2$, $Z_3$, $Z_4$, and $Z_5$ are independently $CR_2$; $W_1$, $W_2$, $W_3$ are independently N—$R_1$, O, S═(O)r (r=0–2), or $CR_4R_4$; $Y_1$, $Y_2$, $Y_3$, and $Y_4$ C; t=1–3; $Z_2$ or $Z_3$ is the carbon atom to which the remainder of the molecule is attached.

85. $Z_1$ is O, S, or N—$R_1$; $Z_3$ is N, O, or S; $Z_2$, $Z_4$, $Z_5$ are independently $CR_2$; $W_2$, $W_3$ are independently N—$R_1$, O, S═(O)r (r=0–2), or $CR_4R_4$; $Y_1$, $Y_2$, $Y_3$, $Y_4$ are C; t=1–3; $Z_2$ is the carbon atom to which the remainder of the molecule is attached.

86. $Z_1$ is $CR_2$; $Z_3$ is N; $Z_2$, $Z_4$, and $Z_5$ are independently $CR_2$; $W_1$, $W_2$, $W_3$ are independently N—$R_1$, O, S═(O)r (r=0–2), or $CR_4R_4$; $Y_3$ is N; $Y_1$, $Y_2$, $Y_4$ are C; t=1–3; $Z_1$, or $Z_2$ is the carbon atom to which the remainder of the molecule is attached.

87. $Z_1$ is N; $Z_2$, $Z_3$, $Z_4$, $Z_5$ are independently $CR_2$; $W_1$, $W_2$, $W_3$ are independently N-$R_1$, O, S=(O)$_r$ (r=0–2), or $CR_4R_4$; $Y_1$, $Y_2$, $Y_3$ are C; $Y_4$ is N; t=1–3; $Z_2$ or $Z_3$ is the carbon atom to which the remainder of the molecule is attached.

88. $Z_1$ is O, S, or N—$R_1$; $Z_2$ is N, O, or S; $Z_3$, $Z_4$, and $Z_5$ are independently $CR_2$; $W_1$, $W_2$, $W_3$ are independently N—$R_1$, O, S=(O)$_r$ (r=0–2), or $CR_4R_4$; $Y_1Y_2$, $Y_3$, and $Y_4$ are C; t=1–3; $Z_3$ is the carbon atom to which the remainder of the molecule is attached.

89. $Z_1$ is O, S, or N—$R_1$; $Z_2$, and $Z_3$ are independently $CR_2$; $Z_4$, and $Z_5$ are independently $CR_2$, or N; $W_1$, $W_2$, $W_3$ are independently N—$R_1$, O, S=(O)$_r$ (r=0–), or $CR_4R_4$; $Y_1$, $Y_2$, $Y_3$, $Y_4$ are C; t=1–3; $Z_2$ or $Z_3$ is the which the remainder of the molecule is attached.

90. $Z_1$ is O, S, or N—$R_1$; $Z_3$ is N, O, or S; $Z_2$ is $CR_2$; $Z_4$, and $Z_5$ are independently $CR_2$ or N; $W_1$, $W_2$, $W_3$ are independently N—$R_1$, O, S=(O)$_r$ (r=0–2), or $CR_4R_4$; $Y_1$, $Y_2$, $Y_3$, $Y_4$ are C; t=1–3; $Z_2$ is the carbon atom to which the remainder of the molecule is attached.

91. $Z_1$ is $CR_2$; $Z_3$ is N; $Z_2$ is $CR_2$; $Z_4$, and $Z_5$ are independently N, $CR_2$; $W_1$, $W_2$, $W_3$ are independently N—$R_1$, O, S=(O)$_r$ (r=0–2), or $CR_4R_4$; $Y_3$ is N; $Y_1$, $Y_2$, $Y_4$ are C; t=1–3; $Z_1$ or $Z_2$ is the carbon atom to which the remainder of the molecule is attached.

92. $Z_1$ is N; $Z_2$, $Z_3$ are independently $CR_2$; $Z_4$, $Z_5$ are independently N, or $CR_2$; $W_1$, $W_2$, $W_3$ are independently N—$R_1$, O, S=(O), (r=0–2), or $CR_4R_4$; $Y_1$, $Y_2$, $Y_3$ are C; $Y_4$ is N; t=1–3; $Z_2$, or $Z_3$ is the carbon atom to which the remainder of the molecule is attached.

93. $Z_1$ is O, S, or N—$R_1$; $Z_2$ is N, O, or S; $Z_3$ is $CR_2$; $Z_4$, $Z_5$ are independently N, or $CR_2$; $W_1$, $W_2$, $W_3$ are independently N—$R_1$, O, S=(O)$_r$ (r=0–2), or $CR_4R_4$; $Y_1$, $Y_2$, $Y_3$, $Y_4$ are C; t=1–3; $Z_3$ is the carbon atom to which the remainder of the molecule is attached.

The preferred embodiments of formula 6–C are:

94. $Z_1$, $Z_3$, $Z_4$, and $Z_5$ are independently N or $CR_2$; $Z_2$ is O, S, or N—$R_1$; $Y_1Y_2$ are C; $W_1$, $W_2$ are independently N—$R_1$, O, S=(O)$_r$ (r=0–2), $CR_4R_4$; t=1–2.

95. $Z_1$, $Z_3$, $Z_4$, $Z_5$ are independently $CR_2$; $Z_2$ is O, S, or N—$R_1$; $Y_1$, $Y_2$ are C; $W_1$, $W_2$ are independently N—$R_1$, O, S=(O)$_r$ (r=0–2), or $CR_4R_4$; t=1–2.

96. $Z_1$, $Z_3$, $Z_5$ are independently $CR_2$; $Z_2$ is O, S, N—$R_1$; $Z_4$ is N; $Y_1$ $Y_2$ are C; $W_1$, $W_2$ are independently N—$R_1$, O, S=(O)$_r$ (r=0–2), or $CR_4R_4$; t=1–2.

97. $Z_1$, $Z_2$, $Z_3$, $Z_4$, and $Z_5$ are independently $CR_2$; $Y_1$ is C; $Y_2$ is N; $W_1W_2$ are independently N—$R_1$, O, S=(O)$_r$ (r=0–2), or $CR_4R_4$; t=1–2.

98. $Z_1$, $Z_2$, $Z_3$, $Z_5$ are independently $CR_2$; $Z_4$ is N; $Y_1$ is C; $Y_2$ is N; $W_1$, $W_2$ are independently N—$R_1$, O, S=(O)$_r$ (r=0–2), or $CR_4R_4$; t=1–2.

The preferred embodiments of formula 7-A are:

99. $Z_3$, $Z_6$ are independently O, S, or N—$R_1$; $Z_1$, $Z_2$, $Z_4$, $Z_5$ are independently $CR_2$; $W_1$, $W_2$ are independently N—$R_1$, O, S=(O), (r=0–2), or $CR_4R_4$; t=1–2.

100. $Z_3$, $Z_6$ are independently O, S, or N—$R_1$; $Z_1$, $Z_4$ are N; $Z_2$, $Z_5$ are independently $CR_2$; $W_1$, $W_2$ are independently N—$R_1$, O, S=(O)$_r$ (r=0–2), or $CR_4R_4$; t=1–2; $Z_2$ or $Z_5$ is the carbon atom to which the remainder of the molecule is attached.

101. $Z_1$, $Z_4$ are independently O, S, or N—$R_1$; $Z_2$, $Z_3$, $Z_5$, $Z_6$ are independently $CR_2$; $W_1$, $W_2$ are independently N—$R_1$, O, S=(O)$_r$ (r=0–2), or $CR_4R_4$; t=1–2.

102. $Z_1$, $Z_4$ are independently O, S, or N—$R_1$; $Z_3$, $Z_6$ are N; $Z_2$, $Z_5$ are independently $CR_2$; $W_1$, $W_2$ are independently N—$R_1$, O, S=(O)$_r$ (r=0–2), or $CR_4R_4$; t=1–2; $Z_2$ or $Z_5$ is the carbon atom to which the remainder of the molecule is attached.

103. $Z_2$, $Z_5$ are independently O, S, or N—$R_1$; $Z_1$, $Z_3$, $Z_4$, $Z_6$ are independently $CR_2$; $W_1$, $W_2$ are independently N—$R_1$, O, S=(O)$_r$ (r=0–2), or $CR_4R_4$; t=1–2.

104. $Z_2$, $Z_5$ are independently O, S, N—$R_1$; $Z_1$, $Z_3$, $Z_4$, $Z_6$ are independently $CR_2$, N, S; $W_1$, $W_2$ are independently N—$R_1$, O, S=(O)$_r$ (r=0–2), $CR_4R_4$; t=1–2; One of $Z_1$, $Z_3$, $Z_4$, $Z_6$ is the carbon atom to which the remainder of the molecule is attached.

105. $Z_1$ is $CR_2$, N; $Z_2$ is $CR_2$; $Z_3$ is N; $Z_4$, $Z_5$ are independently $CR_2$; $Z_6$ is N; $Y_1$, $Y_3$ are independently $CR_2$; $Y_2$, $Y_4$ are N; $W_1$, $W_2$ are independently N—$R_1$, O, S=(O)$_r$ (r=0–2), or $CR_4R_4$; t=1–2; One of $Z_1$, $Z_2$, $Z_4$, $Z_5$ is the carbon atom to which the remainder of the molecule is attached.

106. $Z_1$ is $CR_2$, or N; $Z_2$ is $CR_2$; $Z_3$ is O, S, N—$R_1$; $Z_4$ $Z_5$ are independently $CR_2$; $Z_6$ is N; $Y_1$, $Y_4$, $Y_3$ are independently $CR_2$; $Y_2$ is N; $W_1$, $W_2$ are independently N—$R_1$, O, S=(O)$_r$ (r=0–2), $CR_4R_4$; t=1–2; One of $Z_1$, $Z_2$, $Z_4$, $Z_5$ is the carbon atom to which the remainder of the molecule is attached.

107. $Z_1$ is $CR_2$, or N; $Z_2$ is $CR_2$; $Z_3$ is N; $Z_4$, $Z_5$, $Z_6$ are independently N, or $CR_2$, $Y_1$, and $Y_3$ are N; $Y_2$, $Y_4$ are independently $CR_2$; $W_1$, $W_2$ are independently N—$R_1$, O, S=(O)$_r$ (r=0–2), or $CR_4R_4$; t=1–2; One of $Z_1$, $Z_2$, $Z_4$, $Z_5$, $Z_6$ is the carbon atom to which the remainder of the molecule is attached.

The preferred embodiments of formula 7-B are:

108. $Z_1$, $Z_2$, $Z_4$, $Z_5$, $Z_6$ are independently $CR_2$; $Z_3$ is O, S, or N—$R_1$; $Y_1$, $Y_2$, $Y_4$ are C; $Y_3$ is N; $W_1$, $W_2$ are independently N—$R_1$, O, S=(O)$_r$ (r=0–2), or $CR_4R_4$; t=1–2.

109. $Z_1$, $Z_2$, $Z_4$, $Z_5$, $Z_6$ are independently $CR_2$ or N; $Z_3$ is O, S, or N—$R_1$; $Y_1$, $Y_2$, $Y_4$ are C; $Y_3$ is N; $W_1$, $W_2$ are independently N—$R_1$, O, S=(O)$_r$ (r=0–2), or $CR_4R_4$; t=1–2; One of $Z_1$, $Z_2$, $Z_4$, $Z_5$, $Z_6$ is the carbon atom to which the remainder of the molecule is attached.

110. $Z_1$, $Z_2$, $Z_3$, $Z_5$, $Z_6$ are independently $CR_2$; $Z_4$ is O, S, or N—$R_1$; $Y_1$ $_{Y1}$, $Y_2$, $Y_3$ are C; $Y_4$ is N; $W_1$, $W_2$ are independently N—$R_1$, O, S=(O)$_r$ (r=0–2), or $CR_4R_4$; t=1–2; One of $Z_1$, $Z_2$, $Z_3$, $Z_5$, $Z_6$ is the carbon atom to which the remainder of the molecule is attached.

111. $Z_1$, $Z_2$, $Z_3$, $Z_5$, $Z_6$ are independently $CR_2$ or N; $Z_4$ is O, S, or N—$R_1$; $Y_1$, $Y_2$, $Y_3$ are C; $Y_4$ is N; $W_1$, $W_2$ are independently N—$R_1$, O, S=(O)$_r$ (r=0–2), or $CR_4R_4$; t=1–2; One of $Z_1$, $Z_2$, $Z_3$, $Z_5$, $Z_6$ is the carbon atom to which the remainder of the molecule is attached.

112. $Z_1$, $Z_2$, $Z_3$, $Z_4$, $Z_5$, $Z_6$ are independently $CR_2$; $Y_1$, $Y_3$ are N; $Y_2$, $Y_4$ are C; $W_1$, $W_2$ are independently N—$R_1$, O, S=(O) (r=0–2), or $CR_4R_4$; t=1–2; One of $Z_1$, $Z_2$, $Z_3$, $Z_4$, $Z_5$, $Z_6$ is the carbon atom to which the remainder of the molecule is attached.

113. $Z_1$, $Z_2$, $Z_3$, $Z_4$, $Z_5$, $Z_6$ are independently $CR_2$ or N; $Y_1$, $Y_3$ are N; $Y_2$, $Y_4$ are C: $W_1$, $W_2$ are independently N—$R_1$, O, S=(O)$_r$ (r=0–2), or $CR_4R_4$; t=1–2; One of $Z_1$, $Z_2$, $Z_3$, $Z_4$, $Z_5$, $Z_6$ is the carbon atom to which the remainder of the molecule is attached.

114. $Z_1$, $Z_3$, $Z_4$, $Z_5$, $Z_6$ are independently $CR_2$; $Z_2$ is O, S, or N—$R_1$; $Y_1$, $Y_2$, $Y_4$ is C; $Y_3$ is N; $W_1$, $W_2$ are independently N—$R_1$, O, S=(O)$_r$ (r=0–2), or $CR_4R_4$; t=1–2; One of $Z_1$, $Z_3$, $Z_4$, $Z_5$, $Z_6$ is the carbon atom to which the remainder of the molecule is attached.

115. $Z_1$, $Z_3$, $Z_4$, $Z_5$, $Z_6$ are independently $CR_2$, or N; $Z_2$ is O, S, or N—$R_1$; $Y_1$, $Y_2$, $Y_4$ are C; $Y_3$=N; $W_1$, $W_2$ are independently N—$R_1$, O, S=(O)$_r$ (r=0–2), or $CR_4R_4$;

116. $Z_1$, $Z_2$, $Z_4$, $Z_6$ are independently $CR_2$; $Z_3$, $Z_5$ are independently O, S, or N—$R_1$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_4$, $Z_6$ is the carbon atom to which the remainder of the molecule is attached.

117. $Z_1$, $Z_2$, $Z_4$, $Z_6$ are independently $CR_2$, or N; $Z_3$, $Z_5$ are independently O, S, or N—$R_1$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_4$, $Z_6$ is the carbon atom to which the remainder of the molecule is attached.

118. $Z_1$, $Z_2$, $Z_4$, $Z_5$ are independently $CR_2$; $Z_3$, $Z_6$ are independently O, S, or N—R—$R_1$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_4$, $Z_5$ is the carbon atom to which the remainder of the molecule is attached.

119-$Z_1$, $Z_2$, $Z_4$, $Z_5$ are independently $CR_2$, or N; $Z_3$, $Z_6$ are independently O, S, or N—$R_1$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_4$, $Z_5$ is the carbon atom to which the remainder of the molecule is attached.

120. $Z_1$, $Z_2$, $Z_5$, $Z_6$ are independently $CR_2$; $Z_3$, $Z_4$ are independently O, S, or N—$R_1$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_5$, $Z_6$ is the carbon atom to which the remainder of the molecule is attached.

121. $Z_1$, $Z_2$, $Z_5$, $Z_6$ are independently $CR_2$ or N; $Z_3$, $Z_4$ are independently O, S, or N—$R_1$; $Y_1$, $Y_2$, $Y_3$, $Y_4$ are C; $W_1$, $W_2$ are independently N—$R_1$, O, S=(O)$_r$ (r=0–2), $CR_4R_4$; t=1–2; One of $Z_1$, $Z_2$, $Z_5$, $Z_6$ is the carbon atom to which the remainder of the molecule is attached.

122. $Z_1$, $Z_2$, $Z_4$, $Z_5$ are independently $CR_2$; $Z_3$, $Z_6$ are independently O, S, or N—$R_1$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_5$, $Z_6$ is the carbon atom to which the remainder of the molecule is attached.

123. $Z_1$, $Z_2$, $Z_4$, $Z_5$ are independently $CR_2$, or N; $Z_3$, $Z_6$ are independently O, S, or N—$R_1$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_5$, $Z_6$ is the carbon atom to which the remainder of the molecule is attached.

124. $Z_1$, $Z_2$, $Z_3$, $Z_4$, $Z_6$ are independently $CR_2$; $Z_5$ is O, S, or N—$R_1$; $Y_1$ is N; $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_3$, $Z_4$, $Z_6$ is the carbon atom to which the remainder of the molecule is attached.

125. $Z_1$, $Z_2$, $Z_3$, $Z_4$, $Z_6$ are independently $CR_2$, or N; $Z_5$ is O, S, or N—$R_1$; $Y_1$ is N; $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_3$, $Z_4$, $Z_6$ is the carbon atom to which the remainder of the molecule is attached.

126. $Z_1$, $Z_3$, $Z_4$, $Z_6$ are independently $CR_2$; $Z_2$, $Z_5$ are independently O, S, or N—$R_4$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_3$, $Z_4$, $Z_6$ is the carbon atom to which the remainder of the molecule is attached.

127. $Z_1$, $Z_3$, $Z_4$, $Z_6$ are independently $CR_2$ or N; $Z_2$, $Z_5$ are independently O, S, or N—$R_1$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_3$, $Z_4$, $Z_6$ is the carbon atom to which the remainder of the molecule is attached.

The preferred embodiments of formula 8-A are:

128. $Z_1$ is O, S, or N—$R_1$; $Z_2$, $Z_4$, $Z_5$, $Z_6$, $Z_7$ are independently $CR_2$; $Z_3$ is $CR_2$, or N; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_2$, $Z_3$, $Z_4$, $Z_5$, $Z_6$ is the carbon atom to which the remainder of the molecule is attached.

129. $Z_1$ is O, S, or N—$R_1$; $Z_2$, $Z_4$, $Z_5$, $Z_6$, $Z_7$ are independently $CR_2$; $Z_3$ is $CR_2$, $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_2$, $Z_3$, $Z_4$, $Z_5$, $Z_6$, $Z_7$ is the carbon atom to which the remainder of the molecule is attached.

130. $Z_1$ is O, S, or N—$R_1$; $Z_2$, $Z_4$, $Z_5$, $Z_6$, $Z_7$ are independently $CR_2$; $Z_3$ is N; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_2$, $Z_4$, $Z_5$, $Z_6$, $Z_7$ is the carbon atom to which the remainder of the molecule is attached.

131. $Z_1$ is O, S, or N—$R_1$; $Z_3$, $Z_4$, $Z_5$, $Z_6$, $Z_7$ are independently $CR_2$; $Z_2$ is $CR_2$, or N; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_2$, $Z_3$, $Z_4$, $Z_5$, $Z_6$, $Z_7$ is the carbon atom to which remainder of the molecule is attached.

132. $Z_1$ is O, S, or N—$R_1$; $Z_3$, $Z_4$, $Z_5$, $Z_6$, $Z_7$ are independently $CR_2$; $Z_2$ is N; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_3$, $Z_4$, $Z_5$, $Z_6$, $Z_7$ is the carbon atom to which the remainder of the molecule is attached.

133. $Z_1$ is O, S, or N—$R_1$; $Z_3$, $Z_4$, $Z_5$, $Z_6$, $Z_7$ are independently $CR_2$; $Z_2$ is $CR_2$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_2$, $Z_3$, $Z_4$, $Z_5$, $Z_6$, $Z_7$ is the carbon atom to which the remainder of the molecule is attached.

134. $Z_1$ is O, S, or N—$R_1$; $Z_2$, $Z_3$, $Z_4$, $Z_5$, $Z_6$, $Z_7$ are independently N or $CR_2$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_2$, $Z_3$, $Z_4$, $Z_5$, $Z_6$, $Z_7$ is the carbon atom to which the remainder of the molecule is attached.

135. $Z_1$ is O, S, or N—$R_1$; $Z_2$ is $CR_2$; $Z_4$, $Z_5$, $Z_6$, $Z_7$ are independently N or $CR_2$; $Z_3$ is $CR_2$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_2$, $Z_3$, $Z_4$, $Z_5$, $Z_6$, $Z_7$ is the carbon atom to which the remainder of the molecule is attached.

136. $Z_1$ is O, S, or N—$R_1$; $Z_2$ is $CR_2$; $Z_4$, $Z_5$, $Z_6$, and $Z_7$ are independently N or $CR_2$; $Z_3$ is N; $Y_1$, $Y_2$, $Y_3$, $Y_4$ are C; $W_1$, and $W_2$ are independently N—$R_1$, O, S=(O)$_r$ (r=0–2), or $CR_4R_4$; t=1–2; One of $Z_2$, $Z_4$, $Z_5$, $Z_6$, $Z_7$ is the carbon atom to which the remainder of the molecule is attached.

137. $Z_1$ is O, S, or N—$R_1$; $Z_4$, $Z_5$, $Z_6$, and $Z_7$ are independently N or $CR_2$; $Z_2$ and $Z_3$ are independently $CR_2$ or N; $Y_1$, $Y_2$, $Y_3$, $Y_4$ are C; $W_1$ and $W_2$ are independently N—$R_1$, O, S=(O)$_r$ (r=0–2), or $CR_4R_4$; t=1–2; One of $Z_2$, $Z_3$, $Z_4$, $Z_5$, $Z_6$, $Z_7$ is the carbon atom to which the remainder of the molecule is attached.

138. $Z_1$ is O, S, or N—$R_1$; $Z_3$ is $CR_2$; $Z_4$, $Z_5$, $Z_6$, and $Z_7$ are independently N or $CR_2$; $Z_2$ is N; $Y_1$, $Y_2$, $Y_3$, and $Y_4$ are C; $W_1$ and $W_2$ are independently N—$R_1$, O, S=(O)$_r$ (r=0–2), or $CR_4R_4$; t=1–2; One of $Z_3$, $Z_4$, $Z_5$, $Z_6$, $Z_7$ is the carbon atom to which the remainder of the molecule is attached.

139. $Z_1$ is O, S, N—$R_1$; $Z_4$, $Z_5$, $Z_6$, and $Z_7$ are independently N or $CR_2$; $Z_2$ and $Z_3$ are independently $CR_2$; $Y_1$, $Y_2$, $Y_3$, $Y_4$ are C; $W_1$ and $W_2$ are independently N—$R_1$, O, S=(O)$_r$ (r=0–2), or $CR_4R_4$; t=1–2; One of $Z_2$, $Z_3$, $Z_4$, $Z_5$, $Z_6$, $Z_7$ is the carbon atom to which the remainder of the molecule is attached.

140. $Z_3$ is O, S, or N—$R_1$; $Z_2$, $Z_4$, $Z_5$, $Z_6$, and $Z_7$ are independently $CR_2$; $Z_1$ is $CR_2$ or N; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_4$, $Z_5$, $Z_6$, $Z_7$ is the carbon atom to which the remainder of the molecule is attached.

141. $Z_3$ is O, S, or N—$R_1$; $Z_1$, $Z_2$, $Z_4$, $Z_5$, $Z_6$, $Z_7$ are independently $CR_2$; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_4$, $Z_5$, $Z_6$, $Z_7$ is the carbon atom to which the remainder of the molecule is attached.

142. $Z_3$ is O, S, or N—$R_1$; $Z_2$, $Z_4$, $Z_5$, $Z_6$, and $Z_7$ are independently $CR_2$; $Z_1$ is N; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_4$, $Z_5$, $Z_6$, $Z_7$ is the carbon atom to which the remainder of the molecule is attached.

143. $Z_3$ is O, S, or N—$R_1$; $Z_1$, $Z_4$, $Z_5$, $Z_6$, $Z_7$ are independently $CR_2$; $Z_2$ is $CR_2$ or N; $Y_1$, $Y_2$, $Y_3$, $Y_4$ are C; $W_1$, $W_2$ are independently N—$R_1$, O, S=(O)$_r$ (r=0–2), or $CR_4R_4$; t=1–2; One of $Z_1$, $Z_2$, $Z_4$, $Z_5$, $Z_6$, $Z_7$ is the carbon atom to which the remainder of the molecule is attached.

144. $Z_3$ is O, S, or N—$R_1$; $Z_1$, $Z_4$, $Z_5$, $Z_6$, $Z_7$ are independently $CR_2$; $Z_2$ is N; $Y_1$, $Y_2$, $Y_3$, $Y_4$ are C; $W_1$ and $W_2$ are independently N—$R_1$, O, S=(O)$_r$ (r=0–2), or $CR_4R_4$; t=1–2; One of $Z_1$, $Z_4$, $Z_5$, $Z_6$, $Z_7$ is the carbon atom to which the remainder of the molecule is attached.

145. $Z_3$ is O, S, or N—$R_1$; $Z_1$, $Z_2$, $Z_4$, $Z_5$, $Z_6$, $Z_7$ are independently $CR_2$; $Y_1$, $Y_2$, $Y_3$, $Y_4$ are C; $W_1$ and $W_2$ are independently N—$R_1$, O, S=(O)$_r$ (r=0–2), or $CR_4R_4$; t=1–2; One of $Z_1$, $Z_2$, $Z_4$, $Z_5$, $Z_6$, $Z_7$ is the carbon atom to which the remainder of the molecule is attached.

146. $Z_3$ is O, S, or N—$R_1$; $Z_2$, $Z_4$, $Z_5$, $Z_6$, $Z_7$ are independently N or $CR_2$; $Z_1$ is $CR_2$, or N; $Y_1$, $Y_2$, $Y_3$, $Y_4$ are C; $W_1$, $W_2$ are independently N—$R_1$, O, S=(O)$_r$ (r=0–2), $CR_4R_4$; t=1–2; One of $Z_1$, $Z_2$, $Z_4$, $Z_5$, $Z_6$, $Z_7$ is the carbon atom to which the remainder of the molecule is attached.

147. $Z_3$ is O, S, or N—$R_1$; $Z_2$ is $CR_2$; $Z_4$, $Z_5$, $Z_6$, $Z_7$ are independently N or $CR_2$; $Z_1$ is $CR_2$; $Y_1$, $Y_2$, $Y_3$, $Y_4$ are C; $W_1$ and $W_2$ are independently N—$R_1$, O, S=(O)$_r$ (r=0–2), or $CR_4R_4$; t=1–2; One of $Z_1$, $Z_2$, $Z_4$, $Z_5$, $Z_6$, $Z_7$ is the carbon atom to which the remainder of the molecule is attached.

148. $Z_3$ is O, S, or N—$R_1$; $Z_2$ is $CR_2$; $Z_4$, $Z_5$, $Z_6$, and $Z_7$ are independently N or $CR_2$; $Z_1$ is N; $Y_1$, $Y_2$, $Y_3$, $Y_4$ are C; $W_1$ and $W_2$ are independently N—$R_1$, O, S=(O)$_r$ (r=0–2), or $CR_4R_4$; t=1–2; One of $Z_2$, $Z_4$, $Z_5$, $Z_6$, $Z_7$ is the carbon atom to which the remainder of the molecule is attached.

149. $Z_3$ is O, S, or N—$R_1$; $Z_4$, $Z_5$, $Z_6$, and $Z_7$ are independently N or $CR_2$; $Z_2$ and $Z_1$ are independently $CR_2$ or N; $Y_1$, $Y_2$, $Y_3$, $Y_4$ are C; $W_1$ and $W_2$ are independently N—$R_1$, O, S=(O)$_r$ (r=0–2), or $CR_4R_4$; t=1–2; One of $Z_1$, $Z_2$, $Z_4$, $Z_5$, $Z_6$, $Z_7$ is the carbon atom to which the remainder of the molecule is attached.

150. $Z_3$ is O, S, N—$R_1$; $Z_1$ is $CR_2$; $Z_4$, $Z_5$, $Z_6$, $Z_7$ are independently N or $CR_2$; $Z_2$ is N; $Y_1$, $Y_2$, $Y_3$, $Y_4$ are C; $W_1$, $W_2$ are independently N—$R_1$, O, S=(O)$_r$ (r=0–2), $CR_4R_4$; t=1–2; One of $Z_1$, $Z_4$, $Z_5$, $Z_6$, and $Z_7$ is the carbon atom to which the remainder of the molecule is attached.

151. $Z_3$ is O, S, N—$R_1$; $Z_4$, $Z_5$, $Z_6$, and $Z_7$ are independently N or $CR_2$; $Z_1$, and $Z_2$ are independently $CR_2$; $Y_1$, $Y_2$, $Y_3$, $Y_4$ are C; $W_1$ and $W_2$ are independently N—$R_1$, O, S=(O)$_r$ (r=0–2), or $CR_4R_4$; t=1–2; One of $Z_1$, $Z_2$, $Z_4$, $Z_5$, $Z_6$, and $Z_7$ is the carbon atom to which the remainder of the molecule is attached.

152. $Z_1$, $Z_2$, $Z_3$, $Z_4$, $Z_5$, $Z_6$, and $Z_7$ are independently $CR_2$; $Y_4$ is N; $Y_1$, $Y_2$, $Y_3$ are C; $W_1$, $W_2$ are independently N—$R_1$, O, S=(O)$_r$ (r=0–2), or $CR_4R_4$; t=1–2; One of $Z_1$, $Z_2$, $Z_3$, $Z_4$, $Z_5$, $Z_6$, $Z_7$ is the carbon atom to which the remainder of the molecule is attached.

153. $Z_1$ is N; $Z_2$, $Z_3$, $Z_4$, $Z_5$, $Z_6$, and $Z_7$ are independently $CR_2$; $Y_4$ is N; $Y_1$, $Y_2$, $Y_3$ are C; $W_1$ and $W_2$ are independently N—$R_1$, O, S=(O)$_r$ (r=0–2), or $CR_4R_4$; t=1–2; One of $Z_2$, $Z_3$, $Z_4$, $Z_5$, $Z_6$, and $Z_7$ is the carbon atom to which the remainder of the molecule is attached.

154. $Z_2$ is N; $Z_1$, $Z_3$, $Z_4$, $Z_5$, $Z_6$, $Z_7$ are independently $CR_2$; $Y_4$ is N; $Y_1$, $Y_2$, $Y_3$ are C; $W_1$ and $W_2$ are independently N—$R_1$, O, S=(O)$_r$ (r=0–2), $CR_4R_4$; t=1–2; One of $Z_1$, $Z_3$, $Z_4$, $Z_5$, $Z_6$, and $Z_7$ is the carbon atom to which the remainder of the molecule is attached.

155. $Z_3$ is N; $Z_1$, $Z_2$, $Z_4$, $Z_5$, $Z_6$, and $Z_7$ are independently $CR_2$; $Y_4$ is N; $Y_1$, $Y_2$, $Y_3$ are C; $W_1$, $W_2$ are independently N—$R_1$, O, S=(O)$_r$ (r=0–2), or $CR_4R_4$; t=1–2; One of $Z_1$, $Z_2$, $Z_4$, $Z_5$, $Z_6$, and $Z_7$ is the carbon atom to which the remainder of the molecule is attached.

156. $Z_1$ and $Z_2$ are N; $Z_3$, $Z_4$, $Z_5$, $Z_6$, $Z_7$ are independently $CR_2$; $Y_4$ is N; $Y_1$, $Y_2$, $Y_3$ are C; $W_1$, $W_2$ are independently N—$R_1$, O, S=(O)$_r$ (r=0–2), $CR_4R_4$; t=1–2; One of $Z_3$, $Z_4$, $Z_5$, $Z_6$, $Z_7$ is the carbon atom to which the remainder of the molecule is attached.

157. $Z_1$, $Z_3$ are N; $Z_2$, $Z_4$, $Z_5$, $Z_6$, $Z_7$ are independently $CR_2$; $Y_4$ is N; $Y_1$, $Y_2$, $Y_3$ are C; $W_1$, $W_2$ are independently N—$R_1$, O, S=(O)$_r$ (r=0–2), $CR_4R_4$; t=1–2; One of $Z_1$, $Z_2$, $Z_3$, $Z_4$, $Z_5$, $Z_6$, $Z_7$ is the carbon atom to which the remainder of the molecule is attached.

158. $Z_1$, $Z_2$, $Z_3$ are N; $Z_4$, $Z_5$, $Z_6$, $Z_7$ are independently $CR_2$; $Y_4$ is N; $Y_1$, $Y_2$, $Y_3$ are C; $W_1$, $W_2$ are independently N—$R_1$, O, S=(O)$_r$ (r=0–2), $CR_4R_4$; t=1–2; One of $Z_4$, $Z_5$, $Z_6$, $Z_7$ is the carbon atom to which the remainder of the molecule is attached.

159. $Z_1$, $Z_2$, $Z_3$ are independently $CR_2$; $Z_4$, $Z_5$, $Z_6$, $Z_7$ are independently N, $CR_2$; $Y_4$ is N; $Y_1$, $Y_2$, $Y_3$ are C; $W_1$, $W_2$ are independently N—$R_1$, O, S=(O)$_r$ (r=0–2), $CR_4R_4$; t=1–2; One of $Z_1$, $Z_2$, $Z_3$, $Z_4$, $Z_5$, $Z_6$, $Z_7$ is the carbon atom to which the remainder of the molecule is attached.

160. $Z_1$ is N; $Z_2$, $Z_3$ are independently $CR_2$; $Z_4$, $Z_5$, $Z_6$, $Z_7$ are independently N, $CR_2$; $Y_4$ is N; $Y_1$, $Y_2$, $Y_3$ are C; $W_1$, $W_2$ are independently N—$R_1$, O, S=(O)$_r$ (r=0–2), $CR_4R_4$; t=1–2; One of $Z_2$, $Z_3$, $Z_4$, $Z_5$, $Z_6$, $Z_7$ is the carbon atom to which the remainder of the molecule is attached.

161. $Z_2$ is N; $Z_1$, $Z_3$ are independently $CR_2$; $Z_4$, $Z_5$, $Z_6$, $Z_7$ are independently N, $CR_2$; $Y_4$ is N; $Y_1$, $Y_2$, $Y_3$ are C; $W_1$, $W_2$ are independently N—$R_1$, O, S=(O)$_r$ (r=0–2), $CR_4R_4$; t=1–2; One of $Z_1$, $Z_3$, $Z_4$, $Z_5$, $Z_6$, $Z_7$ is the carbon atom to which the remainder of the molecule is attached.

162. $Z_3$ is N; $Z_1$, $Z_2$ are independently $CR_2$; $Z_4$, $Z_5$, $Z_6$, $Z_7$ are independently N, $CR_2$; $Y_4$ is N; $Y_1$, $Y_2$, $Y_3$ are C; $W_1$, $W_2$ are independently N—$R_1$, O, S=(O)$_r$ (r=0–2), $CR_4R_4$; t=1–2; One of $Z_1$, $Z_2$, $Z_4$, $Z_5$, $Z_6$, $Z_7$ is the carbon atom to which the remainder of the molecule is attached.

163. $Z_1$, $Z_2$ are N; $Z_3$ are independently $CR_2$; $Z_4$, $Z_5$, $Z_6$, $Z_7$ are independently N, $CR_2$; $Y_4$ is N; $Y_1$, $Y_2$, $Y_3$ are C; $W_1$, $W_2$ are independently N—$R_1$, O, S=(O)$_r$ (r=0–2), $CR_4R_4$; t=1–2; One of $Z_3$, $Z_4$, $Z_5$, $Z_6$, $Z_7$ is the carbon atom to which the remainder of the molecule is attached.

164. $Z_1$, $Z_3$ are N; $Z_2$ are independently $CR_2$; $Z_4$, $Z_5$, $Z_6$, $Z_7$ are independently N, $CR_2$; $Y_4$ is N; $Y_1$, $Y_2$, $Y_3$ are C; $W_1$, $W_2$ are independently N—$R_1$, O, S=(O)$_r$ (r=0–2), $CR_4R_4$; t=1–2; One of $Z_1$, $Z_2$, $Z_3$, $Z_4$, $Z_5$, $Z_6$, $Z_7$ is the carbon atom to which the remainder of the molecule is attached.

165. $Z_1$, $Z_2$, $Z_3$ are N; $Z_4$, $Z_5$, $Z_6$, $Z_7$ are independently N, $CR_2$; $Y_4$ is N; $Y_1$, $Y_2$, $Y_3$ are C; $W_1$, $W_2$ are independently N—$R_1$, O, S=(O)$_r$ (r=0–2), $CR_4R_4$; t=1–2; One of $Z_4$, $Z_5$, $Z_6$, $Z_7$ is the carbon atom to which the remainder of the molecule is attached.

The preferred embodiments of formula 8-B are:

166. $Z_1$ is O, S, N—$R_1$; $Z_2$, $Z_3$, $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0–2), $CR_4R_4$;

t=0–2; One of $Z_2$, $Z_3$, $Z_4$, $Z_5$, $Z_6$, $Z_7$ is the carbon atom to which the remainder of the molecule is attached.

167. $Z_1$ is O, S, N—$R_1$; $Z_2$, $Z_3$, $Z_4$, $Z_5$, $Z_6$, $Z_7$ are $CH_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2; One of $Z_2$, $Z_3$, $Z_4$, $Z_5$, $Z_6$, $Z_7$ is the carbon atom to which the remainder of the molecule is attached.

168. $Z_1$ is O, S, N—$R_1$; $Z_2$ is N; $Z_3$, $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2; One of $Z_3$, $Z_4$, $Z_5$, $Z_6$, $Z_7$ is the carbon atom to which the remainder of the molecule is attached.

169. $Z_1$ is O, S, N—$R_1$; $Z_2$, $Z_3$ are N; $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2; One of $Z_4$, $Z_5$, $Z_6$, $Z_7$ is the carbon atom to which the remainder of the molecule is attached.

170. $Z_1$ is O, S, N—$R_1$; $Z_2$, $Z_3$, $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2; One of $Z_3$ is N; $Z_2$, $Z_4$, $Z_5$, $Z_6$, $Z_7$ is the carbon atom to which the remainder of the molecule is attached.

171. $Z_2$ is O, S, N—$R_1$; $Z_1$, $Z_3$, $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2; One of $Z_1$, $Z_3$, $Z_4$, $Z_5$, $Z_6$, $Z_7$ is the carbon atom to which the remainder of the molecule is attached.

172. $Z_2$ is O, S, N—$R_1$; $Z_1$, $Z_3$, $Z_4$, $Z_5$, $Z_6$, $Z_7$ are independently $CR_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2; One of $Z_1$, $Z_3$, $Z_4$, $Z_5$, $Z_6$, $Z_7$ is the carbon atom to which the remainder of the molecule is attached.

173. $Z_2$ is O, S, N—$R_1$; $Z_1$ is N; $Z_3$ is $CR_2$; $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2; One of $Z_3$, $Z_4$, $Z_5$, $Z_6$, $Z_7$ is the carbon atom to which the remainder of the molecule is attached.

174. $Z_2$ is O, S, N—$R_1$; $Z_1$, $Z_3$ are N; $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2; One of $Z_4$, $Z_5$, $Z_6$, $Z_7$ is the carbon atom to which the remainder of the molecule is attached.

175. $Z_3$ is O, S, N—$R_1$; $Z_1$, $Z_2$, $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2;One of $Z_1$, $Z_2$, $Z_4$, $Z_5$, $Z_6$, $Z_7$ is the carbon atom to which the remainder of the molecule is attached.

176. $Z_3$ is O, S, N—$R_1$; $Z_1$, $Z_2$, $Z_4$, $Z_5$, $Z_6$, $Z_7$ are independently $CR_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2; One of $Z_1$, $Z_2$, $Z_4$, $Z_5$, $Z_6$, $Z_7$ is the carbon atom to which the remainder of the molecule is attached.

177. $Z_3$ is O, S, N—$R_1$; $Z_1$ is N; $Z_2$ is $CR_2$; $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2; One of $Z_2$, $Z_4$, $Z_5$, $Z_6$, $Z_7$ is the carbon atom to which the remainder of the molecule is attached.

178. $Z_3$ is O, S, N—$R_1$; $Z_1$, $Z_2$ is N; $Z_4$, $Z_5$, $Z_6$, $Z_7$ are independently N, $CR_2$; $Y_1$, $Y_2$, $Y_3$, $Y_4$ are C; $W_1$, $W_2$ are independently N—$R_1$, O, S=(O)$_r$ (r=0–2), $CR_4R_4$; t=0–2; One of $Z_4$, $Z_5$, $Z_6$, $Z_7$ is the carbon atom to which the remainder of the molecule is attached.

179. $Z_1$, $Z_2$, $Z_3$, $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0–2), $CR_4R_4$; t=0–2; One of $Z_1$, $Z_2$, $Z_3$, $Z_4$, $Z_5$, $Z_6$, $Z_7$ is the carbon atom to which the remainder of the molecule is attached.

180. $Z_1$ is N; $Z_2$, $Z_3$ are independently $CR_2$; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0–2), $CR_4R_4$; t=0–2; One of $Z_2$, $Z_3$, $Z_4$, $Z_5$, $Z_6$, $Z_7$ is the carbon atom to which the remainder of the molecule is attached.

181. $Z_1$, $Z_2$ are N; $Z_3$ is $CR_2$; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0–2), $CR_4R_4$; t=0–2; One of $Z_3$, $Z_4$, $Z_5$, $Z_6$, $Z_7$ is the carbon atom to which the remainder of the molecule is attached.

182. $Z_1$, $Z_2$, $Z_3$ are N; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0–2), $CR_4R_4$; t=0–2; One of $Z_4$, $Z_5$, $Z_6$, $Z_7$ is the carbon atom to which the remainder of the molecule is attached.

183. $Z_2$ is N; $Z_1$, $Z_3$ are independently $CR_2$; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0–2), $CR_4R_4$; t=0–2; One of $Z_1$, $Z_3$, $Z_4$, $Z_5$, $Z_6$, $Z_7$ is the carbon atom to which the remainder of the molecule is attached.

184. $Z_2$, $Z_3$ are N; $Z_1$ is $CR_2$; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0–2), $CR_4R_4$; t=0–2; One of $Z_1$, $Z_4$, $Z_5$, $Z_6$, $Z_7$ is the carbon atom to which the remainder of the molecule is attached.

185. $Z_3$ is N; $Z_1$, $Z_2$ are independently $CR_2$; $Z_4$, $Z_5$, $Z_6$, $Z_7$ are independently N, $CR_2$; $Y_1$ is N; $Y_2$, $Y_3$, $Y_4$ are C; $W_1$, $W_2$ are independently N—$R_1$, O, S=(O)$_r$ (r=0–2), $CR_4R_4$; t=0–2; One of $Z_1$, $Z_2$, $Z_4$, $Z_5$, $Z_6$, $Z_7$ is the carbon atom to which the remainder of the molecule is attached.

186. $Z_1$, $Z_2$, $Z_3$, $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0–2), $CR_4R_4$; t=0–2; One of $Z_1$, $Z_2$, $Z_3$, $Z_4$, $Z_5$, $Z_6$, $Z_7$ is the carbon atom to which the remainder of the molecule is attached.

187. $Z_1$ is N; $Z_2$, $Z_3$ are independently $CR_2$; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0–2), $CR_4R_4$; t=0–2; One of $Z_2$, $Z_3$, $Z_4$, $Z_5$, $Z_6$, $Z_7$ is the carbon atom to which the remainder of the molecule is attached.

188. $Z_1$, $Z_2$ are N; $Z_3$ is $CR_2$; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0–2), $CR_4R_4$; t=0–2; One of $Z_3$, $Z_4$, $Z_5$, $Z_6$, $Z_7$ is the carbon atom to which the remainder of the molecule is attached.

189. $Z_1$, $Z_2$, $Z_3$ are N; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0–2), $CR_4R_4$; t=0–2; One of $Z_4$, $Z_5$, $Z_6$, $Z_7$ is the carbon atom to which the remainder of the molecule is attached.

190. $Z_2$ is N; $Z_1$, $Z_3$ are independently $CR_2$; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0–2), $CR_4R_4$; t=0–2; One of $Z_1$, $Z_3$, $Z_4$, $Z_5$, $Z_6$, $Z_7$ is the carbon atom to which the remainder of the molecule is attached.

191. $Z_2$, $Z_3$ are N; $Z_1$ is $CR_2$; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0–2), $CR_4R_4$; t=0–2;One of $Z_1$, $Z_4$, $Z_5$, $Z_6$, $Z_7$ is the carbon atom to which the remainder of the molecule is attached.

192. $Z_3$ is N; $Z_1$, $Z_2$ are independently $CR_2$; $Z_4$, $Z_5$, $Z_6$, $Z_7$ are independently N, $CR_2$; $Y_4$ is N; $Y_2$, $Y_3$, $Y_1$ are C; $W_1$, $W_2$ are independently N—$R_1$, O, S=(O)$_r$ (r=0–2), $CR_4R_4$; t=0–2; One of $Z_1$, $Z_2$, $Z_4$, $Z_5$, $Z_6$, $Z_7$ is the carbon atom to which the remainder of the molecule is attached.

The preferred embodiments of formula 9A are:

193. $Z_1$ is O, S, N—$R_1$; $Z_2$, $Z_3$ are independently $CR_2$; $Y_1$, $Y_4$ are C; $Y_2$, $Y_3$ are independently N, C, CH (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_2$, $Z_3$ is the carbon atom to which the remainder of the molecule is attached.

194. $Z_1$ is O, S, N—$R_1$; $Z_2$ is N; $Z_3$ is $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_3$ is the carbon atom to which the remainder of the molecule is attached.

195. $Z_1$ is O, S, N—$R_1$; $Z_3$ is N $Z_2$ is $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_2$ is the carbon atom to which the remainder of the molecule is attached.

196. $Z_2$ is O, S, N—$R_1$; $Z_1$, $Z_3$ are independently $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_2$, $Z_3$ is the carbon atom to which the remainder of the molecule is attached.

197. $Z_2$ is O, S, N—$R_1$; $Z_1$ is N; $Z_3$ is $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_3$ is the carbon atom to which the remainder of the molecule is attached.

198. $Z_2$ is O, S, N—$R_1$; $Z_3$ is N $Z_1$ is $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_1$ is the carbon atom to which the remainder of the molecule is attached.

199. $Z_3$ is O, S, N—$R_1$; $Z_1$, $Z_2$ are independently $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_1$, $Z_2$ is the carbon atom to which the remainder of the molecule is attached.

200. $Z_3$ is O, S, N—$R_1$; $Z_1$ is N; $Z_2$ is $CR_2$; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_2$ is the carbon atom to which the remainder of the molecule is attached.

201. $Z_3$ is O, S, N—$R_1$; $Z_1$ is $CH_2$; $Z_2$ is N; $Y_1$, $Y_4$ are C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_1$ is the carbon atom to which the remainder of the molecule is attached.

202. $Z_1$, $Z_2$, $Z_3$ are independently $CR_2$; $Y_1$ is N; $Y_4$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_1$, $Z_2$, $Z_3$ is the carbon atom to which the remainder of the molecule is attached.

203. $Z_1$ is N; $Z_2$, $Z_3$ are independently $CR_2$; $Y_1$ is N; $Y_4$ is C; $Y_2$, $Y_3$ are independently C, CH. N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_2$, $Z_3$ is the carbon atom to which the remainder of the molecule is attached.

204. $Z_1$, $Z_2$ is N; $Z_3$ is $CR_2$; $Y_1$ is N; $Y_4$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_3$ is the carbon atom to which the remainder of the molecule is attached.

205. $Z_1$, $Z_3$ are N; $Z_2$ is $CR_2$; $Y_1$ is N; $Y_4$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_2$ is the carbon atom to which the remainder of the molecule is attached.

206. $Z_1$, $Z_2$, $Z_3$ are independently $CR_2$; $Y_4$ is N; $Y_1$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_1$, $Z_2$, $Z_3$ is the carbon atom to which the remainder of the molecule is attached.

207. $Z_1$ is N; $Z_2$, $Z_3$ are independently $CR_2$; $Y_4$ is N; $Y_1$ is C; $Y_2$, $Y_3$ are independently C, CH. N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_2$, $Z_3$ is the carbon atom to which the remainder of the molecule is attached.

208. $Z_1$, $Z_2$ are N; $Z_3$ is $CR_2$; $Y_4$ is N; $Y_1$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_3$ is the carbon atom to which the remainder of the molecule is attached.

209. $Z_1$, $Z_3$ are N; $Z_2$ is $CR_2$; $Y_4$ is N; $Y_1$ is C; $Y_2$, $Y_3$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_2$ is the carbon atom to which the remainder of the molecule is attached.

The preferred embodiments of formula 9-B:

210. $Z_1$ is O, S, N—$R_1$; $Z_2$, $Z_3$ are independently $CR_2$; $Y_1$, $Y_2$ are C; $Y_3$, $Y_4$ are independently N, C, CH (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_2$, $Z_3$ is the carbon atom to which the remainder of the molecule is attached.

211. $Z_1$ is O, S, N—$R_1$; $Z_2$ is N; $Z_3$ is $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_3$ is the carbon atom to which the remainder of the molecule is attached.

212. $Z_1$ is O, S, N—$R_1$; $Z_3$ is N $Z_2$ is $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_2$ is the carbon atom to which the remainder of the molecule is attached.

213. $Z_2$ is O, S, N—$R_1$; $Z_1$, $Z_3$ are independently $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_2$, $Z_3$ is the carbon atom to which the remainder of the molecule is attached.

214. $Z_2$ is O, S, N—$R_1$; $Z_1$ is N; $Z_3$ is $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_3$ is the carbon atom to which the remainder of the molecule is attached.

215. $Z_2$ is O, S, N—$R_1$; $Z_3$ is N $Z_1$ is $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_1$ is the carbon atom to which the remainder of the molecule is attached.

216. $Z_3$ is O, S, N—$R_1$; $Z_1$, $Z_2$ are independently $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_1$, $Z_2$ is the carbon atom to which the remainder of the molecule is attached.

217. $Z_3$ is O, S, N—$R_1$; $Z_1$ is N; $Z_2$ is $CR_2$; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_2$ is the carbon atom to which the remainder of the molecule is attached.

218. $Z_3$ is O, S, N—$R_1$; $Z_1$ is $CH_2$; $Z_2$ is N; $Y_1$, $Y_2$ are C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_1$ is the carbon atom to which the remainder of the molecule is attached.

219. $Z_1$, $Z_2$, $Z_3$ are independently $CR_2$; $Y_1$ is N; $Y_2$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_1$, $Z_2$, $Z_3$ is the carbon atom to which the remainder of the molecule is attached.

220. $Z_1$ is N; $Z_2$, $Z_3$ are $CR_2$; $Y_1$ is N; $Y_2$ is C; $Y_3$, $Y_4$ are independently C, CH. N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_2$, $Z_3$ is the carbon atom to which the remainder of the molecule is attached.

221. $Z_1$, $Z_2$ are N; $Z_3$ is $CR_2$; $Y_1$ is N; $Y_2$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_3$ is the carbon atom to which the remainder of the molecule is attached.

222. $Z_1$, $Z_3$ are N; $Z_2$ is $CR_2$; $Y_1$ is N; $Y_2$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_2$ is the carbon atom to which the remainder of the molecule is attached.

223. $Z_1$, $Z_2$, $Z_3$ are independently $CR_2$; $Y_2$ is N; $Y_1$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_1$, $Z_2$, $Z_3$ is the carbon atom to which the remainder of the molecule is attached.

224. $Z_1$ is N; $Z_2$, $Z_3$ are independently $CR_2$; $Y_2$ is N; $Y_1$ is C; $Y_3$, $Y_4$ are independently C, CH. N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; One of $Z_2$, $Z_3$ is the carbon atom to which the remainder of the molecule is attached.

225. $Z_1$, $Z_2$ are N; $Z_3$ is $CR_2$; $Y_2$ is N; $Y_1$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_3$ is the carbon atom to which the remainder of the molecule is attached.

226. $Z_1$, $Z_3$ are N; $Z_2$ is $CR_2$; $Y_2$ is N; $Y_1$ is C; $Y_3$, $Y_4$ are independently C, CH, N (in between a double bond might be present); $W_1$, $W_2$, $W_3$, $W_4$, $W_5$ are independently N—$R_1$, O, S=(O)$_r$ (r=0–2), $CR_4R_4$; t=0–2; u=1–3; $Z_2$ is the carbon atom to which the remainder of the molecule is attached.

The preferred embodiments of formula 10-A:

227. $Z_1$, $Z_2$, $Z_3$, $Z_4$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_1$, $Z_2$, $Z_3$, $Z_4$, $Z_6$, $Z_7$, $Z_8$, $Z_9$ must be a carbon atom to which the remainder of the molecule is attached.

228. $Z_1$ is N; $Z_2$, $Z_3$, $Z_4$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_2$, $Z_3$, $Z_4$, $Z_6$, $Z_7$, $Z_8$, $Z_9$ must be a carbon atom to which the remainder of the molecule is attached.

229. $Z_1$, $Z_2$ are N; $Z_3$, $Z_4$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_3$, $Z_4$, $Z_6$, $Z_7$, $Z_8$, $Z_9$ must be a carbon atom to which the remainder of the molecule is attached.

230. $Z_1$, $Z_3$ are N; $Z_2$, $Z_4$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_2$, $Z_4$, $Z_6$, $Z_7$, $Z_8$, $Z_9$ must be a carbon atom to which the remainder of the molecule is attached.

231. $Z_1$, $Z_4$ are N; $Z_3$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_3$, $Z_6$, $Z_7$, $Z_8$, $Z_9$ must be a carbon atom to which the remainder of the molecule is attached.

232. $Z_1$ is N; $Z_2$, $Z_3$, $Z_4$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_2$, $Z_3$, $Z_4$, $Z_6$, $Z_7$, $Z_8$, $Z_9$ must be a carbon atom to which the remainder of the molecule is attached.

233. $Z_1$, $Z_2$ are N; $Z_3$, $Z_4$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_3$, $Z_4$, $Z_6$, $Z_7$, $Z_8$, $Z_9$ must be a carbon atom to which the remainder of the molecule is attached.

234. $Z_1$, $Z_3$ are N; $Z_2$, $Z_4$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_2$, $Z_4$, $Z_6$, $Z_7$, $Z_8$, $Z_9$ must be a carbon atom to which the remainder of the molecule is attached.

235. $Z_1$, $Z_4$ are N; $Z_2$, $Z_3$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_2$, $Z_3$, $Z_6$, $Z_7$, $Z_8$, $Z_9$ must be a carbon atom to which the remainder of the molecule is attached.

236. $Z_2$ is N; $Z_1$, $Z_3$, $Z_4$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_1$, $Z_3$, $Z_4$, $Z_6$, $Z_7$, $Z_8$, $Z_9$ must be a carbon atom to which the remainder of the molecule is attached.

237. $Z_2$, $Z_3$ are N; $Z_1$, $Z_4$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_1$, $Z_4$, $Z_6$, $Z_7$, $Z_8$, $Z_9$ must be a carbon atom to which the remainder of the molecule is attached.

238. $Z_2$ $Z_4$ are N; $Z_1$, $Z_3$, $Z_6$, $Z_7$, $Z_8$, $Z_9$ are independently $CR_2$; $Z_5$ is O, S, N—$R_1$; $Y_1$, $Y_2$, $Y_3$, $Y_4$ are C; one of $Z_1$, $Z_3$, $Z_6$, $Z_7$, $Z_8$, $Z_9$ must be a carbon atom to which the remainder of the molecule is attached.

239. $Z_2$ is N; $Z_1$, $Z_3$, $Z_4$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_1$, $Z_3$, $Z_4$, $Z_6$, $Z_7$, $Z_8$, $Z_9$ must be a carbon atom to which the remainder of the molecule is attached.

240. $Z_2$, $Z_3$ are N; $Z_1$, $Z_4$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_1$, $Z_4$, $Z_6$, $Z_7$, $Z_8$, $Z_9$ must be a carbon atom to which the remainder of the molecule is attached.

241. $Z_2$, $Z_4$ are N; $Z_1$, $Z_3$ are independently $CR_2$; $Z_6$, $Z_7$, $Z_8$, $Z_9$ are independently N, $CR_2$; $Z_5$ is O, S, N—$R_1$; $Y_1$, $Y_2$, $Y_3$, $Y_4$ are C; one of $Z_1$, $Z_3$, $Z_6$, $Z_7$, $Z_8$, $Z_9$ must be a carbon atom to which the remainder of the molecule is attached.

The preferred embodiments of formula 11-A:

242. $Z_1$, $Z_2$, $Z_3$, $Z_4$, $Z_6$, $Z_7$, $Z_8$, $Z_9$ are independently $CR_2$; $Z_5$, $Z_{10}$ are independently O, S, N—$R_1$; $Y_1$, $Y_2$, $Y_3$, $Y_4$ are C; Any one of $Z_1$, $Z_2$, $Z_3$, $Z_4$, $Z_6$, $Z_7$, $Z_8$, $Z_9$ must be a carbon atom to which the remainder of the molecule is attached.

243. $Z_1$, $Z_2$, $Z_3$, $Z_4$, $Z_6$, $Z_7$, $Z_8$, $Z_9$ are independently N, $CR_2$; $Z_5$, $Z_{10}$ are independently O, S, N—$R_1$; $Y_1$, $Y_2$, $Y_3$, $Y_4$ are C; Any one of $Z_1$, $Z_2$, $Z_3$, $Z_4$, $Z_6$, $Z_7$, $Z_8$, $Z_9$ must be a carbon atom to which the remainder of the molecule is attached.

The preferred embodiments of formula 11-B:

244. $Z_1$, $Z_2$, $Z_3$, $Z_4$, $Z_7$, $Z_8$, $Z_9$, $Z_{10}$ are independently $CR_2$; $Z_5$, $Z_6$ are independently N, $CR_2$; $Y_1$, $Y_2$, $Y_3$, $Y_4$ are C; Any one of $Z_1$, $Z_2$, $Z_3$, $Z_4$, $Z_7$, $Z_8$, $Z_9$, $Z_{10}$ must be a carbon atom to which the remainder of the molecule is attached.

245. $Z_1$, $Z_2$, $Z_3$, $Z_4$ are independently $CR_2$, N; $Z_5$, $Z_6$, $Z_7$, $Z_8$, $Z_9$, $Z_{10}$ are independently $CR_2$; $Y_1$, $Y_2$, $Y_3$, $Y_4$ are C; Any one of $Z_1$, $Z_2$, $Z_3$, $Z_4$, $Z_7$, $Z_8$, $Z_9$, $Z_{10}$ must be a carbon atom to which the remainder of the molecule is attached.

The preferred embodiments of formula 11-C:

246. $Z_1$, $Z_2$, $Z_3$, $Z_4$, $Z_6$, $Z_7$, $Z_8$, $Z_9$ are independently $CR_2$; $Y_1$ is N; $Y_2$ is C; Any one of $Z_1$, $Z_2$, $Z_3$, $Z_4$, $Z_6$, $Z_7$, $Z_8$, $Z_9$ must be a carbon atom to which the remainder of the molecule is attached.

247. $Z_1$, $Z_2$, $Z_3$, $Z_4$, $Z_7$, $Z_8$, $Z_9$ are independently $CR_2$; $Z_6$ is O, S, N—$R_1$; $Y_1$ is C; $Y_2$ is N; Any one of $Z_1$, $Z_2$, $Z_3$, $Z_4$, $Z_6$, $Z_7$, $Z_8$, $Z_9$ must be a carbon atom to which the remainder of the molecule is attached.

The preferred embodiments of formula 12-A:

248. $Z_1$, $Z_2$, $Z_3$, $Z_4$ are independently $CR_2$; $Z_5$ is O, S, N—$R_1$; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring. In the ring formed by $W_1$, $W_2$, $W_3$ one double bond might be present; t=1–4; $Y_1$, $Y_2$, $Y_3$, $Y_4$ are C; Any one of $Z_1$, $Z_2$, $Z_3$, $Z_4$ must be a carbon atom to which the remainder of the molecule is attached.

249. $Z_1$, $Z_2$, $Z_3$, $Z_4$ are independently $CR_2$; $Z_5$ is N, $CR_2$; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; In the ring formed by $W_1$, $W_2$, $W_3$ one double bond might be present; t=1–4; $Y_1$, $Y_2$, $Y_3$ are C; $Y_4$ is N; Any one of $Z_1$, $Z_2$, $Z_3$, $Z_4$ must be a carbon atom to which the remainder of the molecule is attached.

250. $Z_1$, $Z_2$, $Z_3$, $Z_4$ are independently $CR_2$; $Z_5$ is O, S. N; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; In the ring formed by $W_1$, $W_2$, $W_3$ one double bond might be present; t=1–3; $Y_1$, $Y_2$, $Y_3$ are C; $Y_4$ is N; Any one of $Z_1$, $Z_2$, $Z_3$, $Z_4$ must be a carbon atom to which the remainder of the molecule is attached.

251. $Z_1$ is N; $Z_2$, $Z_3$, $Z_4$ are independently $CR_2$; $Z_5$ is O, S, N—$R_1$; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring. In the ring formed by $W_1$, $W_2$, $W_3$ one double bond might be present; t=1–4; $Y_1$, $Y_2$, $Y_3$, $Y_4$ are C; Any one of $Z_2$, $Z_3$, $Z_4$ must be a carbon atom to which the remainder of the molecule is attached.

252. $Z_1$, $Z_2$ are N; $Z_3$, $Z_4$ are independently $CR_2$; $Z_5$ is O, S, N—$R_1$; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring. In the ring formed by $W_1$, $W_2$, $W_3$ one double bond might be present; t=1–4; $Y_1$, $Y_2$, $Y_3$, $Y_4$ are C; Any one of $Z_3$, $Z_4$ must be a carbon atom to which the remainder of the molecule is attached.

253. $Z_1$, $Z_3$ are N; $Z_2$, $Z_4$ are independently $CR_2$; $Z_5$ is O, S, N—$R_1$; $Z_1$, $Z_2$ are N; $Z_3$, $Z_4$ are independently $CR_2$; $Z_5$ is N, $CR_2$; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; In the ring formed by $W_1$, $W_2$, $W_3$ one double bond might be present; t=1–4; $Y_1$, $Y_2$, $Y_3$ are C; $Y_4$ is N; Any one of $Z_2$, $Z_4$ must be a carbon atom to which the remainder of the molecule is attached.

254. $Z_1$, $Z_4$ are N; $Z_2$, $Z_3$ are independently $CR_2$; $Z_5$ is O, S, N—$R_1$; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring. In the ring formed by $W_1$, $W_2$, $W_3$ one double bond might be present; t=1–4; $Y_1$, $Y_2$, $Y_3$, $Y_4$ are C; Any one of $Z_2$, $Z_3$ must be a carbon atom to which the remainder of the molecule is attached.

255. $Z_1$ is N; $Z_2$, $Z_3$, $Z_4$ are independently $CR_2$; $Z_5$ is N, $CR_2$; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; In the ring formed by $W_1$, $W_2$, $W_3$ one double bond might be present; t=1–4; $Y_1$, $Y_2$, $Y_3$ are C; $Y_4$ is N; Any one of $Z_2$, $Z_3$, $Z_4$ must be a carbon atom to which the remainder of the molecule is attached.

256. $Z_1$, $Z_3$ are N; $Z_2$, $Z_4$ are independently $CR_2$; $Z_5$ is N, $CR_2$; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; In the ring formed by $W_1$, $W_2$, $W_3$ one double bond might be present; t=1–4; $Y_1$, $Y_2$, $Y_3$ are C; $Y_4$ is N; Any one of $Z_2$, $Z_4$ must be a carbon atom to which the remainder of the molecule is attached.

257. $Z_1$, $Z_4$ are N; $Z_2$, $Z_3$ are independently $CR_2$; $Z_5$ is N, $CR_2$; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; In the ring formed by $W_1$, $W_2$, $W_3$ one double bond might be present; t=1–4; $Y_1$, $Y_2$, $Y_3$ are C; $Y_4$ is N; Any one of $Z_2$, $Z_3$ must be a carbon atom to which the remainder of the molecule is attached.

258. $Z_1$, $Z_2$ are N; $Z_3$, $Z_4$ are independently $CR_2$; $Z_5$ is O, S. N; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; In the ring formed by $W_1$, $W_2$, $W_3$ one double bond might be present; t=1–3; $Y_1$, $Y_2$, $Y_3$ are C; $Y_4$ is N; Any one of $Z_3$, $Z_4$ must be a carbon atom to which the remainder of the molecule is attached.

259. $Z_1$, $Z_3$ are N; $Z_2$, $Z_4$ are independently $CR_2$; $Z_5$ is O, S. N; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; In the ring formed by $W_1$, $W_2$, $W_3$ one double bond might be present; t=1–3; $Y_1$, $Y_2$, $Y_3$ are C; $Y_4$ is N; Any one of $Z_2$, $Z_4$ must be a carbon atom to which the remainder of the molecule is attached.

260. $Z_1$, $Z_4$ are N; $Z_2$, $Z_3$ are independently $CR_2$; $Z_5$ is O, S, N; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–3; $Y_1$, $Y_2$, $Y_3$ are C; $Y_4$ is N; Any one of $Z_2$, $Z_3$ must be a carbon atom to which the remainder of the molecule is attached.

261. $Z_2$ is N; $Z_1$, $Z_3$, $Z_4$ are independently $CR_2$; $Z_5$ is O, S, N—$R_1$; $W_1$, $W_2$, $W_3$ are independently $CR_4R_4$, S(O)r (r=0–2), O, N—$R_1$ with the proviso that no S—S, S—O or O—O bond formation can occur to form a saturated ring. In the ring formed by $W_1$, $W_2$, $W_3$ one double bond might be present; t=1–4; $Y_1$, $Y_2$, $Y_3$, $Y_4$ are C; Any one of $Z_1$, $Z_3$, $Z_4$ must be a carbon atom to which the remainder of the molecule is attached.

262. $Z_2$, $Z_3$ are N; $Z_1$, $Z_4$ are independently $CR_2$; $Z_5$ is O, S, N—$R_1$; $W_1$, $W_2$, $W_3$ are independently $CR_4R_4$, S(O)r (r=0–2), O, N—$R_1$ with the proviso that no S—S, S—O or O—O bond formation can occur to form a saturated ring. In the ring formed by $W_1$, $W_2$, $W_3$ one double bond might be present; t=1–4; $Y_1$, $Y_2$, $Y_3$, $Y_4$ are C; Any one of $Z_1$, $Z_4$ must be a carbon atom to which the remainder of the molecule is attached.

263. $Z_2$, $Z_4$ are N; $Z_1$, $Z_3$ are independently $CR_2$; $Z_5$ is O, S, N—$R_1$; $W_1$, $W_2$, $W_3$ are independently $CR_4R_4$, S(O)r (r=0–2), O, N—$R_1$ with the proviso that no S—S, S—O or O—O bond formation can occur to form a saturated ring. In the ring formed by $W_1$, $W_2$, $W_3$ one double bond might be present; t=1–4; $Y_1$, $Y_2$, $Y_3$, $Y_4$ are C; Any one of $Z_1$, $Z_3$ must be a carbon atom to which the remainder of the molecule is attached.

264. $Z_2$ is N; $Z_1$, $Z_3$, $Z_4$ are independently $CR_2$; $Z_5$ is N, $CR_2$; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–4; $Y_1$, $Y_2$, $Y_3$ are C; $Y_4$ is N; Any one of $Z_2$, $Z_3$, $Z_4$ must be a carbon atom to which the remainder of the molecule is attached.

265. $Z_2$, $Z_3$ are N; $Z_1$, $Z_4$ are independently $CR_2$; $Z_5$ is N, $CR_2$; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–4; $Y_1$, $Y_2$, $Y_3$ are C; $Y_4$ is N; Any one of $Z_1$, $Z_4$ must be a carbon atom to which the remainder of the molecule is attached.

266. $Z_2$, $Z_4$ are N; $Z_1$, $Z_3$ are independently $CR_2$; $Z_5$ is N, $CR_2$; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–4; $Y_1$, $Y_2$, $Y_3$ are C; $Y_4$ is N; Any one of $Z_1$, $Z_3$ must be a carbon atom to which the remainder of the molecule is attached.

267. $Z_2$ is N; $Z_1$, $Z_3$, $Z_4$ are independently $CR_2$; $Z_5$ is O, S, N; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–3; $Y_1$, $Y_2$, $Y_3$ are C; $Y_4$ is N; Any one of $Z_1$, $Z_3$, $Z_4$, must be a carbon atom to which the remainder of the molecule is attached.

268. $Z_2$, $Z_3$ are N; $Z_1$, $Z_4$ are independently $CR_2$; $Z_5$ is O, S, N; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–3; $Y_1$, $Y_2$, $Y_3$ are C; $Y_4$ is N; Any one of $Z_1$, $Z_4$ must be a carbon atom to which the remainder of the molecule is attached.

269. $Z_2$, $Z_4$ are N; $Z_1$, $Z_3$ are independently $CR_2$; $Z_5$ is O, S, N; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–3; $Y_1$, $Y_2$, $Y_3$ are C; $Y_4$ is N; Any one of $Z_1$, $Z_3$ must be a carbon atom to which the remainder of the molecule is attached.

270. $Z_3$ is N; $Z_1$, $Z_2$, $Z_4$ are independently $CR_2$; $Z_5$ is O, S, N—$R_1$; $W_1$, $W_2$, $W_3$ are independently $CR_4R_4$, S(O)r (r=0–2), O, N—$R_1$ with the proviso that no S—S, S—O or O—O bond formation can occur to form a saturated ring. In the ring formed by $W_1$, $W_2$, $W_3$ one double bond might be present; t=1–4; $Y_1$, $Y_2$, $Y_3$, $Y_4$ are C; Any one of $Z_1$, $Z_2$, $Z_4$ must be a carbon atom to which the remainder of the molecule is attached.

271. $Z_3$, $Z_4$ are N; $Z_1$, $Z_4$ are independently $CR_2$; $Z_5$ is O, S, N—$R_1$; $W_1$, $W_2$, $W_3$ are independently $CR_4R_4$, S(O)r (r=0–2), O, N—$R_1$ with the proviso that no S—S, S—O or O—O bond formation can occur to form a saturated ring. In the ring formed by $W_1$, $W_2$, $W_3$ one double bond might be present; t=1–4; $Y_1$, $Y_2$, $Y_3$, $Y_4$ are C; Any one of $Z_1$, $Z_2$ must be a carbon atom to which the remainder of the molecule is attached.

272. $Z_3$ is N; $Z_1$, $Z_3$, $Z_4$ are independently $CR_2$; $Z_5$ is N, $CR_2$; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–4; $Y_1$, $Y_2$, $Y_3$ are C; $Y_4$ is N; Any one of $Z_1$, $Z_2$, $Z_4$ must be a carbon atom to which the remainder of the molecule is attached.

273. $Z_3$, $Z_4$ are N; $Z_1$, $Z_2$ are independently $CR_2$; $Z_5$ is N, $CR_2$; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–4; $Y_1$, $Y_2$, $Y_3$ are C; $Y_4$ is N; Any one of $Z_1$, $Z_2$ must be a carbon atom to which the remainder of the molecule is attached.

274. $Z_3$ is N; $Z_1$, $Z_3$, $Z_4$ are independently $CR_2$; $Z_5$ is O, S, N; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–3; $Y_1$, $Y_2$, $Y_3$ are C; $Y_4$ is N; Any one of $Z_1$, $Z_2$, $Z_4$ must be a carbon atom to which the remainder of the molecule is attached.

275. $Z_3$, $Z_4$ are N; $Z_1$, $Z_4$ are independently $CR_2$; $Z_5$ is O, S, N; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–3; $Y_1$, $Y_2$, $Y_3$ are C; $Y_4$ is N; Any one of $Z_1$, $Z_2$ must be a carbon atom to which the remainder of the molecule is attached.

276. $Z_1$, $Z_2$, $Z_3$ are independently $CR_2$; $Z_4$ is N; $Z_5$ is O, S, N—$R_1$; $W_1$, $W_2$, $W_3$ are independently $CR_4R_4$, S(O)r (r=0–2), O, N—$R_1$ with the proviso that no S—S, S—O or O—O bond formation can occur to form a saturated ring. In the ring formed by $W_1$, $W_2$, $W_3$ one double bond might be present; t=1–4; $Y_1$, $Y_2$, $Y_3$, $Y_4$ are C; Any one of $Z_1$, $Z_2$, $Z_3$, must be a carbon atom to which the remainder of the molecule is attached.

277. $Z_1$, $Z_2$, $Z_3$ are independently $CR_2$; $Z_4$ is N; $Z_5$ is N, $CR_2$; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–4; $Y_1$, $Y_2$, $Y_3$ are C; $Y_4$ is N; Any one of $Z_1$, $Z_2$, $Z_3$ must be a carbon atom to which the remainder of the molecule is attached.

278. $Z_1$, $Z_2$, $Z_3$ are independently $CR_2$; $Z_4$ is N; $Z_5$ is O, S. N; $W_1$, $W_2$, $W_3$ are independently $CR_4R_4$, S(O)r (r=0–2), O, N—$R_1$ with the proviso that no S—S, S—O or O—O bond formation can occur to form a saturated ring; In the ring formed by $W_1$, $W_2$, $W_3$ one double bond might be present; t=1–3; $Y_1$, $Y_2$, $Y_3$ are C; $Y_4$ is N; Any one of $Z_1$, $Z_2$, $Z_3$, $Z_4$ must be a carbon atom to which the remainder of the molecule is attached.

The preferred embodiments of formula 12-B:

279. $Z_1$, $Z_2$, $Z_3$, $Z_4$ are independently $CR_2$; $Z_5$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_3$, $Z_4$ must be a carbon atom to which the remainder of the molecule is attached.

280. $Z_1$ is N; $Z_2$, $Z_3$, $Z_4$ are independently $CR_2$; $Z_5$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_2$, $Z_3$, $Z_4$ must be a carbon atom to which the remainder of the molecule is attached.

281. $Z_1$, $Z_2$ are N; $Z_3$, $Z_4$ are independently $CR_2$; $Z_5$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_3$, $Z_4$ must be a carbon atom to which the remainder of the molecule is attached.

282. $Z_1$, $Z_3$ are N; $Z_2$, $Z_4$ are independently $CR_2$; $Z_5$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_2$, $Z_4$ must be a carbon atom to which the remainder of the molecule is attached.

283. $Z_2$ is N; $Z_1$, $Z_3$, $Z_4$ are independently $CR_2$; $Z_5$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_3$, $Z_4$ must be a carbon atom to which the remainder of the molecule is attached.

284. $Z_2$, $Z_3$ are N; $Z_1$, $Z_4$ are independently $CR_2$; $Z_5$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_4$ must be a carbon atom to which the remainder of the molecule is attached.

285. $Z_3$ is N; $Z_1$, $Z_2$, $Z_4$ are independently $CR_2$; $Z_5$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_4$ must be a carbon atom to which the remainder of the molecule is attached.

286. $Z_1$, $Z_2$, $Z_3$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_3$, $Z_5$ must be a carbon atom to which the remainder of the molecule is attached.

287. $Z_1$ is N; $Z_2$, $Z_3$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_2$, $Z_3$, $Z_5$ must be a carbon atom to which the remainder of the molecule is attached.

288. $Z_1$, $Z_2$ are N; $Z_3$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_3$, $Z_5$ must be a carbon atom to which the remainder of the molecule is attached.

289. $Z_1$, $Z_3$ are N; $Z_2$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_2$, $Z_5$ must be a carbon atom to which the remainder of the molecule is attached.

290. $Z_2$ is N; $Z_1$, $Z_3$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_3$, $Z_5$ must be a carbon atom to which the remainder of the molecule is attached.

291. $Z_2$, $Z_3$ are N; $Z_1$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_5$ must be a carbon atom to which the remainder of the molecule is attached.

292. $Z_3$ is N; $Z_1$, $Z_2$, $Z_5$ are independently $CR_2$; $Z_4$ is O, S, N—$R_1$; $Y_1$, $Y_2$, $Y_3$, $Y_4$ are C; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_5$ must be a carbon atom to which the remainder of the molecule is attached.

293. $Z_1$, $Z_2$, $Z_3$, $Z_4$, $Z_5$ are independently $CR_2$; $Y_1$, $Y_2$, $Y_3$ are C; $Y_4$ is N; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_3$, $Z_4$ must be a carbon atom to which the remainder of the molecule is attached.

294. $Z_1$ is N; $Z_2$, $Z_3$, $Z_4$, $Z_5$ are independently $CR_2$; $Y_1$, $Y_2$, $Y_3$ are C; $Y_4$ is N; $W_1$, $W_2$ are independently $CR_4R_4$, S(O)r (r=0–2), O, N—$R_1$ with the proviso that no S—S, S—O or O—O bond formation can occur to form a saturated ring; t=1–3. Any one of $Z_2$, $Z_3$, $Z_4$ must be a carbon atom to which the remainder of the molecule is attached.

295. $Z_1$, $Z_2$ are N; $Z_3$, $Z_4$, $Z_5$ are independently $CR_2$; $Y_1$, $Y_2$, $Y_3$ are C; $Y_4$ is N; $W_1$, $W_2$ are independently $CR_4R_4$, $S(O)r$ (r=0–2), O, N—$R_1$ with the proviso that no S—S, S—O or O—O bond formation can occur to form a saturated ring; t=1–3. Any one of $Z_3$, $Z_4$ must be a carbon atom to which the remainder of the molecule is attached.

296. $Z_1$, $Z_3$ are N; $Z_2$, $Z_4$, $Z_5$ are independently $CR_2$; $Y_1$, $Y_2$, $Y_3$ are C; $Y_4$ is N; $W_1$, $W_2$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_4$, $Z_5$ must be a carbon atom to which the remainder of the molecule is attached.

297. $Z_2$ is N; $Z_1$, $Z_3$, $Z_4$, $Z_5$ are independently $CR_2$; $Y_1$, $Y_2$, $Y_3$ are C; $Y_4$ is N; $W_1$, $W_2$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$ must be a carbon atom to which the remainder of the molecule is attached.

298. $Z_2$, $Z_3$ are N; $Z_1$, $Z_4$, $Z_5$ are independently $CR_2$; $Y_1$, $Y_2$, $Y_3$ are C; $Y_4$ is N; $W_1$, $W_2$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_4$, $Z_5$ must be a carbon atom to which the remainder of the molecule is attached.

299. $Z_3$ is N; $Z_1$, $Z_2$, $Z_4$, $Z_5$ are independently $CR_2$; $Y_1$, $Y_2$, $Y_3$ are C; $Y_4$ is N; $W_1$, $W_2$ are independently $CR_4R_4$, $S(O)r$ (r=0–2), O, N—$R_1$ with the proviso that no S—S, S—O or O—O bond formation can occur to form a saturated ring; t=1–3. Any one Of $Z_1$, $Z_2$, $Z_4$, $Z_5$ must be a carbon atom to which the remainder of the molecule is attached.

The preferred embodiments of formula 13-A:

300. $Z_1$, $Z_2$, $Z_3$, $Z_4$, $Z_5$, $Z_6$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$, $Z_4$, $Z_5$, $Z_6$ must be a carbon atom to which the remainder of the molecule is attached.

301. $Z_1$ is N; $Z_2$, $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_4$, $Z_5$, $Z_6$ must be a carbon atom to which the remainder of the molecule is attached.

302. $Z_1$, $Z_2$ are N; $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_3$, $Z_4$, $Z_5$, $Z_6$ must be a carbon atom to which the remainder of the molecule is attached.

303. $Z_1$, $Z_3$ are N; $Z_2$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_4$, $Z_5$, $Z_6$ must be a carbon atom to which the remainder of the molecule is attached.

304. $Z_1$, $Z_4$ are N; $Z_2$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_5$, $Z_6$ must be a carbon atom to which the remainder of the molecule is attached.

305. $Z_1$, $Z_5$ are N; $Z_2$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_4$, $Z_6$ must be a carbon atom to which the remainder of the molecule is attached.

306. $Z_1$, $Z_6$ are N; $Z_2$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_4$, $Z_5$ must be a carbon atom to which the remainder of the molecule is attached.

307. $Z_2$ is N; $Z_1$, $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_5$, $Z_6$ must be a carbon atom to which the remainder of the molecule is attached.

308. $Z_2$, $Z_3$ are N; $Z_1$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_4$, $Z_5$, $Z_6$ must be a carbon atom to which the remainder of the molecule is attached.

309. $Z_2$, $Z_4$ are N; $Z_1$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_5$, $Z_6$ must be a carbon atom to which the remainder of the molecule is attached.

310. $Z_2$, $Z_5$ are N; $Z_1$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_6$ must be a carbon atom to which the remainder of the molecule is attached.

311. $Z_2$, $Z_5$ are N; $Z_1$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_6$ must be a carbon atom to which the remainder of the molecule is attached.

312. $Z_2$, $Z_6$ are N; $Z_1$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_5$ must be a carbon atom to which the remainder of the molecule is attached.

313. $Z_3$ is N; $Z_1$, $Z_2$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_4$, $Z_5$, $Z_6$ must be a carbon atom to which the remainder of the molecule is attached.

314. $Z_3$, $Z_4$ are N; $Z_1$, $Z_2$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_5$, $Z_6$ must be a carbon atom to which the remainder of the molecule is attached.

315. $Z_3$, $Z_5$ are N; $Z_1$, $Z_2$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_4$, $Z_6$ must be a carbon atom to which the remainder of the molecule is attached.

316. $Z_3$, $Z_6$ are N; $Z_1$, $Z_2$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_4$, $Z_5$ must be a carbon atom to which the remainder of the molecule is attached.

317. $Z_4$ is N; $Z_1$, $Z_2$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one Of $Z_1$, $Z_2$, $Z_3$, $Z_5$, $Z_6$ must be a carbon atom to which the remainder of the molecule is attached.

318. $Z_4$, $Z_5$ are N; $Z_1$, $Z_2$, $Z_3$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$, $Z_5$, $Z_6$ must be a carbon atom to which the remainder of the molecule is attached.

319. $Z_5$ is N; $Z_1$, $Z_2$, $Z_3$, $Z_4$, $Z_6$ are independently $CR_2$; $Y_1$, $Y_2$, $Y_3$, $Y_4$ are C; $W_1$, $W_2$ $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$, $Z_4$, $Z_6$ must be a carbon atom to which the remainder of the molecule is attached.

320. $Z_5$, $Z_6$ are N; $Z_1$, $Z_2$, $Z_3$, $Z_4$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$, $Z_4$ must be a carbon atom to which the remainder of the molecule is attached.

321. $Z_6$ is N; $Z_1$, $Z_2$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$. $Z_4$, $Z_5$ must be a carbon atom to which the remainder of the molecule is attached.

The preferred embodiments of formula 13-B:

322. $Z_1$, $Z_2$, $Z_3$, $Z_4$, $Z_5$, $Z_6$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$, $Z_4$, $Z_5$, $Z_6$ must be a carbon atom to which the remainder of the molecule is attached.

323. $Z_1$ is N; $Z_2$, $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_4$, $Z_5$, $Z_6$ must be a carbon atom to which the remainder of the molecule is attached.

324. $Z_1$, $Z_2$ are N; $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_3$, $Z_4$, $Z_5$, $Z_6$ must be a carbon atom to which the remainder of the molecule is attached.

325. $Z_1$, $Z_3$ are N; $Z_2$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_5$, $Z_6$ must be a carbon atom to which the remainder of the molecule is attached.

326. $Z_1$, 4 are N; $Z_2$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_5$, $Z_6$ must be a carbon atom to which the remainder of the molecule is attached.

327. $Z_1$, $Z_5$ are N; $Z_2$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_4$, $Z_6$ must be a carbon atom to which the remainder of the molecule is attached.

328. $Z_1$, $Z_6$ are N; $Z_2$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_4$, $Z_5$ must be a carbon atom to which the remainder of the molecule is attached.

329. $Z_2$ is N; $Z_1$, $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_5$, $Z_6$ must be a carbon atom to which the remainder of the molecule is attached.

330. $Z_2$, $Z_3$ are N; $Z_1$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_4$, $Z_5$, $Z_6$ must be a carbon atom to which the remainder of the molecule is attached.

331. $Z_2$, $Z_4$ are N; $Z_1$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_5$, $Z_6$ must be a carbon atom to which the remainder of the molecule is attached.

332. $Z_2$, $Z_5$ are N; $Z_1$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_6$ must be a carbon atom to which the remainder of the molecule is attached.

333. $Z_2$, $Z_5$ are N; $Z_1$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_6$ must be a carbon atom to which the remainder of the molecule is attached.

334. $Z_2$, $Z_6$ are N; $Z_1$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_5$ must be a carbon atom to which the remainder of the molecule is attached.

335. $Z_3$ is N; $Z_1$, $Z_2$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_4$, $Z_5$, $Z_6$ must be a carbon atom to which the remainder of the molecule is attached.

336. $Z_3$, $Z_4$ are N; $Z_1$, $Z_2$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_5$, $Z_6$ must be a carbon atom to which the remainder of the molecule is attached.

337. $Z_3$, $Z_5$ are N; $Z_1$, $Z_2$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_4$, $Z_6$ must be a carbon atom to which the remainder of the molecule is attached.

338. $Z_3$, $Z_6$ are N; $Z_1$, $Z_2$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_4$, $Z_5$ must be a carbon atom to which the remainder of the molecule is attached.

339. $Z_4$ is N; $Z_1$, $Z_2$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$, $Z_5$, $Z_6$ must be a carbon atom to which the remainder of the molecule is attached.

340. $Z_4$, $Z_5$ are N; $Z_1$, $Z_2$, $Z_3$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$, $Z_6$ must be a carbon atom to which the remainder of the molecule is attached.

341. $Z_5$ is N; $Z_1$, $Z_2$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$, $Z_4$, $Z_6$ must be a carbon atom to which the remainder of the molecule is attached.

342. $Z_5$, $Z_6$ are N; $Z_1$, $Z_2$, $Z_3$, $Z_4$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$, $Z_4$ must be a carbon atom to which the remainder of the molecule is attached.

343. $Z_6$ is N; $Z_1$, $Z_2$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$, $Z_4$, $Z_5$ must be a carbon atom to which the remainder of the molecule is attached.

The preferred embodiments of formula 13-C:

344. $Z_1$, $Z_2$, $Z_3$, $Z_4$, $Z_5$, $Z_6$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_3$, $Z_4$, $Z_5$, $Z_6$ must be a carbon atom to which the remainder of the molecule is attached.

345. $Z_1$ is N; $Z_2$, $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_4$, $Z_5$, $Z_6$ must be a carbon atom to which the remainder of the molecule is attached.

346. $Z_1$, $Z_2$ are N; $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_3$, $Z_4$, $Z_5$, $Z_6$ must be a carbon atom to which the remainder of the molecule is attached.

347. $Z_1$, $Z_3$ are N; $Z_2$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_4$, $Z_5$, $Z_6$ must be a carbon atom to which the remainder of the molecule is attached.

348. $Z_1$, $Z_4$ are N; $Z_2$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_5$, $Z_6$ must be a carbon atom to which the remainder of the molecule is attached.

349. $Z_1$, $Z_5$ are N; $Z_2$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_4$, $Z_6$ must be a carbon atom to which the remainder of the molecule is attached.

350. $Z_1$, $Z_6$ are N; $Z_2$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_4$, $Z_5$ must be a carbon atom to which the remainder of the molecule is attached.

351. $Z_2$ is N; $Z_1$, $Z_3$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_5$, $Z_6$ must be a carbon atom to which the remainder of the molecule is attached.

352. $Z_2$, $Z_3$ are N; $Z_1$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_4$, $Z_5$, $Z_6$ must be a carbon atom to which the remainder of the molecule is attached.

353. $Z_2$, $Z_4$ are N; $Z_1$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_3$, $Z_5$, $Z_6$ must be a carbon atom to which the remainder of the molecule is attached.

354. $Z_2$, $Z_5$ are N; $Z_1$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_3$, $Z_4$, $Z_6$ must be a carbon atom to which the remainder of the molecule is attached.

355. $Z_2$, $Z_5$ are N; $Z_1$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_3$, $Z_4$, $Z_6$ must be a carbon atom to which the remainder of the molecule is attached.

356. $Z_2$, $Z_6$ are N; $Z_1$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_3$, $Z_4$, $Z_5$ must be a carbon atom to which the remainder of the molecule is attached.

357. $Z_3$ is N; $Z_1$, $Z_2$, $Z_4$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_4$, $Z_5$, $Z_6$ must be a carbon atom to which the remainder of the molecule is attached.

358. $Z_3$, $Z_4$ are N; $Z_1$, $Z_2$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_5$, $Z_6$ must be a carbon atom to which the remainder of the molecule is attached.

359. $Z_3$, $Z_5$ are N; $Z_1$, $Z_2$, $Z_4$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_4$, $Z_6$ must be a carbon atom to which the remainder of the molecule is attached.

360. $Z_3$, $Z_6$ are N; $Z_1$, $Z_2$, $Z_4$, $Z_5$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_4$, $Z_5$ must be a carbon atom to which the remainder of the molecule is attached.

361. $Z_4$ is N; $Z_1$, $Z_2$, $Z_3$, $Z_5$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_3$, $Z_5$, $Z_6$ must be a carbon atom to which the remainder of the molecule is attached.

362. $Z_4$, $Z_5$ are N; $Z_1$, $Z_2$, $Z_3$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_3$, $Z_5$, $Z_6$ must be a carbon atom to which the remainder of the molecule is attached.

363. $Z_5$ is N; $Z_1$, $Z_2$, $Z_3$, $Z_4$, $Z_6$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_3$, $Z_4$, $Z_6$ must be a carbon atom to which the remainder of the molecule is attached.

364. $Z_5$, $Z_6$ are N; $Z_1$, $Z_2$, $Z_4$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_3$, $Z_4$ must be a carbon atom to which the remainder of the molecule is attached.

365. $Z_6$ is N; $Z_1$, $Z_2$, $Z_3$, $Z_4$, $Z_5$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_1$, $Z_2$, $Z_3$, $Z_4$, $Z_5$ must be a carbon atom to which the remainder of the molecule is attached.

The preferred embodiments of formula 14-A and 14-B:

366. $Z_1$ is N; $Z_2$, $Z_3$, $Z_4$, $Z_5$, $Z_6$, $Z_7$, $Z_8$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_2$, $Z_3$, $Z_4$, $Z_5$, $Z_6$, $Z_7$, $Z_8$ must be a carbon atom to which the remainder of the molecule is attached.

367. $Z_1$, $Z_2$ are N; $Z_3$, $Z_4$, $Z_5$, $Z_6$, $Z_7$, $Z_8$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_3$, $Z_4$, $Z_5$, $Z_6$, $Z_7$, $Z_8$ must be a carbon atom to which the remainder of the molecule is attached.

368. $Z_1$, $Z_3$ are N; $Z_2$, $Z_4$, $Z_5$, $Z_6$, $Z_7$, $Z_8$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_2$, $Z_4$, $Z_5$, $Z_6$, $Z_7$, $Z_8$ must be a carbon atom to which the remainder of the molecule is attached.

369. $Z_1$, $Z_4$ are N; $Z_2$, $Z_3$, $Z_5$, $Z_6$, $Z_7$, $Z_8$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_2$, $Z_3$, $Z_5$, $Z_6$, $Z_7$, $Z_8$ must be a carbon atom to which the remainder of the molecule is attached.

370. $Z_1$, $Z_2$ are N; $Z_3$, $Z_4$, $Z_5$, $Z_6$, $Z_7$, $Z_8$ are independently $CR_2$; $Y_1$, $Y_2$, $Y_3$, $Y_4$ are C; $W_1$, $W_2$, $W_3$ are independently $CR_4R_4$, S(O)r (r=0–2), O, N—$R_1$ with the proviso that no S—S, S—O or O—O bond formation can occur to form a saturated ring; t=1–3. Any one of $Z_3$, $Z_4$, $Z_5$, $Z_6$, $Z_7$, $Z_8$ must be a carbon atom to which the remainder of the molecule is attached.

371. $Z_1$ is N; $Z_2$, $Z_3$, $Z_4$ are independently $CR_2$; $Z_5$, $Z_6$, $Z_7$, $Z_8$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_4$, $Z_5$, $Z_6$, $Z_7$, $Z_8$ must be a carbon atom to which the remainder of the molecule is attached.

372. $Z_1$, $Z_2$ are N; $Z_3$, $Z_4$ are independently $CR_2$; $Z_5$, $Z_6$, $Z_7$, $Z_8$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_3$, $Z_4$, $Z_5$, $Z_6$, $Z_7$, $Z_8$ must be a carbon atom to which the remainder of the molecule is attached.

373. $Z_1$, $Z_3$ are N; $Z_2$, $Z_4$ are independently $CR_2$; $Z_5$, $Z_6$, $Z_7$, $Z_8$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_4$, $Z_5$, $Z_6$, $Z_7$, $Z_8$ must be a carbon atom to which the remainder of the molecule is attached.

374. $Z_1$, $Z_4$ are N; $Z_2$, $Z_3$ are independently $CR_2$; $Z_5$, $Z_6$, $Z_7$, $Z_8$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_2$, $Z_3$, $Z_5$, $Z_6$, $Z_7$, $Z_8$ must be a carbon atom to which the remainder of the molecule is attached.

375. $Z_1$, $Z_2$ are N; $Z_3$, $Z_4$ are independently $CR_2$; $Z_5$, $Z_6$, $Z_7$, $Z_8$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_3$, $Z_4$, $Z_5$, $Z_6$, $Z_7$, $Z_8$ must be a carbon atom to which the remainder of the molecule is attached.

376. $Z_2$ is N; $Z_1$, $Z_3$, $Z_4$, $Z_5$, $Z_6$, $Z_7$, $Z_8$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_5$, $Z_6$, $Z_7$, $Z_8$ must be a carbon atom to which the remainder of the molecule is attached.

377. $Z_2$, $Z_3$ are N; $Z_1$, $Z_4$, $Z_5$, $Z_6$, $Z_7$, $Z_8$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_4$, $Z_5$, $Z_6$, $Z_7$, $Z_8$ must be a carbon atom to which the remainder of the molecule is attached.

378. $Z_2$, $Z_4$ are N; $Z_1$, $Z_3$, $Z_5$, $Z_6$, $Z_7$, $Z_8$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_5$, $Z_6$, $Z_7$, $Z_8$ must be a carbon atom to which the remainder of the molecule is attached.

379. $Z_2$ is N; $Z_1$, $Z_3$, $Z_4$ are independently $CR_2$; $Z_5$, $Z_6$, $Z_7$, $Z_8$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_5$, $Z_6$, $Z_7$, $Z_8$ must be a carbon atom to which the remainder of the molecule is attached.

380. $Z_2$, $Z_3$ are N; $Z_1$, $Z_4$ are independently $CR_2$; $Z_5$, $Z_6$, $Z_7$, $Z_8$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_4$, $Z_5$, $Z_6$, $Z_7$, $Z_8$ must be a carbon atom to which the remainder of the molecule is attached.

381. $Z_2$, $Z_4$ are N; $Z_1$, $Z_3$ are independently $CR_2$; $Z_5$, $Z_6$, $Z_7$, $Z_8$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_5$, $Z_6$, $Z_7$, $Z_8$ must be a carbon atom to which the remainder of the molecule is attached.

382. $Z_3$ is N; $Z_1$, $Z_2$, $Z_4$, $Z_5$, $Z_6$, $Z_7$, $Z_8$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_4$, $Z_5$, $Z_6$, $Z_7$, $Z_8$ must be a carbon atom to which the remainder of the molecule is attached.

383. $Z_3$, $Z_4$ are N; $Z_1$, $Z_2$, $Z_5$, $Z_6$, $Z_7$, $Z_8$ are independently $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_2$, $Z_5$, $Z_6$, $Z_7$, $Z_8$ must be a carbon atom to which the remainder of the molecule is attached.

384. $Z_4$ is N; $Z_1$, $Z_3$, $Z_4$ are independently $CR_2$; $Z_5$, $Z_6$, $Z_7$, $Z_8$ are independently N, $CR_2$; $Y_1$, $Y_2$, $Y_3$, $Y_4$ are C; $W_1$, $W_2$, $W_3$ are independently $CR_4R_4$, $S(O)r$ (r=0–2), O, N—$R_1$ with the proviso that no S—S, S—O or O—O bond formation can occur to form a saturated ring; t=1–3. Any one of $Z_1$, $Z_3$, $Z_4$, $Z_5$, $Z_6$, $Z_7$, $Z_8$ must be a carbon atom to which the remainder of the molecule is attached.

The preferred embodiments of formula 15-A:

385. $Z_1$ is N; $Z_2$, $Z_3$, $Z_4$ are independently $CR_2$; $Y_1$, $Y_2$ are C; $Y_3$, $Y_4$ are independently CH, N; $W_1$ is O, $S(O)r$ (r=0–2), $CR_4R_4$, N—$R_1$, a bond; $W_2$ is O, $S(O)r$ (r=0–2), $CR_4R_4$, N—$R_1$; t=0–2; $W_3$, $W_4$, $W_5$ are independently O, $S(O)r$ (r=0–2), $CR_4R_4$, N—$R_1$ with the proviso that no S—S, S—O or O—O bond formation can occur to form a saturated ring; u=1–3; Any one of $Z_2$, $Z_3$, $Z_4$ must be a carbon atom to which the remainder of the molecule is attached.

386. $Z_1$, $Z_2$ are N; $Z_3$, $Z_4$ are independently $CR_2$; $Y_1$, $Y_2$ are C; $Y_3$, $Y_4$ are independently CH, N; $W_1$ is O, $S(O)r$ (r=0–2), $CR_4R_4$, N—$R_1$, a bond; $W_2$ is O, $S(O)r$ (r=0–2), $CR_4R_4$, N—$R_1$; t=0–2; $W_3$, $W_4$, $W_5$ are independently O, $S(O)r$ (r=0–2), $CR_4R_4$, N—$R_1$ with the proviso that no S—S, S—O or O—O bond formation can occur to form a saturated ring; u=1–3; Any one of $Z_3$, $Z_4$ must be a carbon atom to which the remainder of the molecule is attached.

387. $Z_1$, $Z_4$ are N; $Z_2$, $Z_3$ are independently $CR_2$; $Y_1$, $Y_2$ are C; $Y_3$, $Y_4$ are independently CH, N; $W_1$ is O, $S(O)r$ (r=0–2), $CR_4R_4$, N—$R_1$, a bond; $W_2$ is O, $S(O)r$ (r=0–2), $CR_4R_4$, N—$R_1$; t=0–2; $W_3$, $W_4$, $W_5$ are independently O, $S(O)r$ (r=0–2), $CR_4R_4$, N—$R_1$ with the proviso that no S—S, S—O or O—O bond formation can occur to form a saturated ring; u=1–3; Any one of $Z_2$, $Z_4$ must be a carbon atom to which the remainder of the molecule is attached.

388. $Z_1$, $Z_4$ are N; $Z_2$, $Z_3$ are independently $CR_2$; $Y_1$, $Y_2$ are C; $Y_3$, $Y_4$ are independently CH, N; $W_1$ is O, $S(O)r$ (r=0–2), $CR_4R_4$, N—$R_1$, a bond; $W_2$ is O, $S(O)r$ (r=0–2), $CR_4R_4$, N—$R_1$; t=0–2; $W_3$, $W_4$, $W_5$ are independently O, $S(O)r$ (r=0–2), $CR_4R_4$, N—$R_1$ with the proviso that no S—S, S—O or O—O bond formation can occur to form a saturated ring; u=1–3; Any one of $Z_2$, $Z_3$ must be a carbon atom to which the remainder of the molecule is attached.

389. $Z_2$ is N; $Z_1$, $Z_3$, $Z_4$ are independently $CR_2$; $Y_1$, $Y_2$ are C; $Y_3$, $Y_4$ are independently CH, N; $W_1$ is O, S(O)r (r=0–2), $CR_4R_4$, N—$R_1$, a bond; $W_2$ is O, S(O)r (r=0–2), $CR_4R_4$, N—$R_1$; t=0–2; $W_3$, $W_4$, $W_5$ are independently O, S(O)r (r=0–2), $CR_4R_4$, N—$R_1$ with the proviso that no S—S, S—O or O—O bond formation can occur to form a saturated ring; u=1–3; Any one of $Z_1$, $Z_3$, $Z_4$ must be a carbon atom to which the remainder of the molecule is attached.

390. $Z_2$, $Z_3$ are N; $Z_1$, $Z_4$ are independently $CR_2$; $Y_1$, $Y_2$ are C; $Y_3$, $Y_4$ are independently CH, N; $W_1$ is O, S(O)r (r=0–2), $CR_4R_4$, N—$R_1$, a bond; $W_2$ is O, S(O)r (r=0–2), $CR_4R_4$, N—$R_1$; t=0–2; $W_3$, $W_4$, $W_5$ are independently O, S(O)r (r=0–2), $CR_4R_4$, N—$R_1$ with the proviso that no S—S, S—O or O—O bond formation can occur to form a saturated ring; u=1–3; Any one of $Z_1$, $Z_4$ must be a carbon atom to which the remainder of the molecule is attached.

391. $Z_2$, $Z_4$ are N; $Z_1$, $Z_3$ are independently $CR_2$; $Y_1$, $Y_2$ are C; $Y_3$, $Y_4$ are independently CH, N; $W_1$ is O, S(O)r (r=0–2), $CR_4R_4$, N—$R_1$, a bond; $W_2$ is O, S(O)r (r=0–2), $CR_4R_4$, N—$R_1$; t=0–2; $W_3$, $W_4$, $W_5$ are independently O, S(O)r (r=0–2), $CR_4R_4$, N—$R_1$ with the proviso that no S—S, S—O or O—O bond formation can occur to form a saturated ring; u=1–3; Any one of $Z_1$, $Z_3$ must be a carbon atom to which the remainder of the molecule is attached.

392. $Z_3$ is N; $Z_1$, $Z_2$, $Z_4$ are independently $CR_2$; $Y_1$, $Y_2$ are C; $Y_3$, $Y_4$ are independently CH, N; $W_1$ is O, S(O)r (r=0–2), $CR_4R_4$, N—$R_1$, a bond; $W_2$ is O, S(O)r (r=0–2), $CR_4R_4$, N—$R_1$; t=0–2; $W_3$, $W_4$, $W_5$ are independently O, S(O)r (r=0–2), $CR_4R_4$, N—$R_1$ with the proviso that no S—S, S—O or O—O bond formation can occur to form a saturated ring; u=1–3; Any one of $Z_1$, $Z_2$, $Z_4$ must be a carbon atom to which the remainder of the molecule is attached.

393. $Z_3$, $Z_4$ are N; $Z_1$, $Z_2$ are independently $CR_2$; $Y_1$, $Y_2$ are C; $Y_3$, $Y_4$ are independently CH, N; $W_1$ is O, S(O)r (r=0–2), $CR_4R_4$, N—$R_1$, a bond; $W_2$ is O, S(O)r (r=0–2), $CR_4R_4$, N—$R_1$; t=0–2; $W_3$, $W_4$, $W_5$ are independently O, S(O)r (r=0–2), $CR_4R_4$, N—$R_1$ with the proviso that no S—S, S—O or O—O bond formation can occur to form a saturated ring; u=1–3; Any one of $Z_1$, $Z_2$ must be a carbon atom to which the remainder of the molecule is attached.

394. $Z_4$ is N; $Z_1$, $Z_2$ $Z_3$ are independently $CR_2$; $Y_1$, $Y_2$ are C; $Y_3$, $Y_4$ are independently CH, N; $W_1$ is O, S(O)r (r=0–2), $CR_4R_4$, N—$R_1$, a bond; $W_2$ is O, S(O)r (r=0–2), $CR_4R_4$, N—$R_1$; t=0–2; $W_3$, $W_4$, $W_5$ are independently O, S(O)r (r=0–2), $CR_4R_4$, N—$R_1$ with the proviso that no S—S, S—O or O—O bond formation can occur to form a saturated ring; u=1–3; Any one of $Z_1$, $Z_2$, $Z_3$ must be a carbon atom to which the remainder of the molecule is attached.

The preferred embodiments of formula 15-B

395. $Z_1$ is N; $Z_2$, $Z_3$ $Z_4$ are independently $CR_2$; $Y_1$, $Y_2$ are C; $Y_3$, $Y_4$ are independently CH, N; $W_1$ is O, S(O)r (r=0–2), $CR_4R_4$, N—$R_1$; $W_2$, $W_3$, $W_4$ are independently O, S(O)r (r=0–2), $CR_4R_4$, N—$R_1$ with the proviso that no S—S, S—O or O—O bond formation can occur to form a saturated ring; t=1–2; u=1–3; Any one of $Z_2$, $Z_3$, $Z_4$ must be a carbon atom to which the remainder of the molecule is attached.

396. $Z_1$, $Z_2$ are N; $Z_3$, $Z_4$ are independently $CR_2$; $Y_1$, $Y_2$ are C; $Y_3$, $Y_4$ are independently CH, N; $W_1$ is O, S(O)r (r=0–2), $CR_4R_4$, N—$R_1$; $W_2$, $W_3$, $W_4$ are independently O, S(O)r (r=0–2), $CR_4R_4$, N—$R_1$ with the proviso that no S—S, S—O or O—O bond formation can occur to form a saturated ring; t=1–2; u=1–3; Any one of $Z_3$, $Z_4$ must be a carbon atom to which the remainder of the molecule is attached.

397. $Z_1$, $Z_3$ are N; $Z_2$, $Z_4$ are independently $CR_2$; $Y_1$, $Y_2$ are C; $Y_3$, $Y_4$ are independently CH, N; $W_1$ is O, S(O)r (r=0–2), $CR_4R_4$, N—$R_1$; $W_2$, $W_3$, $W_4$ are independently O, S(O)r (r=0–2), $CR_4R_4$, N—$R_1$ with the proviso that no S—S, S—O or O—O bond formation can occur to form a saturated ring; t=1–2; u=1–3; Any one of $Z_2$, $Z_4$ must be a carbon atom to which the remainder of the molecule is attached.

398. $Z_1$, $Z_4$ are N; $Z_2$, $Z_3$ are independently $CR_2$; $Y_1$, $Y_2$ are C; $Y_3$, $Y_4$ are independently CH, N; $W_1$ is O, S(O)r (r=0–2), $CR_4R_4$, N—$R_1$; $W_2$, $W_3$, $W_4$ are independently O, S(O)r (r=0–2), $CR_4R_4$, N—$R_1$ with the proviso that no S—S, S—O or O—O bond formation can occur to form a saturated ring; t=1–2; u=1–3; Any one of $Z_2$, $Z_3$ must be a carbon atom to which the remainder of the molecule is attached.

399. $Z_2$ is N; $Z_1$, $Z_3$ $Z_4$ are independently $CR_2$; $Y_1$, $Y_2$ are C; $Y_3$, $Y_4$ are independently CH, N; $W_1$ is O, S(O)r (r=0–2), $CR_4R_4$, N—$R_1$; $W_2$, $W_3$, $W_4$ are independently O, S(O)r (r=0–2), $CR_4R_4$, N—$R_1$ with the proviso that no S—S, S—O or O—O bond formation can occur to form a saturated ring; t=1–2; u=1–3; Any one of $Z_1$, $Z_3$, $Z_4$ must be a carbon atom to which the remainder of the molecule is attached.

400. $Z_2$, $Z_3$ are N; $Z_1$, $Z_4$ are independently $CR_2$; $Y_1$, $Y_2$ are C; $Y_3$, $Y_4$ are independently CH, N; $W_1$ is O, S(O)r (r=0–2), $CR_4R_4$, N—$R_1$; $W_2$, $W_3$, $W_4$ are independently O, S(O)r (r=0–2), $CR_4R_4$, N—$R_1$ with the proviso that no S—S, S—O or O—O bond formation can occur to form a saturated ring; t=1–2; u=1–3; Any one of $Z_1$, $Z_4$ must be a carbon atom to which the remainder of the molecule is attached.

401. $Z_2$, $Z_4$ are N; $Z_1$, $Z_3$ are independently $CR_2$; $Y_1$, $Y_2$ are C; $Y_3$, $Y_4$ are independently CH, N; $W_1$ is O, S(O)r (r=0–2), $CR_4R_4$, N—$R_1$; $W_2$, $W_3$, $W_4$ are independently O, S(O)r (r=0–2), $CR_4R_4$, N—$R_1$ with the proviso that no S—S, S—O or O—O bond formation can occur to form a saturated ring; t=1–2; u=1–3; Any one of $Z_1$, $Z_3$ must be a carbon atom to which the remainder of the molecule is attached.

402. $Z_3$ is N; $Z_1$, $Z_2$, $Z_4$ are independently $CR_2$; $Y_1$, $Y_2$ are C; $Y_3$, $Y_4$ are independently CH, N; $W_1$ is O, S(O)r (r=0–2), $CR_4R_4$, N—$R_1$; $W_2$, $W_3$, $W_4$ are independently O, S(O)r (r=0–2), $CR_4R_4$, N—$R_1$ with the proviso that no S—S, S—O or O—O bond formation can occur to form a saturated ring; t=1–2; u=1–3; Any one $Z_1$, $Z_2$, $Z_4$ of must be a carbon atom to which the remainder of the molecule is attached.

403. $Z_3$, $Z_4$ are N; $Z_1$, $Z_2$ are independently $CR_2$; $Y_1$, $Y_2$ are C; $Y_3$, $Y_4$ are independently CH, N; $W_1$ is O, S(O)r (r=0–2), $CR_4R_4$, N—$R_1$; $W_2$, $W_3$, $W_4$ are independently O, S(O)r (r=0–2), $CR_4R_4$, N—$R_1$ with the proviso that no S—S, S—O or O—O bond formation can occur to form a saturated ring; t=1–2; u=1–3; Any one of $Z_1$, $Z_2$ must be a carbon atom to which the remainder of the molecule is attached.

404. $Z_4$ is N; $Z_1$, $Z_2$, $Z_3$ are independently $CR_2$; $Y_1$, $Y_2$ are C; $Y_3$, $Y_4$ are independently CH, N; $W_1$ is O, S(O)r (r=0–2), $CR_4R_4$, N—$R_1$; $W_2$, $W_3$, $W_4$ are independently O, S(O)r (r=0–2), $CR_4R_4$, N—$R_1$ with the proviso that no S—S, S—O or O—O bond formation can occur to form a saturated ring; t=1–2; u=1–3; Any one $Z_1$, $Z_2$, $Z_3$ of must be a carbon atom to which the remainder of the molecule is attached.

The preferred embodiments of formula 15-C:

405. $Z_1$, $Z_2$, $Z_3$ are independently $CR_2$; $Y_1$, $Y_2$, $Y_4$ are C; $Y_2$ is N; $W_1$, $W_2$, $W_4$ are independently O, S(O)r (r=0–2), $CR_4R_4$, N—$R_1$ with the proviso that no S—S, S—O or O—O bond formation can occur to form a saturated ring; t=1–2; u=1–2; Any one $Z_1$, $Z_2$, $Z_3$ of must be a carbon atom to which the remainder of the molecule is attached.

406. $Z_1$ is N; $Z_2$, $Z_3$ are independently $CR_2$; $Y_1$, $Y_2$, $Y_4$ are C; $Y_2$ is N; $W_1$, $W_2$, $W_4$ are independently O, S(O)r (r=0–2), $CR_4R_4$, N—$R_1$ with the proviso that no S—S, S—O or O—O bond formation can occur to form a saturated ring; t=1–2; u=1–2; Any one $Z_2$, $Z_3$ of must be a carbon atom to which the remainder of the molecule is attached.

407. $Z_1$, $Z_3$ are N; $Z_3$ is $CR_2$; $Y_1$, $Y_2$, $Y_4$ are C; $Y_2$ is N; $W_1$, $W_2$, $W_4$ are independently O, S(O)r (r=0–2), $CR_4R_4$, N—$R_1$ with the proviso that no S—S, S—O or O—O bond formation can occur to form a saturated ring; t=1–2; u=1–2; $Z_3$ is the carbon atom to which the remainder of the molecule is attached.

The expression 'fused bicyclic heteroaryl group' is used in the specification and claims to mean:

A group comprising two fused rings in which one has aromatic character [i.e. Huckel's rule (4n+2)] and the other ring is non-aromatic;

The fused bicyclic heteroaryl group contains one to six heteroatoms selected from the group O, S, N and N—$R_1$;

The fused bicyclic heteroaryl group is bonded to the remainder of the molecule through a carbon atom in the aromatic ring as shown in the formula I;

The aromatic ring of the fused bicyclic heteroaryl group contains five or six ring atoms (including bridgehead atoms) selected from $CR_2$, N, O, S or N—$R_1$. The aromatic ring of the fused bicyclic heteroaryl group contains 0 to 3 heteroatoms selected from the group O, S, N and N—$R_1$;

The non-aromatic ring of the fused bicyclic heteroaryl group contains five to eight ring atoms (including bridgehead atoms) selected from $CR_4R_4$, N, N—$R_1$, O, $S(O)_n$ where n=0–2. The non-aromatic ring of the fused bicyclic heteroaryl group contains 0 to 4 heteroatoms selected from N, N—$R_1$, O or $S(O)_n$ where n=0 to 2.

Examples of fused bicyclic heteroaryl groups are optionally substituted ring systems such as one of the following:
4,5,6,7-tetrahydrothieno[3,2-c]pyridine, optionally substituted by e.g., arylalkyl such as benzyl; by alkoxyarylalkyl such as 4-methoxybenzyl; by C1–C6alkyl such as methyl; by heteroarylalkyl such as pyridin-3-ylmethyl; by arylalkylCO— such as phenylacetyl; or heteroarylCO— such as pyridin-3-ylcarbonyl; e.g. by alkylCO— such as acetyl;
5,6,7,8-tetrahydroimidazo[1,2-a]pyrazine, optionally substituted e.g., by C1–C6alkyl such as methyl;
5,6-dihydro-8H-imidazo[2,1-c][1,4]thiazine;
6,7-Dihydro-5H-pyrrolo[1,2-a]imidazole
5,6-Dihydro-8H-imidazo[2,1-c][1,4]oxazine
5,6-Dihydro-4H-pyrrolo[1,2-b]pyrazole
4,5,6,7-tetrahydropyrazolo[1,5-a]pyridine
6-oxo-5,6,7,8-tetrahydro-imidazo[1,2-a]pyrazine, optionally substituted e.g., by C1–C6alkyl such as methyl;
6,7-Dihydro-4H-pyrazolo[5,1-c][1,4]thiazine;
4H-5-thia-1,6a-diazapentalene;
7H-Imidazo[1,2-c]thiazole;
4-oxo-6,7-dihydro-4H-pyrazolo[5,1-c][1,4]oxazine;
6,7-Dihydro-4H-thieno[3,2-c]pyran;
6,7-Dihydro-4H-thieno[3,2-c]thiopyran;
6,7-dihydro-4H-thieno[3,2-c]pyridine, optionally substituted by C2–C7alkoxycarbonyl;
6,7,8,9-tetrahydro-5H-imidazo[1,2-a]azepine;
5,6,7,8-tetrahydroimidazo[1,2-a]pyrazine, optionally substituted by arylalkyl such as benzyl;
5,5-Dioxo-4,5,6,7-tetrahydro-5$\lambda^6$-pyrazolo[5,1-c][1,4]thiazine;
4,5,6,7-tetrahydropyrazolo[1,5-a]pyrazine;
5,6-Dihydro-4H-cyclopenta[b]furan;
4,5-Dihydro-6-thia-1,7a-diazaindene;
5,6-Dihydro-8-H-imidazo[2,1-c][1,4]thiazine;
4H-5-thia-1,6a-diazapentalene;
2,3-Dihydropyrazolo[5,1-b]thiazole;
2,3-Dihydropyrazolo[5,1-b]oxazole;
6,7-dihydro-4H-pyrazolo[5,1-c][1,4]oxazine;
6,7-5H-Dihydropyrazolo[5,1-b]oxazine; and
4,5,6,7-tetrahydropyrazolo[1,5-a]pyrazine optionally substituted, e.g, by alkoxyalkylCO— such as 2-methoxyacetyl; or by alkyloxyalkylCO— such as methoxyacetyl.

Further examples of bicyclic heteroarylgroups are as follows:

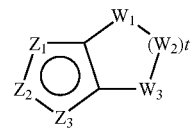

16-A

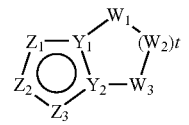

16-B

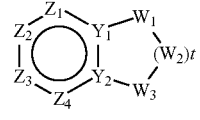

16-C

In formula 16-A Z1, Z2 and Z3 are independently $CR_2$, N, O, S or
N—$R_1$ and one of Z1–Z3 is carbon and is bonded to the remainder of the molecule as shown in formula I. When one of Z's is $CR_2$ the other two Zs can be either two N or one N and O, S, N—$R_1$ in any combinations with out disrupting the aromaticity; when two Z,s=$CR_2$ the other Z can be optionally selected from one N, O, S or N—$R_1$ in any combination with out disrupting the aromaticity;
$W_1$, $W_2$ and $W_3$ are independently $CR_4R_4$, S, SO, $SO_2$, O, N—$R_1$, C=O; with the proviso that no S—S or O—O or S—O bond formation can occur to form the saturated ring system; t=1 to 4.

In formula 16-B Z1, Z2 and Z3 are independently $CR_2$, N, O, S or N—$R_1$ and one of Z1–Z3 is carbon and is bonded to the remainder of the molecule as shown in formula I.

When one of Z's=$CR_2$, then the other two Z's can be independently $CR_2$, N, O, S or N—$R_1$ in any combinations with out disrupting the aromaticity;

When two Z's=N, then the other carbon in the ring is bonded to the penem portion of the molecule as shown in formula I.

$W_1$, $W_2$ and $W_3$ are independently $CR_4R_4$, S, SO, $SO_2$, O, N—$R_1$, t=1 to 4;

$Y_1$ and $Y_2$=N or C; with the proviso that when the aromatic heterocycle is imidazole, the saturated ring may not contain a S adjacent to the bridgehead carbon.

In formula 16-C Z1, Z2, Z3 and Z4 are independently $CR_2$ or N and one of Z1–Z4 is carbon and is bonded to the remainder of the molecule.

$W_1$, $W_2$ and $W_3$ are independently $CR_4R_4$, S, SO, $SO_2$, O, or N—$R_1$; with the proviso that no S—S or O—O or S—O bond formation can occur to form the saturated ring system; t=1 to 4.

$Y_1$ and $Y_2$ are independently C or N.

The more preferred embodiment of the formula 16-A:
1. t=1 to 3.
2. In formula 16-A Z1 is N, S, N—$R_1$ or O and one of Z2 or Z3 is $CR_2$ and the other of Z2 or Z3 is carbon and is bonded to the remainder of the molecule as shown in formula I.
3. In formula 16-A Z3 is N, S, N—$R_1$ or O and one of Z2 or Z1 is $CR_2$ and the other of Z2 or Z1 is carbon and is bonded to the remainder of the molecule as shown in formula I.
4. In formula 16-A Z2 is N, S, N—$R_1$ or O and one of Z1 or Z3 is $CR_2$ and the other of Z1 or Z3 is carbon bonded to the remainder of the molecule as shown in formula I.
5. In formula 16-A Z1 is N, N—$R_1$, O or S and Z2 is N, O or S and Z3 is a carbon bonded to the penem portion of the molecule as shown in formula I.
6. In formula 16-A Z3 is N, N—$R_1$, O or S and Z2 is N, O or S and Z1 is a carbon bonded to the penem portion of the molecule as shown in formula I.
7. In formula 16-A Z1 is N, N—$R_1$, O or S and Z3 is N, O or S and Z2 is a carbon bonded to the penem portion of the molecule as shown in formula I.
8. In formula 16-A Z1 is N, S, N—$R_1$ or O and Z2 or Z3 is $CR_2$ and the other of Z2 or Z3 is carbon and is bonded to the remainder of the molecule; $W_1$, $W_2$ and $W_3$ are independently $CR_4R_4$.
9. In formula 16-A Z3 is N, S, N—$R_1$ or O and one of Z2 or Z1 is $CR_2$ and the other of Z2 or Z1 is carbon and is bonded to the remainder of the molecule; $W_1$, $W_2$, and $W_3$ are independently $CR_4R_4$.
10. In formula 16-A Z2 is N, S, N—$R_1$ or O and one of Z1 or Z3 is $CR_2$ and the other of Z1 or Z3 is carbon and is bonded to the remainder of the molecule; $W_1$, $W_2$, and $W_3$ are independently $CR_4R_4$.
11. In formula 16-A Z1 is N, N—$R_1$, O or S and Z2 is N, O or S; Z3 is a carbon bonded to the penem portion of the molecule; $W_1$, $W_2$, $W_3$ are independently $CR_4R_4$.
12. In formula 16-A Z3 is N, N—$R_1$, O or S; Z2 is N, O or S; Z1 is a carbon bonded to the penem portion of the molecule; $W_1$, $W_2$, $W_3$ are independently $CR_4R_4$.
13. In formula 16-A Z1 is N, N—$R_1$, O or S; Z3 is N, O or S; Z2 is a carbon bonded to the penem portion of the molecule; $W_1$, $W_2$, $W_3$ are independently $CR_4R_4$.
14. In formula 16-A Z3 is N, N—$R_1$, O or S; Z1 is N, O or S; Z2 is a carbon bonded to the penem portion of the molecule; $W_1$, $W_2$, $W_3$ are independently $CR_4R_4$.
15. In formula 16-A Z1 is N, S, N—$R_1$ or O; one of Z2 or Z3 is $CR_2$ and the other of Z2 or Z3 is carbon and is bonded to the remainder of the molecule, t=1–3; one $W_2$ is N—$R_1$, O or $S(O)_n$, n=0–2 and another $W_2$=CR4R4.
16. In formula 16-A Z3 is N, S, N—$R_1$ or O; one of Z2 or Z1 is $CR_2$ and the other of Z2 or Z1 is carbon and is bonded to the remainder of the molecule, t=1–3; one $W_2$ is N—$R_1$, O or $S(O)_n$, n=0–2 and another $W_2$=CR4R4.
17. In formula 16-A Z2 is N, S, N—$R_1$ or O; one of Z1 or Z3 is $CR_2$ and the other of Z1 or Z3 is carbon and is bonded to the remainder of the molecule; t=1–3; one $W_2$ is N—$R_1$, O or $S(O)_n$, n=0–2 and another $W_2$ is CR4R4.
18. In formula 16-A when Z1=N, N—$R_1$, O or S and Z2=N, O or S and Z3=a carbon bonded to the penem portion of the molecule where t=1–3 then one $W_2$=N—$R_1$, O or $S(O)_n$, n=0–2 and other $W_2$=CR4R4.
19. In formula 16-A Z3=N, N—$R_1$, O or S and Z2=N, O or S and Z1=a carbon bonded to the penem portion of the molecule where t=1–3 then one $W_2$=N—$R_1$, O or $S(O)_n$, n=0–2 and other $W_2$=CR4R4.
20. In formula 16-A when Z1=N, N—$R_1$, O or S and Z3=N, O or S and Z2=a carbon bonded to the penem portion of the molecule where t=1–3 then one $W_2$=N—$R_1$, O or $S(O)_n$, n=0–2 and other $W_2$=CR4R4.
21. In formula 16-A Z1=N, S, N—$R_1$ or O and Z2 or Z3=$CR_2$ and the other of Z2 or Z3 is carbon and is bonded to the remainder of the molecule; then $W_1$ and $W_3$=$CH_2$ or both hydrogens on the methylene linkage can be substituted to form a spiro system with or without the presence of hetero atoms selected from O, S=$(O)_n$ (n=0 to 2), N—$R_1$ to form five to eight membered cyclic system; t=1–3; one $W_2$=N—$R_1$, O or $S(O)_n$, n=0–2 and other $W_2$=CR4R4.
22. In formula 16-A Z3=N, S, N—$R_1$ or O and Z2 or Z1=$CR_2$ and the other of Z2 or Z1 is carbon and is bonded to the remainder of the molecule; then $W_1$ and $W_3$=CR4R4; where t=1–3 then one $W_2$=N—$R_1$, O or $S(O)_n$, n=0–2 and other $W_2$=CR4R4.
23. In formula 16-A Z2=N, S, N—$R_1$ or O and Z1 or Z3=$CR_2$ and the other of Z1 or Z3 is carbon and is bonded to the remainder of the molecule; then $W_1$ and $W_3$=CR4R4, where t=1–3 then one $W_2$=N—$R_1$, O or $S(O)_n$, n=0–2 and other $W_2$=CR4R4.
24. In formula 16-A when Z1=N, N—$R_1$, O or S and Z2=N, O or S then Z3=a carbon bonded to the penem portion of the molecule; then $W_1$ and $W_3$=CR4R4, where t=1–3 then one $W_2$=N—$R_1$, O or $S(O)_n$, n=0–2 and other $W_2$=CR4R4.
25. In formula 16-A Z3=N, N—$R_1$, O or S and Z2=N, O or S then Z1=a carbon bonded to the penem portion of the molecule; then $W_1$ and $W_3$=CR4R4, where t=1–3 then one $W_2$=N—$R_1$, O or $S(O)_n$, n=0–2 and other $W_2$=CR4R4.
26. In formula 16-A when Z1=N, N—$R_1$, O or S and Z3=N, O or S then Z2=a carbon bonded to the penem portion of the molecule; then $W_1$ and $W_3$=CR4R4; t=1–3; one $W_2$ is N—$R_1$, O or $S(O)_n$, n=0–2 and another $W_2$ is CR4R4.
27. In formula 16-A Z3 is N, N—$R_1$, O or S; Z1 is N, O or S; Z2 is a carbon bonded to the remainder of the molecule; $W_1$ and $W_3$ are independently CR4R4; t=1–3; one $W_2$ is N—$R_1$, O or $S(O)_n$, n=0–2 and another $W_2$ is CR4R4.

The more preferred embodiments of the formula 16-B:
28. In formula 16-B t=3.
29. In formula 16-B Z1 and Z3 are N; Y1 is N; Y2 is C and Z2 is carbon and is bonded to the remainder of the molecule as shown in formula I.
30. In formula 16-B Z2 and Z3 are N; Y1 is N; Y2 is C and Z1 is carbon and is bonded to the remainder of the molecule as shown in formula I.
31. In formula 16-B Z1 is N, Y1 is N, Y2 is C, one of $Z_2$ or $Z_3$ is $CR_2$ and the other of Z2 or Z3 is a carbon and is bonded to the remainder of the molecule as shown in formula I.

32. In formula 16-B Z1 is N, Y1 is C, Y2 is N, one of $Z_2$ or $Z_3$ is $CR_2$ and the other of Z2 or Z3 is a carbon and is bonded to the remainder of the molecule as shown in formula I.

33. In formula 16-B Z1 is N, Y1 is N, Y2 is C, one of $Z_2$ or $Z_3$ is $CR_2$ and the other of Z2 or Z3 is a carbon and is bonded to the remainder of the molecule as shown in formula I, $W_1$ and $W_3$ are independently CR4R4; t=1–3; one $W_2$ is N—$R_1$, O, S=(O)$_n$ (n=0–2), and another $W_2$ is CR4R4.

34. In formula 16-B Z1 is N, Y1 is C, Y2 is N, one of $Z_2$ or $Z_3$ is $CR_2$ and the other of Z2 or Z3 is a carbon and is bonded to the remainder of the molecule as shown in formula I; $W_1$ and $W_3$ are independently CR4R4; t=1–3; one $W_2$ is N—$R_1$, O, S=(O)$_n$ (n=0–2), and another $W_2$ is CR4R4.

35. In formula 16-B Z3 is N; Y1 is N; Y2 is C; one of Z1 or Z2 is $CR_2$ and the other of $Z_1$ or $Z_2$ is carbon and is bonded to the remainder of the molecule as shown in formula I.

36. In formula 16-B Z2 is N; Y1 is N; Y2 is C; one of Z1 or Z3 is $CR_2$ and the other of $Z_1$ or $Z_3$ is carbon and is bonded to the remainder of the molecule as shown in formula I.

37. In formula 16-B Z1 and Z2 are N; Y1 is N; Y2 is C; and Z3 is carbon and is bonded to the remainder of the molecule as shown in formula I.

38. In formula 16-B Z1, Z2 and Z3 are independently $CR_2$; Y1 is C; Y2 is N; except one of Z1–Z3 is carbon and is bonded to the remainder of the molecule as shown in formula I.

39. In formula 16-B Z1 and Z3 are N; Y1 is N; Y2 is C; Z2 is carbon and is bonded to the remainder of the molecule as shown in formula I; and t=1–3.

40. In formula 16-B Z2 and Z3 are N; Y1 is N; Y2 is C; and Z1 is carbon and is bonded to the remainder of the molecule; and t=1–3;

41. In formula 16-B Z2 and Z3 are N, Y1 is C and Y2=N and Z1 is carbon and is bonded to the remainder of the molecule and t=1–3;

42. In formula 16-B Z2 and Z3 are N, Y1 is N; Y2 is C; Z1 is carbon and is bonded to the remainder of the molecule; $W_1$ and $W_3$ are independently $CH_2$ or both hydrogens on the methylene linkage can be substituted to form a spiro system with or without the presence of hetero atoms selected from O, S(O)$_n$ n=0–2, N—$R_1$ to form five to eight membered cyclic system; t=1–3 and $W_2$ is $CH_2$, N—$R_1$, O, S(O)$_n$ where n=0–2.

43. In formula 16-B Z3 is N; Y1 is N; Y2 is C; Z1 is $CR_2$ and Z2 is the carbon atom bonded to the remainder of the molecule.

44. In formula 16-B Z3 is N; Y1 is N; Y2 is C; Z1 is $CR_2$; Z2 is the carbon atom bonded to the remainder of the molecule; $W_1$, $W_2$ and $W_3$ are independently CR4R4; t=1 to 3.

45. In formula 16-B Z3 is N; Y1 is N; Y2 is C; Z1 is $CR_2$; Z2 is the carbon atom bonded to the remainder of the molecule; $W_1$ and $W_3$ are independently CR4R4; and one of $W_2$ is N—$R_1$, O or S(O)$_n$, and another $W_2$ is CR4R4; t=1–3.

46. In formula 16-B Z3 is N; Y1 is N; Y2 is C; Z1 is $CR_2$; Z2 is the carbon atom bonded to the remainder of the molecule; $W_1$ and $W_2$ are independently CR4R4; $W_3$ is N—$R_1$, O or S(O)$_n$; and t=2.

47. In formula 16-B Z3 is N; Y1 is N; Y2 is C; Z1 is $CR_2$; Z2 is the carbon atom bonded to the remainder of the molecule; $W_1$ and $W_3$ are independently CR4R4; $W_2$ is N—$R_1$, O or S(O)$_n$; and t=1.

48. In formula 16-B Z2 is N; Y1 is N; Y2 is C; Z3 is $CR_2$; Z1 is the carbon bonded to the remainder of the molecule; $W_1$ and $W_2$ is $CH_2$ or both hydrogens on the methylene linkage can be substituted to form a spiro system with or without the presence of hetero atoms selected from O, S(O)$_n$ n=0–2, N—$R_1$ to form five to eight membered cyclic system; $W_3$ is N—$R_1$, O or S(O)$_n$; and t=3.

49. In formula 16-B Z2 is N; Y1 is N; Y2 is C, Z3 is $CR_2$; Z1 is the carbon bonded to the remainder of the molecule; $W_1$ and $W_3$ are independently $CH_2$ or both hydrogens on the methylene linkage can be substituted to form a spiro system with or without the presence of hetero atoms selected from O, S(O)$_n$ n=0–2, N—$R_1$ to form five to eight membered cyclic system; and one $W_2$ is N—$R_1$, O or S(O)$_n$ and another $W_2$ is CR4R4; and t=2.

50. In formula 16-B Z2 is N; Y1 is N; Y2 is C; Z3 is $CR_2$; Z1 is the carbon bonded to the remainder of the molecule; $W_1$ and $W_3$ are independently $CH_2$ or both hydrogens on the methylene linkage can be substituted to form a spiro system with or without the presence of hetero atoms selected from O, S(O)$_n$ n=0–2, N—$R_1$ to form five to eight membered cyclic system; $W_2$ is N—$R_1$, O or S(O)$_n$; and t=1.

51. In formula 16-B Z2 is N; Y1 is N; Y2 is C; Z1 is $CR_2$; Z3 is the carbon bonded to the remainder of the molecule; $W_1$ and $W_3$ are independently CR4R4; one of $W_2$ is N—$R_1$, O or S(O)$_n$ and another $W_2$ is CR4R4; and t=3.

52. In formula 16-B Z2 is N; Y1 is N; Y2 is C; Z1 is $CR_2$; Z3 is the carbon bonded to the remainder of the molecule; $W_1$ and $W_3$ are independently CR4R4; one $W_2$ is N—$R_1$, O or S(O)$_n$, and another $W_2$ is CR4R4; and t=2.

53. In formula 16-B Z2 is N; Y1 is N; Y2 is C; Z1 is $CR_2$; Z3 is the carbon bonded to the remainder of the molecule; $W_1$ and $W_3$ are independently CR4R4; $W_2$ is N—$R_1$, O or S(O)$_n$; and t=1.

54. In formula 16-B Z1 and Z2 are N; Y1 is N; Y2 is C; Z3 is carbon and is bonded to the remainder of the molecule; $W_1$ and $W_3$ are independently CR4R4; one of $W_2$ is N—$R_1$, O or S(O)$_n$ and another $W_2$ is CR4R4; and t=3.

55. In formula 16-B Z1 and Z2 are N; Y1 is N; Y2 is C; Z3 is carbon and is bonded to the remainder of the molecule; $W_1$ and $W_3$ are independently CR4R4; one of $W_2$ is N—$R_1$, O or S(O)$_n$ and another $W_2$ is CR4R4; and t=2.

56. In formula 16-B Z1 and Z2 are N; Y1 is N; Y2 is C; Z3 is carbon and is bonded to the remainder of the molecule; $W_1$ and $W_3$ are independently CR4R4; $W_2$ is N—$R_1$, O or S(O)$_n$; and t=1

57. In formula 16-B Z1 and Z2 are independently $CR_2$; Y1 is C; Y2 is N; Z3 is carbon and is bonded to the remainder of the molecule; $W_1$ and $W_3$ are independently CR4R4; one of $W_2$ is N—$R_1$, O or S(O)$_n$; another $W_2$ is CR4R4; and t=3.

58. In formula 16-B Z1 and Z2 are independently $CR_2$; Y1 is C and Y2 is N and Z3 is carbon and is bonded to the remainder of the molecule; $W_1$ and $W_3$ are independently CR4R4; and one $W_2$ is N—$R_1$, O or S(O)$_n$ and the other $W_2$ is CR4R4; and t=2.

59. In formula 16-B Z1 and Z2 are independently $CR_2$; Y1 is C; Y2 is N; Z3 is carbon and is bonded to the remainder of the molecule; $W_1$ and $W_3$ are independently CR4R4; $W_2$ is N—$R_1$, O or S(O)$_n$; and t=1.

60. In formula 16-B Z1 and Z3 are independently $CR_2$; Y1 is C; Y2 is N; Z2 is carbon and is bonded to the remainder of the molecule; $W_1$ and $W_3$ are independently CR4R4; one $W_2$ is N—$R_1$, O or S(O)$_n$; another $W_2$ is CR4R4; and t=3.

61. In formula 16-B Z1 and Z3 are independently CR$_2$; Y1 is C; Y2 is N; Z2 is carbon and is bonded to the remainder of the molecule; $W_1$ and $W_3$ are independently CR4R4; and one $W_2$ is N—$R_1$, O or S(O)$_n$ and the other $W_2$ is CR4R4; and t=2.

62. In formula 16-B Z1 and Z3 are independently CR$_2$; Y1 is C; Y2 is N; Z2 is carbon and is bonded to the remainder of the molecule; $W_1$ and $W_3$ are independently CR4R4; $W_2$ is N—$R_1$, O or S(O)$_n$; and t=1.

63. In formula 16-B Z3 and Z2 are independently CR$_2$; Y1 is C; Y2 is N; Z1 is carbon and is bonded to the remainder of the molecule; $W_1$ and $W_2$ are independently CR4R4; one $W_2$ is N—$R_1$, O or S(O)$_n$; another $W_2$ is CR4R4; and t=3.

64. In formula 16-B Z3 and Z2 are independently CR$_2$; Y1 is C; Y2 is N; Z1 is carbon and is bonded to the remainder of the molecule; $W_1$ and $W_3$ are independently CR4R4; one $W_2$ is N—$R_1$, O or S(O)$_n$; the other $W_2$ is CR4R4; and t=2.

65. In formula 16-B Z3 and Z2 are independently CR$_2$; Y1 is C; Y2 is N; Z1 is carbon and is bonded to the remainder of the molecule; $W_1$ and $W_3$ are independently CR4R4; $W_2$ is N—$R_1$, O or S(O)$_n$; and t=1.

66. In formula 16-B Z3 is N; Y1 is N; Y2 is C; one of Z1 and Z2 is CR$_2$ and the other is C; W, is CR4R4; $W_2$ is CR4R4; $W_3$ is CH$_2$, N—$R_1$ or O; and t=1.

67. In formula 16-B Z3 is N; Y1 is N; Y2 is C; one of Z1 and Z2 is CR$_2$ and the other is C; $W_1$ is CR4R4; $W_2$ is C=O; $W_3$ is N—$R_1$; and t=1.

68. In formula 16-B Z3 is N; Y1 is N; Y2 is C; one of Z1 and Z2 is CR$_2$ and the other is C; $W_1$ is N—$R_1$; $W_2$ is C=O; $W_3$ is CR4R4; and t=1.

69. In formula 16-B Z3 is N; Y1 is N; Y2 is C; one of Z1 and Z2 is CR$_2$ and the other is C; $W_1$ is C=O; $W_2$ is N—$R_1$; $W_3$ is CH$_2$; and t=1.

The more preferred embodiments of the formula 16-C are:

70. In formula 16-C Z1, Z2, Z3 and Z4 are independently CR$_2$; one of Z1–Z4 is carbon and is bonded to the remainder of the molecule; $Y_1$ and $Y_2$ are C; t=1 to 3; and $W_1$, $W_2$ and $W_3$ are independently CR4R4, S, SO, SO$_2$, O, or N—$R_1$.

71. In formula 16-C Z1, Z2, Z3 and Z4 are independently CR$_2$ and one of Z1–Z4 is carbon and is bonded to the remainder of the molecule; $Y_1$ and $Y_2$=C or N; t=1 to 3; $W_1$, $W_2$ and $W_3$ are independently CR4R4, S, SO, SO$_2$, 0, or N—$R_1$.

72. In formula 16-C Z1, Z2, Z3 and Z4 are independently CR$_2$; $Y_1$ and $Y_2$ are N; t=to 3; $W_1$, $W_2$ and $W_3$ are independently CR4R4, S, SO, SO$_2$, 0, or N—$R_1$.

73. In formula 16-C Z1 is N and Z2, Z3 and Z4 are independently CR$_2$; $Y_1$ and $Y_2$ are C; t=1 to 3; $W_1$, $W_2$ and $W_3$ are independently CR4R4, S, SO, SO$_2$, 0, or N—$R_1$.

74. In formula 16-C Z1 is N and Z2, Z3 and Z4 are independently CR$_2$; one of Z1–Z4 is carbon and is bonded to the remainder of the molecule; $Y_1$ is C; $Y_2$ is N; t=1 to 3; and $W_1$, $W_2$ and $W_3$ are independently CR4R4, S, SO$_2$, 0, or N—$R_1$.

75. In formula 16-C Z2=N and Z1, Z3 and Z4 are independently CR$_2$; one of Z1–Z4 is carbon and is bonded to the remainder of the molecule; $Y_1$ and $Y_2$ are C; t=1 to 3; and $W_1$, $W_2$ and $W_3$ are independently CR4R4, S, SO, SO$_2$, O, or N—$R_1$.

76. In formula 16-C Z2 is N and Z1, Z3 and Z4 are independently CR$_2$; one of Z1–Z4 is carbon and is bonded to the remainder of the molecule; $Y_1$ is C; $Y_2$ is N; t=1 to 3; and $W_1$, $W_2$ and $W_3$ are independently CR4R4, S, SO, SO2, O, or N—$R_1$.

77. In formula 16-C Z3 is N; Z1, Z2 and Z4 are independently CR$_2$; one of Z1–Z4 is carbon and is bonded to the remainder of the molecule; $Y_1$ and $Y_2$ are C; t=1 to 3; and $W_1$, $W_2$ and $W_3$ are independently CR4R4, S, SO, SO2, O, or N—$R_1$.

78. In formula 16-C Z3 is N and Z1, Z2 and Z4 are independently CR$_2$; one of Z1–Z4 is carbon and is bonded to the remainder of the molecule; $Y_1$ is C and $Y_2$ is N; t=1 to 3; and $W_1$, $W_2$ and $W_3$ are independently CR4R4, S, SO, SO2, O, or N—$R_1$.

79. In formula 16-C Z4 is N and Z1, Z2 and Z3 are independently CR$_2$; one of Z1–Z4 is carbon and is bonded to the remainder of the molecule; Y, and $Y_2$ are C; t=1 to 3; and $W_1$, $W_2$ and $W_3$ are independently CR4R4, S, SO, SO2, O, or N—$R_1$.

80. In formula 16-C Z4 is N and Z1, Z2 and Z3 are independently CR$_2$; one of Z1–Z4 is carbon and is bonded to the remainder of the molecule; $Y_1$ is N; $Y_2$ is C; t=1 to 3; and $W_1$, $W_2$ and $W_3$ are independently CR4R4, S, SO, SO2, O, or N—$R_1$.

81. In formula 16-C Z1 is N and Z2, Z3 and Z4 are independently CR$_2$; one of Z1–Z4 is carbon and is bonded to the remainder of the molecule; $Y_1$ and $Y_2$ are C; t=1 to 3; and $W_1$, $W_2$ and $W_3$ are independently CR4R4, S, SO, SO2, O, or N—$R_1$.

82. In formula 16-C Z1 and Z2 are N and Z3 or Z4 are independently CR$_2$; one of Z1–Z4 is carbon and is bonded to the remainder of the molecule; $Y_1$ is C; $Y_2$ is N; t=1 to 3; and $W_1$, $W_2$ and $W_3$ are independently CR4R4, S, SO, SO2, O, or N—$R_1$.

83. In formula 16-C Z1 and Z3 are N and Z2 or Z4 are independently CR$_2$; one of Z1–Z4 is carbon and is bonded to the remainder of the molecule; $Y_1$ is C; $Y_2$ is N; t=1 to 3; and $W_1$, $W_2$ and $W_3$ are independently CR4R4, S, SO, SO2, O, or N—$R_1$.

84. In formula 16-C Z1 and Z4 are N and Z2 or Z3 are independently CR$_2$; one of Z1–Z4 is carbon and is bonded to the remainder of the molecule; $Y_1$ is N; $Y_2$ is C; t=1 to 3; and $W_1$, $W_2$ and $W_3$ are independently CR4R4, S, SO, SO2, O, or N—$R_1$.

85. In formula 16-C Z1, Z2, Z3 are N and Z4 is carbon and is bonded to the remainder of the molecule; $Y_1$ is C; $Y_2$ is N; t=1 to 3; and $W_1$, $W_2$ and $W_3$ are independently CR4R4, S, SO, SO2, O, or N—$R_1$.

86. In formula 16-C Z1, Z3 and Z4 are N and Z2 is carbon and is bonded to the remainder of the molecule; $Y_1$ and $Y_2$ are C; t=1 to 3; and $W_1$, $W_2$ and $W_3$ are independently CR4R4, S, SO, SO2, O, or N—$R_1$.

87. In formula 16-C Z1, Z2 and Z4 are N and Z3 is carbon and is bonded to the remainder of the molecule; $Y_1$ and $Y_2$ are C and t=1 to 3; and $W_1$, $W_2$ and $W_3$ are independently CR4R4, S, SO, SO2, O, or N—$R_1$.

88. In formula 16-C Z2, Z3, Z4 are N and Z1 is carbon and is bonded to the remainder of the molecule; $Y_1$ and $Y_2$ are C and t=1 to 3; and $W_1$, $W_2$ and $W_3$ are independently CR4R4, S, SO, SO2, O, or N—$R_1$.

The most preferred compounds of the present invention are:

1.  7-[(5-benzyl-4,5,6,7-tetrahydrothieno[3,2-c]pyridin-2-yl)]-4,7-dihydro-[1,4]thiazepine-3,6-dicarboxylicacid 6-methyl ester.
2.  7-(7-Methyl-5,6,7,8-tetrahydroimidazo[1,2-a]pyrazin-2-yl)-4,7-dihydro-[1,4]thiazepine-3,6-dicarboxylicacid 6-methyl ester.

3. 7-(5,6,7,8-tetrahydroimidazo[1,2-a]pyrazin-2-yl)-4,7-dihydro-[1,4]thiazepine-3,6-dicarboxylicacid 6-methyl ester.
4. 7-{[5-(4-methoxybenzyl)-4,5,6,7-tetrahydrothieno[3,2-c]pyridin-2-yl)]4,7-dihydro-[1,4]thiazepine-3,6-dicarboxylicacid 6-methyl ester.
5. 7-(5,6-dihydro-8H-imidazo[2,1-c][1,4]thiazin-2-yl) 4,7-dihydro-[1,4]thiazepine-3,6-dicarboxylicacid 6-methyl ester.
6. 7-(6,7-Dihydro-5H-pyrrolo[1,2-a]imidazol-2-yl)-4,7-dihydro-[1,4]thiazepine-3,6-dicarboxylicacid 6-methyl ester.
7. 7-(5,6-Dihydro-8H-imidazo[2,1-c][1,4]oxazin-2-yl)-4,7-dihydro-[1,4]thiazepine-3,6-dicarboxylicacid 6-methyl ester.
8. 7-(5,6-Dihydro-4H-pyrrolo[1,2-b]pyrazol-2-yl)-4,7-dihydro-[1,4]thiazepine-3,6-dicarboxylicacid 6-methyl ester.
9. 7-(4,5,6,7-tetrahydropyrazolo[1,5-a]pyridin-2-yl)-4,7-dihydro-[1,4]thiazepine-3,6-dicarboxylicacid 6-methyl ester.
10. 7-(7-Methyl-6-oxo-5,6,7,8-tetrahydro-imidazo[1,2-a]pyrazin-2-yl)-4,7-dihydro-[1,4]thiazepine-3,6-dicarboxylicacid 6-methyl ester.
11. 7-(6,7-Dihydro-4H-pyrazolo[5,1-c][1,4]thiazin-2-ylmethyl)-4,7-dihydro-[1,4]thiazepine-3,6-dicarboxylicacid 6-methyl ester.
12. 7-(4H-5-thia-1,6a-diazapentalen-2-ylmethyl)-4,7-dihydro-[1,4]thiazepine-3,6-dicarboxylicacid 6-methyl ester.
13. 7-(7H-Imidazo[1,2-c]thiazol-2-ylmethyl)-4,7-dihydro-[1,4]thiazepine-3,6-dicarboxylicacid 6-methyl ester.
14. 7-[(4-oxo-6,7-dihydro-4H-pyrazolo[5,1-c][1,4]oxazin-2-yl)methyl)-4,7-dihydro-[1,4]thiazepine-3,6-dicarboxylicacid 6-methyl ester.
15. 7-(6,7-Dihydro-4H-thieno[3,2-c]pyran-2-ylmethylene)-4,7-dihydro-[1,4]thiazepine-3,6-dicarboxylicacid 6-methyl ester.
16. 7-(6,7-Dihydro-4H-thieno[3,2-c]thiopyran-2-ylmethyl)-4,7-dihydro-[1,4]thiazepine-3,6-dicarboxylicacid 6-methyl ester.
17. 7-(5-Methyl-4,5,6,7-tetrahydro-thieno[3,2-c]pyridin-2-ylmethyl)-4,7-dihydro-[1,4]thiazepine-3,6-dicarboxylic acid 6-methyl ester.
18. 7-(6-ethoxycarbonyl-4,5,6,7-tetrahydro-thieno[2,3-c]pyridin-2-yl)-4,7-dihydro-[1,4]thiazepine-3,6-dicarboxylic acid 6-methyl ester.
19. 7-(6,7,8,9-tetrahydro-5H-imidazo[1,2-a]azepin-2-ylmethl)-4,7-dihydro-[1,4]thiazepine-3,6-dicarboxylic acid 6-methyl ester.
20. 7-(7-Benzyl-5,6,7,8-tetrahydroimidazo[1,2-a]pyrazin-2-ylmethyl)-4,7-dihydro-[1,4]thiazepine-3,6-dicarboxylic acid 6-methyl ester.
21. 7-{[5-(pyridin-3-ylmethyl)-4,5,6,7-tetrahydrothieno[3,2-c]pyridin-2-yl]methyl}-4,7-dihydro-[1,4]thiazepine-3,6-dicarboxylic acid 6-methyl ester.
22. 7-{[5-(pyridin-3-ylcarbonyl)-4,5,6,7-tetrahydrothieno[3,2-c]pyridin-2-yl)]methyl}-4,7-dihydro-[1,4]thiazepine-3,6-dicarboxylic acid 6-methyl ester.
23. 7-{[5-(phenylacetyl)-4,5,6,7-tetrahydrothieno[3,2-c]pyridin-2-yl)]methyl}-4,7-dihydro-[1,4]thiazepine-3,6-dicarboxylic acid 6-methyl ester.
24. 7-(5,5-Dioxo-4,5,6,7-tetrahydro-5$\lambda^6$-pyrazolo[5,1-c][1,4]thiazin-2-ylmethyl)-4,7-dihydro-[1,4]thiazepine-3,6-dicarboxylic acid 6-methyl ester.
25. 7-(4,5,6,7-tetrahydropyrazolo[1,5-a]pyrazin-2-ylmethyl)-4,7-dihydro-[1,4]thiazepine-3,6-dicarboxylic acid 6-methyl ester.
26. 7-(5,5-Dimethyl-4H-1,6a-diazapentalen-2-ylmethyl)-4,7-dihydro-[1,4]thiazepine-3,6-dicarboxylic acid 6-methyl ester.
27. 7-(5,6-Dihydro-4H-cyclopenta[b]furan-2-ylmethyl)-4,7-dihydro-(1,4]thiazepine-3,6-dicarboxylic acid 6-methyl ester.
28. 7-(4,5-Dihydro-6-thia-1,7a-diazainden-2-ylmethyl)-4,7-dihydro-[1,4]thiazepine-3,6-dicarboxylic acid 6-methyl ester.
29. 7-(6,6-Dimethyl-5,6,7,8-tetrahydroimidazo[1,2-a]pyrizin-2-ylmethyl)-4,7-dihydro-[1,4]thiazepine-3,6-dicarboxylic acid 6-methyl ester.
30. 7-(5,6-Dihydro-8-H-imidazo[2,1-c][1,4]thiazin-3-ylmethyl)-4,7-dihydro-[1,4]thiazepine-3,6-dicarboxylic acid 6-methyl ester.
31. 7-(4H-5-thia-1,6a-diazapentalen-2-ylmethyl)-4,7-dihydro-[1,4]thiazepine-3,6-dicarboxylic acid 6-methyl ester.
32. 7-(2,3-Dihydropyrazolo[5,1-b]thiazol-6-ylmethyl)-4,7-dihydro-[1,4]thiazepine-3,6-dicarboxylic acid 6-methyl ester.
33. 7-(2,3-Dihydropyrazolo[5,1-b]oxazol-6-ylmethyl)-4,7-dihydro-[1,4]thiazepine-3,6-dicarboxylic acid 6-methyl ester.
34. 7-[(5-acetyl-4,5,6,7-tetrahydrothieno[3,2-c]pyridin-2-yl)methyl]-4,7-dihydro-[1,4]thiazepine-3,6-dicarboxylic acid 6-methyl ester.
35. 7-(6,7-dihydro-4H-pyrazolo[5,1-c][1,4]oxazin-2-ylmethyl)-4,7-dihydro-[1,4]thiazepine-3,6-dicarboxylic acid 6-methyl ester.
36. 7-(6,7-5H-Dihydropyrazolo[5,1-b]oxazin-2-ylmethyl)-4,7-dihydro-[1,4]thiazepine-3,6-dicarboxylic acid 6-methyl ester.
37. 7-(Imidazo[2,1-b][1,3]benzothiazol-2-ylmethyl)-4,7-dihydro-[1,4]thiazepine-3,6-dicarboxylic acid 6-methyl ester.
38. 7-[(7-methoxyimidazo[2,1-b][1,3]benzothiazol-2-ylmethyl)-4,7-dihydro-[1,4]thiazepine-3,6-dicarboxylic acid 6-methyl ester.
39. 7-[(7-chloroimidazo[2,1-b][1,3]benzothiazol-2-ylmethyl)-4,7-dihydro-[1,4]thiazepine-3,6-dicarboxylic acid 6-methyl ester.
40. 7-Imidazo[1,2-a]quinolin-2-ylmethyl-4,7-dihydro-[1,4]thiazepine-3,6-dicarboxylic acid 6-methyl ester.
41. 7-(6,7-dihydro-5H-cyclopenta[d]imidazo[2,1-b][1,3]thiazol-2-ylmethylene)-4,7-dihydro-[1,4]thiazepine-3,6-dicarboxylic acid 6-methyl ester.
42. 7-(Imidazo[1.2-a]quinoxaline-2-ylmethyl)-4,7-dihydro-[1,4]thiazepine-3,6-dicarboxylic acid 6-methyl ester.
43. 7-[(7-methylimidazo[2,1-b][1,3]benzothiazol-2-ylmethyl)-4,7-dihydro-[1,4]thiazepine-3,6-dicarboxylic acid 6-methyl ester.
44. 7-(4,5,6,7-tetrahydro-1,3a,3b,8-tetraaza-cyclopenta[a]indene-2-ylmethyl)-4,7-dihydro-[1,4]thiazepine-3,6-dicarboxylic acid 6-methyl ester.
45. 7-[(10-benzyl-11-oxo-10,11-dihydrodibenzo[b,f][1,4)oxazepin-8-yl)methyl]-4,7-dihydro-[1,4]thiazepine-3,6-dicarboxylic acid 6-methyl ester.
46. 7-(5-ethoxy-7,8-dihydro-6H-3,4,8b-triaza-as-indacen-2-ylmethylene)-4,7-dihydro-[1,4]thiazepine-3,6-dicarboxylic acid 6-methyl ester.
47. 7-(4H, 10H-pyrazolo[5,1-c][1,4]benzoxazepin-2-ylmethyl)-4,7-dihydro-[1,4]thiazepine-3,6-dicarboxylic acid 6-methyl ester.
48. 7-(5H-Imidazo[2,1-a]isoindol-2-ylmethyl)-4,7-dihydro-[1,4]thiazepine-3,6-dicarboxylic acid 6-methyl ester.

49. 7-[(5-methylimidazo[1,2-b][1,3]benzothiazol-2-ylmethyl)]-4,7-dihydro-[1,4]thiazepine-3,6-dicarboxylic acid 6-methyl ester.
50. 7-[(7-fluoroimidazo[2,1-b][1,3]benzothiazol-2-ylmethyl)-4,7-dihydro-[1,4]thiazepine-3,6-dicarboxylic acid 6-methyl ester.
51. 7-(5,8-dihydro-6H-imidazo[2,1-b]pyrano(4,3-d][1,3]thiazol-2-ylmethyl)-4,7-dihydro-[1,4]thiazepine-3,6-dicarboxylic acid 6-methyl ester.
52. 7-(imidazo[2,1-b]benzothiazol-7-ylmethyl)-4,7-dihydro-(1,4]thiazepine-3,6-dicarboxylic acid 6-methyl ester.
53. 7-([1,3]thiazolo[3,2-a]benzimidazol-2-ylmethyl)-4,7-dihydro-[1,4]thiazepine-3,6-dicarboxylic acid 6-methyl ester.
54. 7-(7,8-dihydro-6H-cyclopenta[3,4]pyrazolo[5,1-b][1,3]thiazol-2-ylmethyl)-4,7-dihydro-[1,4]thiazepine-3,6-dicarboxylic acid 6-methyl ester.
55. 7-(5,6,7,8-tetrahydroimidazo[2,1-b][1,3]benzothiazol-2-ylmethyl)-4,7-dihydro-[1,4]thiazepine-3,6-dicarboxylic acid 6-methyl ester.
56. 7-[(9-methyl-9H-imidazo[1,2-a]benzimidazol-2-yl)methyl]-4,7-dihydro-[1,4]thiazepine-3,6-dicarboxylic acid 6-methyl ester.
57. 7-(4H-thieno[2',3':4,5]thiopyrano[2,3-b]pyridin-2-ylmethyl)-4,7-dihydro-[1,4]thiazepine-3,6-dicarboxylic acid 6-methyl ester.
58. 7-[(5-methyl-7,8-dihydro-6H-cyclopenta[e][1,2,4]triazolo[1,5-a]pyrimidin-2-yl)methyl]-4,7-dihydro-[1,4]thiazepine-3,6-dicarboxylic acid 6-methyl ester.
59. 7-{[7-(ethoxycarbonyl)-6,7,8,9-tetrahydropyrido[3,4-e][1,2,4]triazolo[1,5-a]pyrimidin-2-yl]methyl}-4,7-dihydro-[1,4]thiazepine-3,6-dicarboxylic acid 6-methyl ester.
60. 7-(8',9'-dihydro-6'H-spiro[1,3-dioxolane-2,7'-[1,2,4]triazolo[1,5-a]quinazolin]-2'-ylmethyl)-4,7-dihydro-[1,4]thiazepine-3,6-dicarboxylic acid 6-methyl ester.
61. 7-[(5-methyl-6,7,8,9-tetrahydro[1,2,4]triazolo[1,5-a]quinazolin-2-yl)methyl]-4,7-dihydro-[1,4]thiazepine-3,6-dicarboxylic acid 6-methyl ester.
62. 7-[(5-methoxy-7,8-dihydro-6H-cyclopenta[e]imidazo[1,2-a]pyrimidin-2-yl)methyl]-4,7-dihydro-[1,4]thiazepine-3,6-dicarboxylic acid 6-methyl ester.
63. 7-({5-[2-(benzyloxy)ethoxy]-7,8-dihydro-6H-cyclopenta[e]imidazo[1,2-a]pyrimidin-2-yl}methyl)-4,7-dihydro-[1,4]thiazepine-3,6-dicarboxylic acid 6-methyl ester.
64. 7-(2,3-dihydro(1,3]thiazolo[3,2-a]benzimidazol-6-ylmethyl)-4,7-dihydro-[1,4]thiazepine-3,6-dicarboxylic acid 6-methyl ester.
65. 7-(3,4-dihydro-2H-[1,3]thiazino[3,2-a]benzimidazol-7-ylmethyl)-4,7-dihydro-[1,4]thiazepine-3,6-dicarboxylic acid 6-methyl ester.
66. 7-([1,3]thiazolo[3,2-a]benzimidazol-6-ylmethyl)-4,7-dihydro-[1,4]thiazepine-3,6-dicarboxylic acid 6-methyl ester.
67. 7-(7,8-dihydro-5H-pyrano[4,3-d]pyrazolo[5,1-b][1,3]oxazol-2-ylmethyl)-4,7-dihydro-[1,4]thiazepine-3,6-dicarboxylic acid 6-methyl ester.
68. 7-(5,6,7,8-tetrahydropyrazolo[5,1-b][1,3]benzoxazol-2-ylmethyl)-4,7-dihydro-[1,4]thiazepine-3,6-dicarboxylic acid 6-methyl ester.
69. 7-{[6-(Ethoxycarbonyl)-5,6,7,8-tetrahydropyrazolo[5',1':2,3][1,3]oxazolo[5,4-c]pyridin-2-yl]methyl}-4,7-dihydro-[1,4]thiazepine-3,6-dicarboxylic acid 6-methyl ester.

Pharmaceutically acceptable salts are those salts which may be administered or provided to a warm blooded animal, preferably sodium, potassium or calcium alkaline earth metal salts.

The compounds according to the present invention have β-lactamase inhibitory and antibacterial properties and are useful for the treatment of infections in humans and animals. It should be noted that the compounds of the present invention, when used in combination with β-lactam antibiotics will result in the increased antibacterial activity (synergistic effect) against class-A and class-C producing organisms. β-Lactam antibiotics include penicillin antibiotics such as piperacillin, amoxycillin, ticarcillin, benzylpenicillins, ampicillin, sulbenicillin, other known penicillins and cephalosporins such as cefatrizine, cephaloridine, cephalothin, cefazolin, cephalexin, cephradine, other known cephalosporins, aztreonam and latamoxef (Moxalactam). Most preferably compounds of this present invention are used with piperacillin or amoxicillin which has a broad spectrum of activity against Gram positive and Gram negative pathogens.

The compounds of the present invention may be provided prior to, simultaneously with, or subsequent to a β-lactam antibiotic ("co-administration"). By "provided", it is intended to include administering the compound directly or in vivo, e.g. pro-drugs. When the compounds of the present invention are co-administered with a β-lactam antibiotic, the ratio of the amount of the compound to the amount of the β-lactam antibiotic may vary in a wide range. The ratio of β-lactam antibiotic to β-lactamase inhibitor may vary from 1:1 to 100:1. Preferably the ratio of the β-lactam antibiotic to β-lactamase inhibitor is less than 10:1. The composition of the present invention may be in a form suitable for oral (PO), intravenous (IV) or topical administration. The compositions of the invention may be in a form of tablets, capsules, creams, syrups, suspension, sterile solutions suitable for injection or infusion. Preferably, the compounds of the present invention are co-administered with piperacillin intravenously or amoxicillin intravenously or orally.

A compound's structural formula includes any tautomers, any stereoisomers (except where stereochemistry is clearly noted) and any crystalline forms.

Chemical Definitions

The term alkyl means both straight and branched chain alkyl moieties of 1–12 carbons, preferably of 1–6 carbon atoms.

The term alkenyl means both straight and branched alkenyl moieties of 2–8 carbon atoms containing at least one double bond, and no triple bond, preferably the alkenyl moiety has 1 or two double bonds. Such alkenyl moieties may exist in the E or Z conformations; the compounds of this invention include both conformations. In the case of alkenyl, hetero atoms such as O, S or N—$R_1$ should not be present on the carbon that is bonded to a double bond;

The term alkynyl includes both straight chain and branched alkynyl moieties containing 2–6 carbon atoms containing at least one triple bond, preferably the alkynyl moiety has one or two triple bonds. In the case of alkynyl, hetero atoms such as O, S or N—$R_1$ should not be present on the carbon that is bonded to a double or triple bond;

The term cycloalkyl refers to a alicyclic hydrocarbon group having 3–7 carbon atoms.

The term perfluoroalkyl is used herein to refer to both straight- and branched-chain saturated aliphatic hydrocarbon groups having at least one carbon atom and two or more fluorine atoms. Examples include $CF_3$, $CH_2CF_3$, $CF_2CF_3$ and $CH(CF_3)_2$.

The term halogen is defined as Cl, Br, F, and I.

If alkyl, alkenyl, alkynyl, or cycloalkyl is "optionally substituted", one or two of the following are possible substituents: nitro, -aryl, -heteroaryl, alkoxycarbonyl-, -alkoxy, -alkoxy-alkyl, alkyl-O—C2–C4alkyl-O—, -cyano, -halogen, -hydroxy, —N—$R_6R_7$, —COOH, —COO-alkyl, -trifluoromethyl, -trifluoromethoxy, arylalkyl, alkylaryl, $R_6R_7$N-alkyl-, HO—C1–C6-alkyl-, alkoxyalkyl-, alkyl-S—, —$SO_2$N—$R_6R_7$, —$SO_2$NH$R_6$, —$CO_2$H, CONR$_6R_7$, aryl-O—, heteroaryl-O—, —S(O)$_s$-aryl (where s=0–2), -alkyl-O-alkyl-NR$_6R_7$, -alkyl-aryl-O-alkylN-$R_6R_7$, C1–C6alkyl, alkenyl, alkynyl, cycloalkyl, alkoxy-alkyl-O—, $R_6R_7$N-alkyl-, and —S(O)$_s$-heteroaryl (where s=0–2); Preferred substitutents for alkyl, alkenyl, alkynyl, and cycloalkyl include: halogen, nitro, aryl, heteroaryl, alkoxycarbonyl-, alkoxy, -alkoxy-alkyl, -cyano, hydroxy, and —N—$R_6R_7$.

Aryl is defined as an aromatic hydrocarbon moiety selected from the group: phenyl, α-naphthyl, β-naphthyl, biphenyl, anthryl, tetrahydronaphthyl, fluorenyl, indanyl, biphenylenyl, acenaphthenyl, groups. Preferred aryl groups are phenyl and biphenyl.

Heteroaryl is defined as a aromatic heterocyclic ring system (monocyclic or bicyclic) where the heteroaryl moieties are selected from: (1) furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline; (2) a bicyclic aromatic heterocycle where a phenyl, pyridine, pyrimidine or pyridizine ring is: (a) fused to a 6-membered aromatic (unsaturated) heterocyclic ring having one nitrogen atom; (b) fused to a 5 or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Preferred heteroaryl groups are furan, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, quinoline, isoquinoline, and naphthyridine.

If aryl or heteroaryl is 'optionally substituted', one or two of the following are possible substituents: nitro, -aryl, -heteroaryl, alkoxycarbonyl-, -alkoxy, -alkoxy-alkyl, alkyl-O—C2–C4alkyl-O—, -cyano, -halogen, -hydroxy, —N—$R_6R_7$, -trifluoromethyl, -trifluoromethoxy, arylalkyl, alkylaryl, $R_6R_7$N-alkyl-, HO—C1–C6-alkyl-, alkoxyalkyl-, alkyl-S—, —$SO_2$N—$R_6R_7$, —$SO_2$NH$R_6$, —$CO_2$H, CONR$_6R_7$, aryl-O—, heteroaryl-O-, —S(O)$_s$-aryl (where s=0–2), -alkyl-O-alkyl-NR$_6R_7$, -alkyl-aryl-O-alkylN.—$R_6R_7$, C1–C6alkyl, alkenyl, alkynyl, cycloalkyl, alkoxy-alkyl-O—, $R_6R_7$N-alkyl-, and —S(O)$_s$-heteroaryl (where s=0–2); Preferred substitutents for aryl and heteroaryl include: alkyl, halogen, —N—$R_6R_7$, trifluoromethyl, -trifluoromethoxy, arylalkyl, and alkylaryl.

Arylalkyl is defined as Aryl-C1–C6alkyl—; Arylalkyl moieties include benzyl, 1-phenylethyl, 2-phenylethyl, 3-phenylpropyl, 2-phenylpropyl and the like. The term 'optionally substituted' refers to unsubstituted or substituted with 1 or 2 substituents on the alkyl or aryl moiety as defined above.

Alkylaryl is defined as C1–C6alkyl-aryl-. The term 'optionally substituted' refers to unsubstituted or substituted with 1 or 2 substituents on the aryl or alkyl moiety as defined above.

Heteroaryl-C1–C6- alkyl is defined as a heteroaryl substituted alkyl moiety wherein the alkyl chain is 1–6 carbon atoms (straight or branched). Alkyl heteroaryl moieties include Heteroaryl-$(CH_2)_{1-6}$— and the like. The term 'optionally substituted' refers to unsubstituted or substituted with 1 or 2 substituents on the alkyl or heteroaryl moiety as defined above;

C1–C6 alkylheteroaryl is defined an alkyl chain of 1–6 carbon atoms (straight or branched) attached to a heteroaryl moiety, which is bonded to the rest of the molecule. For example C1–C6-alkyl-Heteroaryl—. The term 'optionally substituted' refers to unsubstituted or substituted with 1 or 2 substituents on the alkyl or heteroaryl moiety as defined above;

Saturated or partially saturated heterocycles groups are defined as heterocyclic rings selected from the moieties; aziridinyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl. Preferred saturated or partially saturated heterocycles include: aziridinyl, azetidinyl, 1,4-dioxanyl, hexahydroazepinyl, piperazinyl, piperidinyl, pyrrolidinyl, morpholinyl, thiomorpholinyl, tetrahydroquinolinyl, tetrahydroisoquinolinyl, dihydroimidazolyl, and dihydroisooxazolyl.

C1–C6 alkyl mono or bicyclic saturated or partially saturated heterocycles is defined as an alkyl group (straight or branched) of C1–C6 attached to a heterocycles (which is defined before) through a carbon atom or a nitrogen atom and the other end of the alkyl chain attached to the rest of the molecule. The terms 'optionally substituted' refers to unsubstituted or substituted with 1 or 2 substituents present on the alkyl or heterocyclic portion of the molecule, as defined before;

Arylalkyloxyalkyl is defined as Aryl-C1–C6alkyl-O—C1–C6alkyl-. The term 'optionally substituted' refers to unsubstituted or substituted with 1 or 2 substituents present on the alkyl and/or aryl portions as defined before;

Alkyloxyalkyl is defined as C1–C6 alkyl-O—C1–C6alkyl-. The term 'optionally substituted' refers to unsubstituted or substituted with 1 or 2 substituents present at the alkyl moiety as defined before;

Aryloxyalkyl is defined as Aryl-O—C1–C6 alkyl-. The term 'optionally substituted' refers to unsubstituted or substituted with 1 or 2 substituents present at the alkyl or aryl moiety as defined before;

Heteroarylalkyloxyalkyl is defined as Heteroaryl-C1–C6alkyl-O—C1–C6alkyl-. The term 'optionally substituted' refers to unsubstituted or substituted with 1 or 2 substituents present on the alkyl or heteroaryl moiety as defined before;

Aryloxyaryl is defined as Aryl-O-Aryl-. The term 'optionally substituted' refers to unsubstituted or substituted with 1 or 2 substituents present on the aryl moiety as defined before;

Aryloxyheteroaryl is defined as Aryl-O-Heteroaryl- or -Aryl-O-Heteroaryl; In this definition either the aryl moiety or the heteroaryl moiety can be attached to the remaining portion of the molecule; The term 'optionally substituted' refers to unsubstituted or substituted with 1 or 2 substituents present on the aryl moiety or on the heteroaryl moiety as defined before;

Alkyl aryloxyaryl is defined as Aryl-O-Aryl-C1–C6alkyl-; The term 'optionally substituted' refers to unsubstituted or substituted with 1 or 2 substituents present at the aryl moiety as defined before;

Alkylaryloxyheteroaryl is defined as Heteroaryl-O-Aryl-C1–C6alkyl-; The term 'optionally substituted' refers to unsubstituted or substituted with 1 or 2 substituents present on the aryl moiety or on the hetroaryl moiety as defined before;

Alkylaryloxyalkylamine is defined as $R_6R_7N$—C1–C6alkyl-O-Aryl-C1C6alkyl-; The terms 'optionally substituted' refers to unsubstituted or substituted with 1 or 2 substituents present on the alkyl or aryl moiety as defined before; $R_6$ and $R_7$ as defined before;

Alkoxycarbonyl is defined as C1–C6alkyl-O—C=O—; The term 'optionally substituted' refers to unsubstituted or substituted with 1 or 2 substituents present on the alkyl portion of the alkoxy moiety as defined before;

Aryloxycarbonyl is defined as Aryl-O—C=O—; The term 'optionally substituted' refers to unsubstituted or substituted with 1 or 2 substituents present at the aryl moiety as defined before;

Heteroaryloxy carbonyl is defined as Heteroaryl-O—C=O—; The term 'optionally substituted' refers to unsubstituted or substituted with 1 or 2 substituents present at the heteroaryl moiety as defined before;

Alkoxy is defined as C1–C6alkyl-O—; The terms 'optionally substituted' refers to unsubstituted or substituted with 1 or 2 substituents present at the alkyl moiety as defined before;

Aryloxy is defined as Aryl-O—; The term 'optionally substituted' refers to unsubstituted or substituted with 1 or 2 substituents present at the aryl moiety as defined before;

Heteroaryloxy is defined as Heteroaryl-O—; The term 'optionally substituted' refers to unsubstituted or substituted with 1 or 2 substituents present at the heteroaryl moiety as defined before;

Alkenyloxy is defined as C3–C6 alkene-O—; Example allyl-O—, but-2-ene-O or like moieties; The term 'optionally substituted' refers to unsubstituted or substituted with 1 or 2 substituents present at the alkene moiety as defined before, with the proviso that no hetero atom such as O, S or N—$R_1$ is present on the carbon atom, which is attached to a double bond;

Alkynyloxy is defined as C3–C6alkyne-O—; Example CH triple bond C—$CH_2$—O—, or like moieties; The term 'optionally substituted' refers to unsubstituted or substituted with 1 or 2 substituents present at the alkyne moiety as defined before, with the proviso that no hetero atom such as O, S or N—$R_1$ is present on a carbon atom which is attached to a double or triple bond;

Alkylaminoalkoxy is defined as $R_6R_7N$—C1–C6-alkyl-O—C1–C6-alkyl-, where the terminal alkyl group attached to the oxygen is connected to the rest of the molecule; The terms $R_6$ and $R_7$ are defined above; The term 'optionally substituted' refers to unsubstituted or substituted with 1 or 2 substituents present at the alkyl moiety as defined before;

Alkylenedioxy is defined as —O—$CH_2$—O— or —O—$(CH_2)_2$—O—;

Aryloxyalkylamine is defined as $R_6R_7N$—C1–C6-alkyl-O-Aryl-, where the aryl is attached to the rest of the molecule; The term 'optionally substituted' refers to unsubstituted or substituted with 1 or 2 substituents present at the alkyl or aryl moiety as defined before;

Arylalkenyl is defined as Aryl-C2–C8alkene-, with the proviso that no hetero atom such as O, S or N—$R_1$ is present on the carbon atom, which is attached to a double bond; The term 'optionally substituted' refers to unsubstituted or substituted with 1 or 2 substituents present on the alkene or aryl moiety as defined before;

Heteroaryloxyalkyl is defined as Heteroaryl-O—C1–C6alkyl-; The term 'optionally substituted' refers to unsubstituted or substituted with 1 or 2 substituents present at the heteroaryl moiety as defined before;

Heteroaryloxyaryl is defined as Heteroaryl-O-aryl-, where the aryl moiety is attached to the rest of the molecule; The term 'optionally substituted' refers to unsubstituted or substituted with 1 or 2 substituents present at the heteroaryl moiety or the aryl moiety as defined before;

Alkoxy, alkoxyalkyl, alkoxyalkyloxy and alkylthioalkyloxy are moieties wherein the alkyl chain is 1–6 carbon atoms (straight or branched). Aryloxy, heteroaryloxy, arylthio and heteroarylthio are moieties wherein the aryl and heteroaryl groups are as herein before defined. Arylalkyloxy, heteroarylalkyloxy, arylalkylthio and heteroarylalkylthio are moieties wherein the aryl and heteroaryl groups are as herein before defined and wherein the alkyl chain is 1–6 carbons (straight or branched). Aryloxyalkyl, heteroaryloxyalkyl, aryloxyalkyloxy and heteroaryloxyalkyloxy are substituents wherein the alkyl radical is 1–6 carbon atoms. The terms monoalkylamino and dialkylamino refer to moieties with one or two alkyl groups wherein the alkyl chain is 1–6 carbons and the groups may be the same or different. The terms monoalkylaminoalkyl and dialkylaminoalkyl refer to monoalkylamino and dialkylamino moieties with one or two alkyl groups (the same or different) bonded to the nitrogen atom which is attached to an alkyl group of 1–3 carbon atoms.

$IC_{50}$ Determination for the Inhibitors

β-Lactamase inhibitory activity of the inhibitors was determined spectrophotometrically as described by Bush et al, [Bush, K., Macalintal, C., Rasmussen, B. A., Lee, V. and Yang, Y. *Antimicrobial Agents and Chemotherapy* 1993, 37, 851]. Homogeneously purified class A β-lactamases TEM-1 from *E. coli* and Imi-1 from *Enterobacter cloacae*, class B enzyme CcrA from *Bacteroides fragilis* and class C enzyme AmpC from *Enterobacter cloaca* were employed in the assay. The enzyme concentrations for TEM-1, Imi-1, CcrA and AmpC were 4.3, 7.1, 1.2 and 2.1 nM, respectively. A wide range of inhibitor concentrations were prepared in 50 mM $PO_4$, pH 7.0 to include the possible $IC_{50}$ values. The substrate used to initiate the enzyme reaction was nitrocefin at 50 μg/ml in the same buffer as the inhibitor. Initially the enzyme and inhibitor (20 μl each) were preincubated for 10 minutes at 25° C. prior to the addition of 160 μl volume of nitrocefin. Initial rates of hydrolysis were monitored for 5 minutes at 495 nm using a Molecular Devices Spectra Max 250 with kinetic protocol of SoftMax Program. Readings from the Spectra Max 250 were exported and transferred to Microsoft Excel. The percent of inhibition of each inhibitor concentration was calculated based on the control enzyme activity. The inhibitor concentration that caused a 50% reduction in the enzymatic activity ($IC_{50}$) was determined graphically.

Antimicrobial susceptibility testing. The in vitro activities of the antibiotics were determined by the microbroth dilution method as recommended by the National Committee for Clinical Laboratory Standards (NCCLS). (NCCLS. 2000. Methods for Dilution Antimicrobial Susceptibility Tests for Bacteria That Grow Aerobically; Approved Standards: M7-A5, vol. 19. National Committee for Clinical Laboratory Standards, Villanova, Pa.). Mueller-Hinton II broth (MHBII)(BBL Cockeysville, Md.), was used for the testing procedure. Microtiter plates containing 50 µl per well of two-fold serial dilutions of piperacillin combined with a constant amount (4 ug/ml) of a B-lactamase inhibitor were inoculated with 50 µl of inoculum to yield the appropriate density ($10^5$ CFU/ml) in 100 • I final volume. The plates were incubated for 18–22 hours at 35° C. in ambient air. The minimal inhibitory concentration (MIC) for all isolates was defined as the lowest concentration of antimicrobial agent that completely inhibits the growth of the organism as detected by the unaided eye.

In Vivo Antibacterial Protection

Materials:

Animals:

Female mice strain CD-1, approximately 18–22 grams, were received from Charles River Laboratories and quarantined 7 days prior to use. In addition, mice may be rendered neutropenic using cytoxan.

Infections:

Clinical isolates that have been adapted to cause infection in mice, are used in the experiment, including infections with strains of *E. coli, K. pneumoniae, M. morganii, E. cloacae, S. marcescens, C. freundii*, staphylococci, streptococci, *P. aeruginosa* and *N. gonorrhoeae*.

Preparation:

Animals are housed five to a cage with free access to food and water, in accordance with NIH guidelines.

Experimental Protocol:

Mice are challenged by injecting 0.5 ml intraperitoneally or 0.05 ml intranasally of a predetermined bacterial inoculum suspended in broth, saline or hog gastric mucin (supplemented with dried bovine hemoglobin for *N. gonorrhoeae*). The bacterial inoculum is equivalent to 10–100 $LD_{50}$s of the specific infecting strain and will result in death of the non-treated control animals within 7 days: "Bacterial Virulence in Mice". Antibacterial doses (dose concentration prepared by two fold serial dilutions of the antibiotic) are dissolved or suspended in 0.2% aqueous agar or methocel, phosphate buffered saline or an adjuvant are administered orally, subcutaneously or intravenously in the following manner:

a) Orally or subcutaneously: Dose volume of 0.5 ml administered ½ hr after infection. A second dose may be administered 3 hr. after infection for treatment of infections with more virulent organisms.

b) Intravenously: Dose volume of 0.2 ml, administered ½ hr. after infection. For the treatment of infections with more virulent organisms, more doses, up to 48 hr may be administered. (Intravenous dosing will not exceed 3 doses/24 hr period.)

c) Oral pretreatment: Under special circumstances, the pH of the stomach needs to be adjusted in order to increase the gastric stability of the antibiotic. For this purpose, 0.5 ml of phosphate buffered saline (pH7.8, 0.06M) (or specific approved adjuvant) is administered orally ½ hr after infection, followed 5 minutes later by 0.5 ml of antibiotic (also orally) contained in phosphate buffered saline (pH7.8, 0.06M).

Animal Species

A detailed explanation as to the number of animals needed for the determination of in vivo efficacy follows:

A) Novel antibiotics are tested at 5 different dose levels with 5 mice per dose level at each of three routes of administration (oral, subcutaneous and intravenous). Initially the three routes of administration should be investigated so as to determine if the drug is orally absorbed and/or which is the most effective route. This would require 25 mice/route with 3 routes/antibiotic or 75 mice per novel compound tested. One to two novel antibiotics will be tested per experiment (75–150 mice)

B) The effectiveness of the new compound must be compared to that of a standard, or antibiotic of known effectiveness. Known or previously tested antibiotics are tested at 5 dose levels with 5 mice per dose level by a single route of administration, for a total of 25 mice/antibiotic. Usually 3–6 antibiotics will be tested per experiment. (75–150 mice).

C) Untreated controls—In each of the above tests, untreated animals are infected with 3 different concentrations of bacterial inoculum with 10 mice per concentration (30 mice total in each and every test). These untreated controls are used to determine and maintain the infection level between 10–100 LD50s as required for test to test comparison and validity.

Determination of Protective Effects of Antibacterial Agents:

The protective effects of the antibacterial agent(s) are measured by the survival of the infected untreated as compared to the treated animals. For this determination, animals are observed for 7 days after treatment. A census of survivors is taken twice daily and at that time dead as well as moribund animals are removed. The 7 day survival ratio from three separate tests are pooled for estimation of median effective dose (ED50) by computerized program for probit analysis (Cleeland, R. and E. Squires. 1991. Evaluation of New Antimicrobials in Vitro and in Experimental Animal Infections. In Antibiotics in Laboratory Medicine", 3rd. ed., edited by Victor Lorian. Willams and Wilkins Baltimore, Md. pp. 752–783). The test is performed three times on separate days to provide a statistically valid number of animals and to minimize variation in test results on a day to day and test to test basis.

Process of Invention

Compounds of the general formula I can be prepared by a reacting 6-methylidene penems of structure 2 (in the present invention, either bicyclic heteroaryl or tricyclic heteroaryl substituted on the methylidene linkage) (This class of compounds can be prepared by the procedure given in the application U.S. Application No. 60/377,052 and U.S. Application No. 60/377,051) (Scheme 1) with a proper nucleophile in an aprotic or a protic polar solvents (such as water, methanol, ethanol, THF, DMSO or DMF). The nucleophile can be but is not limited to a hydroxy anion, thiolate, alkoxy, aryloxy primary or a secondary amine. The NH in the thiazipine ring can be derivatized by a proper substituent during the course of these transformations. The chemistry involved in the deprotection step is well known to one of ordinary skill in the art.

SCHEME 1

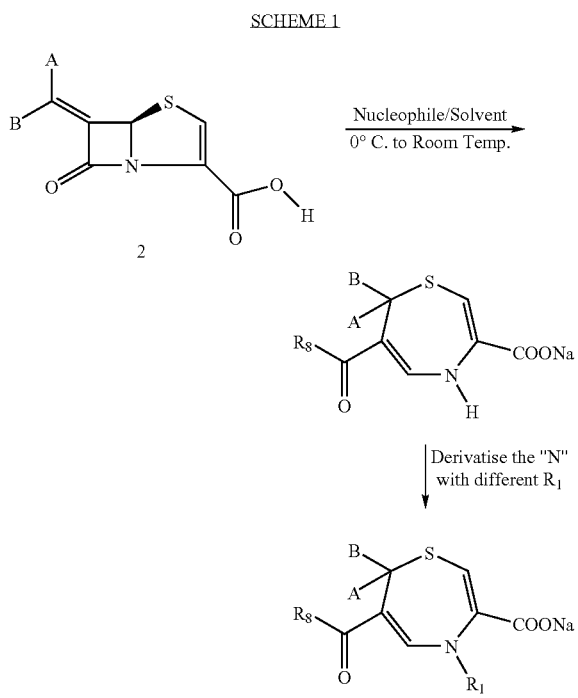

EXPERIMENTALS

General Procedure to Prepare 7-Bicyclic or Tricyclic-4,7-Dihydro-[1,4]Thiazepine-3,6-Dicarboxylic Acid-6-Methyl Ester To a stirred solution of (5R)-Z-bicyclic or tricyclic heteroaryl-4-ylmethylene)penem-3-carboxylic acid (1.4 mmol) in anhydrous methanol (50 ml) at 0° C., NaOMe (80.0 mg 1.5 mmol) is added. The reaction mixture is stirred at room temperature for 2 hrs and concentrated. The product is purified by HP21 resin reverse phase column chromatography. Initially the column is eluted with deionized water (2 L) and later with 10% acetonitrile:water. The fractions containing the product are collected and concentrated under reduced pressure at room temperature. The yellow solid is washed with acetone, filtered and dried.

Example 1

Preparation of 7-(5,6-Dihydro-8H-Imidazo[2,1-C][1,4]Oxazin-2-yl)-4,7-Dihydro-[1,4]Thiazepine-3,6-Dicarboxylic Acid-6-Methyl Ester-3-Sodium Salt 7-(5,6-dihydro-8H-imidazo[2,1-c][1,4]oxazin-2-yl)-4,7-dihydro-[1,4]thiazepine-3,6-dicarboxylic acid-6-methyl ester-3-sodium salt is prepared by following the general procedure as outlined above. Starting from (5R) (6Z)-6-(5,6-dihydro-8H-imidazo[2,1-c][1,4]oxazin-2-ylmethylene)-7-oxo-4-thia-1-azabicyclo[3.2.0]hept-2-ene-2-carboxylic acid sodium salt (500 mg, 1.4 mmol) and sodium methoxide (80 mg, 1.5 mmol) the titled compound is prepared. Yellow amorphous solid; Yield 387 mg, 70%; Mp: 225° C. (Dec); $^1$H NMR: (DMSO-$d_6$) δ 9.16 (d, 1H), 7.64 (d, 1H), 6.24 (s, 1H), 6.08 (s, 1H), 5.41 (s, 1H), 4.64 (q,2H), 3.98–3.80 (m, 4H), 3.54 (s, 3H); (M+H+Na) 360.

Example 2

Preparation of 7-(5,6,7,8-Tetrahydro-8H-Imidazo[1,2-A][1,4]Pyrazin-2-yl)-4,7-Dihydro-[1,4]Thiazepine-3,6-Dicarboxylic Acid-3,6-Disodium Salt To a stirred solution of (5R), (6Z)-7-Oxo-6-(5,6,7,8-tetrahydroimidazo[1,2-a]pyrazin-2-ylmethylene)-4-thia-1-azabicyclo[3.2.0]hept-2-ene-2-carboxylic acid, sodium salt (326 mg, 1 mmol) 0.1 N NaOH (15 ml) is added at room temperature. The reaction mixture is stirred for 1 hr and concentrated. The red solid obtained is dissolved in water and loaded on a HP21 resin reverse phase column chromatography. Initially the column was eluted with deionized water (2 L) and latter with 5% acetonitrile:water. The fractions containing the product are collected and concentrated under reduced pressure at room temperature. The red solid is washed with acetone, filtered and dried. Red amorphous solid; Yield 200 mg, 54%; Mp: 225° C. (Dec); $^1$H NMR: (DMSO-$d_6$) δ 9.31 (s, 1H), 7.82 (s, 1H), 6.66 (s, 1H), 6.10 (s, 1H), 3.95–3.78 (m,3H), 2.9–3.1 (m,4H); (M+H) 324.

What is claimed is:

1. A compound of formula I or a pharmaceutically acceptable salt thereof:

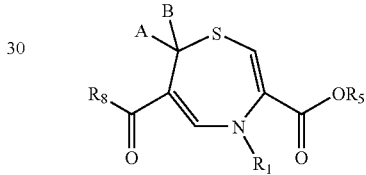

wherein:
one of A and B denotes hydrogen and the other is a fused bicyclic heteroaryl group or a fused tricyclic heteroaryl group;

$R_1$ is H, optionally substituted —C1–C6 alkyl, optionally substituted -aryl, optionally substituted -heteroaryl or mono or bicyclic saturated heterocycles, optionally substituted —C3–C7 cycloalkyl, optionally substituted —C3–C6 alkenyl, optionally substituted —C3–C6 alkynyl with the proviso that both the double bond and the triple bond should not be present at the carbon atom which is directly linked to N; optionally substituted —C1–C6 per fluoro alkyl, —S(O)$_p$ optionally substituted alkyl or aryl where p is 2, optionally substituted —C═Oheteroaryl, optionally substituted —C═Oaryl, optionally substituted —C═O(C1–C6) alkyl, optionally substituted —C═O(C3–C6) cycloalkyl, optionally substituted —C═O mono or bicyclic saturated heterocycles, optionally substituted C1–C6 alkyl aryl, optionally substituted C1–C6 alkyl heteroaryl, optionally substituted aryl-C1–C6 alkyl, optionally substituted heteroaryl-C1–C6 alkyl, optionally substituted C1–C6 alkyl mono or bicyclic saturated heterocycles, optionally substituted arylalkenyl of 8 to 16 carbon atoms, —CONR$_6$R$_7$, —SO$_2$NR$_6$R$_7$, optionally substituted arylalkyloxyalkyl, optionally substituted -alkyl-O-alkyl-aryl, optionally substituted -alkyl-O-alkyl-heteroaryl, optionally substituted aryloxyalkyl, optionally substituted heteroaryloxyalkyl, optionally substituted aryloxyaryl, optionally substituted aryloxyheteroaryl, optionally substituted C1–C6alkyl aryloxyaryl, optionally substituted C1–C6 alkyl aryloxyheteroaryl, optionally substituted alkyl aryloxy alkylamines, optionally substituted alkoxy carbonyl, optionally substituted aryloxy carbonyl, or optionally substituted heteroaryloxy carbonyl;

$R_3$ is hydrogen, C1–C6 alkyl, C3–C6 cycloalkyl, optionally substituted aryl, or optionally substituted heteroaryl;

$R_5$ is H, C1–C6 alkyl, C5–C6 cycloalkyl, or salts selected from the group Na, K, and Ca;

$R_6$ and $R_7$ are independently H, optionally substituted C1–C6 alkyl, optionally substituted aryl, optionally substituted heteroaryl, optionally substituted C1–C6 alkyl aryl, optionally substituted arylalkyl, optionally substituted heteroarylalkyl, optionally substituted C1–C6 alkyl heteroaryl, $R_6$ and $R_7$ can be together to form a 3–7 membered saturated ring system optionally having one or two heteroatoms selected from the group $N-R_1$, O, and $S=(O)_n$;

n=0–2; and $R_8$ is $N-R_6R_7$, optionally substituted C1–C6 alkoxy, hydroxy, optionally substituted —S—C1–C6 alkyl, optionally substituted —O-Aryl, optionally substituted —O—C1–C6-alkyl-aryl, optionally substituted —O-aryl alkyl(C1–C6), optionally. substituted —S-Aryl, optionally substituted —S—C1–C6-alkyl-aryl, optionally substituted —S-aryl-alkyl(C1–C6), —S— optionally substituted C1–C6 alkyl-COO—H, or —S— optionally substituted C1–C6 alkyl-COO—C1–C6 alkyl.

2. The compound according to claim 1 wherein the fused bicyclic heteroaryl group has the structural formula

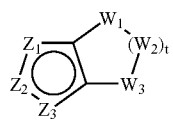

16-A wherein $Z_1$, $Z_2$, and $Z_3$ are independently $CR_2$, N, O, S or $N-R_1$ provided one of $Z_1$, $Z_2$, or $Z_3$ is carbon and is bonded to the remainder of the molecule as shown in formula I;

$W_1$, $W_2$ and $W_3$ are independently $CR_4R_4$, S, SO, $SO_2$, O, $N-R_1$, C=O; with the proviso that no S—S or O—O or S—O bond formation can occur to form the saturated ring system;

t=1 to 4;

$R_1$, $R_6$ and $R_7$ are as defined in claim 1;

$R_2$ is hydrogen, optionally substituted C1–C6 alkyl, optionally substituted C2–C6 alkenyl, optionally substituted C2–C6 alkynyl, halogen, cyano, $N-R_6R_7$, optionally substituted C1–C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, $S(O)_q$-optionally substituted C1–C6 akyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine; and $R_4$ is H, optionally substituted C1–C6 alkyl, one of $R_4$ is OH, C1–C6 alkoxy, —S—C1–C6 alkyl, $COOR_6$, $-NR_6R_7$, $-CONR_6R_7$; or $R_4R_4$ may together be =O or $R_4R_4$ together with the carbon to which they are attached may form a spiro system of five to eight members with or without the presence of heteroatoms selected N, O, $S=(O)_n$ (where n=0 to 2), $N-R_1$.

3. The compound according to claim 1 wherein the fused bicyclic heteroaryl group has the structural formula wherein

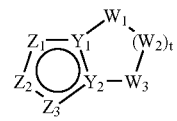

16-B $Z_1$, $Z_2$ and $Z_3$ are independently $CR_2$, N, O, S or $N-R_1$ provided one of $Z_1-Z_3$ is carbon and is bonded to the remainder of the molecule;

$W_1$, $W_2$ and $W_3$ are independently $CR_4R_4$, S, SO, $SO_2$, O, or $N-R_1$;

t=1 to 4;

$Y_1$ and $Y_2$ are independently N or C; with the proviso that if the aromatic ring portion of the bicyclic heteroaryl group is imidazole, the nonaromatic ring portion may not contain a S adjacent to the bridgehead carbon;

$R_1$, $R_6$ and $R_7$ are as defined in claim 1;

$R_4$ is H, optionally substituted C1–C6 alkyl, one of $R_4$ is OH, C1–C6 alkoxy, —S—C1–C6 alkyl, $COOR_6$, $-NR_6R_7$, $-CONR_6R_7$; or $R_4R_4$ may together be =O or $R_4R_4$ together with the carbon to which they are attached may form a spiro system of five to eight members with or without the presence of heteroatoms selected N, O, $S=(O)_n$ (where n=0 to 2), $N-R_1$; and $R_2$ is hydrogen, optionally substituted C1–C6 alkyl, optionally substituted C2–C6 alkenyl, optionally substituted C2–C6 alkynyl, halogen, cyano, $N-R_6R_7$, optionally substituted C1–C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, $S(O)_q$-optionally substituted C1–C6 akyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6 alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine.

4. The compound according to claim 1 wherein the fused bicyclic heteroaryl group is

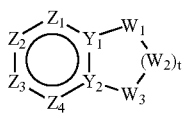

16-C wherein $Z_1$, $Z_2$, $Z_3$ and $Z_4$ are independently $CR_2$ or N provided one of $Z_1$–$Z_4$ is bonded to the remainder of the molecule;

$W_1$, $W_2$ and $W_3$ are independently $CR_4R_4$, S, SO, $SO_2$, O, or N—$R_1$; with the proviso that no S—S or O—O or S—O bond formation can occur to form the saturated ring system;

t=1 to 4;

$Y_1$ and $Y_2$ are independently C or N; $R_4$ is H, optionally substituted C1–C6 alkyl, one of $R_4$ is OH, C1–C6 alkoxy, —S—C1–C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, S=(O)$_n$ (where n=0 to 2), N—$R_1$;

$R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, S(O)$_q$-optionally substituted C1–C6 akyl, S(O)$_q$— optionally substituted aryl where q is 0, 1 or 2, $CONR_6R_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, $SO_2NR_6R7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine; and $R_1$, $R_6$, and $R_7$ are as defined in claim 1.

5. The compound according to claim 1 wherein the fused tricyclic heteroaryl group has the formula

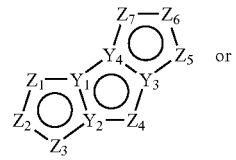

1-A

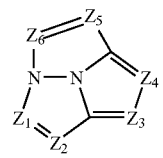

1-B wherein $Z_1$, $Z_2$, $Z_3$, $Z_4$, $Z_5$, $Z_6$ and $Z_7$ are independently $CR_2$, N, O, S or N—$R_1$ provided one of $Z_1$–$Z_7$ is a carbon atom to which the remainder of the molecule is attached; $R_1$, $R_6$ and $R_7$ are as defined in claim 1;

$R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, S(O)$_q$-optionally substituted C1–C6 akyl, S(O)$_q$— optionally substituted aryl where q is 0, 1 or 2, $CONR_6R_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, $SO_2NR_6R7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6 alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine; and $Y_1$, $Y_2$, $Y_3$ and $Y_4$ may independently be C or N.

6. The compound according to claim 1 wherein the tricyclic heteroaryl group is

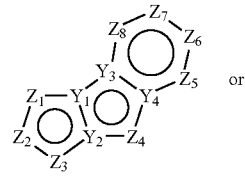

2-A

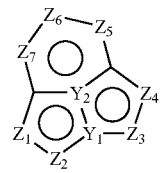

2-B wherein $Z_1$, $Z_2$, $Z_3$, $Z_4$, $Z_5$, $Z_6$, $Z_7$ and $Z_8$ are independently $CR_2$, N, O, S or N—$R_1$ provided one of the $Z_1$–$Z_8$ is a carbon atom to which the remainder of the molecule is attached;

$R_1$, $R_6$ and $R_7$ are as defined in claim 1;

$R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, S(O)$_q$-optionally substituted C1–C6 akyl, S(O)$_q$— optionally substituted aryl where q is 0, 1 or CONR$_6$R$_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6 alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine; and $Y_1$, $Y_2$, $Y_3$ and $Y_4$ are independently C or N.

7. The compound according to claim 1 wherein the tricyclic heteroaryl group is

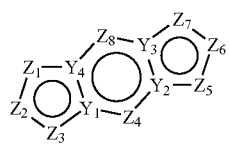

3-A

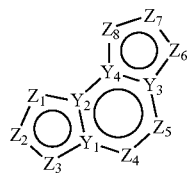

3-B wherein $Z_1$, $Z_2$, $Z_3$, $Z_4$, $Z_5$, $Z_6$, $Z_7$ and $Z_8$ are independently $CR_2$, N, O, S or N—$R_1$ provided one of $Z_1$–$Z_8$ is a carbon atom to which the remainder of the molecule is attached;

$R_1$, $R_6$ and $R_7$ are as defined in claim 1;

$R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, S(O)$_q$-optionally substituted C1–C6 akyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine; and $Y_1$, $Y_2$, $Y_3$ and $Y_4$ may be C or N.

8. The compound according to claim 1 wherein the tricyclic heteroaryl group is

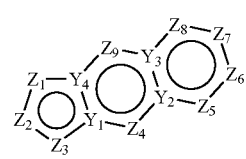

4-A

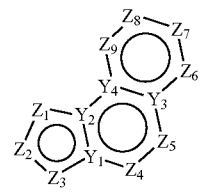

4-B

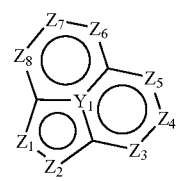

4-C wherein $Z_1$, $Z_2$, $Z_3$, $Z_4$, $Z_5$, $Z_6$, $Z_7$, $Z_8$ and $Z_9$ are independently $CR_2$, N, O, S or N—$R_1$ provided one of the $Z_1$–$Z_9$ is a carbon atom to which the remainder of the molecule is attached;

$R_1$, $R_6$ and $R_7$ are as defined in claim 1;

$R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, S(O)$_q$-optionally substituted C1–C6 akyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine; and Y$_1$, Y$_2$, Y$_3$ and Y$_4$ are independently C or N.

9. The compound according to claim 1 wherein the tricyclic heteroaryl group is

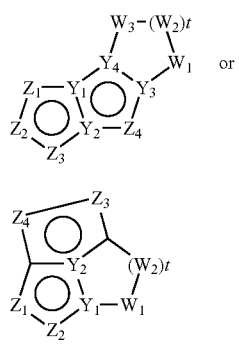

wherein Z$_1$, Z$_2$, Z$_3$ and Z$_4$ are independently CR$_2$, N, O, S or N—R$_1$ provided one of Z$_1$–Z$_4$ is a carbon atom to which the remainder of the molecule is attached;
Y$_1$, Y$_2$, Y$_3$ and Y$_4$ are independently C or N;
W$_1$, W$_2$ and W$_3$ are independently CR$_4$R$_4$, S(O)$_r$ (r=0–2), O, or N—R$_1$ with the proviso that no S—S, S—O or O—O bond formation can occur to form a saturated ring;
R$_1$, R$_6$ and R$_7$ are as defined in claim 1;
R$_2$ is hydrogen, optionally substituted C1–C6 alkyl, optionally substituted C2–C6 alkenyl, optionally substituted C2–C6 alkynyl, halogen, cyano, N—R$_6$R$_7$, optionally substituted C1–C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C3–C6 alkoxy, alkylenedioxy, optionally substituted aryloxy-C1–C6 alkyl amine, C1–C6 perfluoro alkyl, S(O)$_q$optionally substituted C1–C6 akyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine;

R$_4$ is H, optionally substituted C1–C6 alkyl, OH (provided both R$_4$ are not OH), C1–C6 alkoxy, —S—C1–C6 alkyl, COOR$_6$, —NR$_6$R$_7$, —CONR$_6$R$_7$; or R$_4$R$_4$ may together be =O or R$_4$R$_4$ together with the carbon to which they are attached may form a spiro system of five to eight members with or without the presence of heteroatoms selected N, O, S(O)$_n$ (where n=0 to 2), N—R$_1$;
and t=1 to 3.

10. The compound according to claim 1 wherein the tricyclic heteroaryl group is

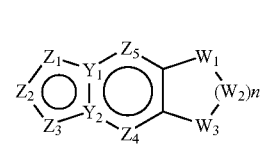

wherein Z$_1$, Z$_2$, Z$_3$, Z$_4$ and Z$_5$ are independently CR$_2$, N, O, S or N—R$_1$ provided one of Z$_1$–Z$_5$ is a carbon atom to which the remainder of the molecule is attached;
Y$_1$, and Y$_2$ are independently C or N;
W$_1$, W$_2$ and W$_3$ are independently CR$_4$R$_4$, S(O)$_r$ (r=0–2), O, or N—R$_1$ with the proviso that no S—S, S—O or O—O bond formation can occur to form a saturated ring;
R$_1$, R$_6$, and R$_7$ are as defined in claim 1;
R$_2$ is hydrogen, optionally substituted C1–C6 alkyl, optionally substituted C2–C6 alkenyl, optionally substituted C2–C6 alkynyl, halogen, cyano, N—R$_6$R$_7$, optionally substituted C1–C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, S(O)$_q$-optionally substituted C1–C6 akyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine;

R$_4$ is H, optionally substituted C1–C6 alkyl, OH (provided both R$_4$ are not OH), C1–C6 alkoxy, —S—C1–C6 alkyl, COOR$_6$, —NR$_6$R$_7$; —CONR$_6$R$_7$; or R$_4$R$_4$ may together be =O or R$_4$R$_4$ together with the carbon to which they are attached may form a spiro system of five to eight members with or without the presence of heteroatoms selected N, O, S(O)$_n$ (where n=0 to 2), N—R$_1$;

and t=1 to 3.

11. The compound according to claim 1 wherein the tricyclic heteroaryl group is

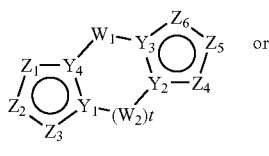

7-A or

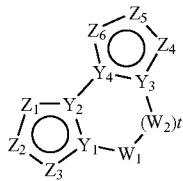

7-B wherein Z$_1$, Z$_2$, Z$_3$, Z$_4$, Z$_5$ and Z$_6$ are independently CR$_2$, N, O, S, and N—R$_1$; provided one of Z$_1$–Z$_6$ is a carbon atom to which the remainder of the molecule is attached; Y$_1$, Y$_2$, Y$_3$ and Y$_4$ are independently C or N;

W$_1$ and W$_2$ are independently CR$_4$R$_4$, S(O)$_r$ (r=0–2), O, N—R$_1$ with the proviso that no S—S, S—O or O—O bond formation can occur to form a saturated ring;

R$_1$, R$_6$, and R$_7$ are as defined in claim 1;

R$_2$ is hydrogen, optionally substituted C1–C6 alkyl, optionally substituted C2–C6 alkenyl, optionally substituted C2–C6 alkynyl, halogen, cyano, N—R$_6$R$_7$, optionally substituted C1–C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, S(O)$_q$-optionally substituted C1–C6 akyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, SO$_2$NR$_6$R$_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine;

R$_4$ is H, optionally substituted C1–C6 alkyl, OH (provided both R4 are not OH), C1–C6 alkoxy, —S—C1–C6 alkyl, COOR$_6$, —NR$_6$R$_7$; —CONR$_6$R$_7$; or R$_4$R$_4$ may together be =O or R$_4$R$_4$ together with the carbon to which they are attached may form a spiro system of five to eight members with or without the presence of heteroatoms selected N, O, S(O)$_n$ (where n=0 to 2), N—R$_1$;

and t=1 to 3.

12. The compound according to claim 1 wherein the tricyclic heteroaryl group is

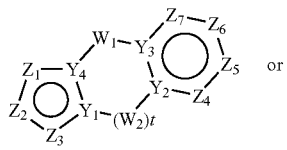

8-A or

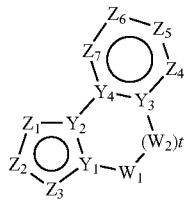

8-B wherein Z$_1$, Z$_2$, Z$_3$, Z$_4$, Z$_5$, Z$_6$ and Z$_7$ are independently CR$_2$, N, O, S or N—R$_1$ provide one of the Z$_1$–Z$_7$ is a carbon atom to which the remainder of the molecule is attached;

Y$_1$, Y$_2$, Y$_3$ and Y$_4$ are independently C or N;

W$_1$ and W$_2$ are independently CR$_4$R$_4$, S(O)$_r$ (r=0–2), O, or N—R$_1$ with the proviso that no S—S, S—O or O—O bond formation can occur to form a saturated ring;

R$_1$, R$_6$, and R$_7$ are as defined in claim 1;

R$_2$ is hydrogen, optionally substituted C1–C6 alkyl, optionally substituted C2–C6 alkenyl, optionally substituted C2–C6 alkynyl, halogen, cyano, N—R$_6$R$_7$, optionally substituted C1–C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, S(O)$_q$-optionally substituted C1–C6 akyl, S(O)$_q$— optionally substituted aryl where q is 0, 1 or 2, CONR$_6$R$_7$, guanidino or cyclic guanidino, optionally substituted alkylaryl, optionally substituted arylalkyl, optionally substituted C1–C6 alkylheteroaryl, optionally substituted heteroaryl-C3–C6 alkyl, optionally substituted C1–C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1–C6 alkyl, OH (provided both $R_4$ are not OH), C1–C6 alkoxy, —S—C1–C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, $S(O)_n$ (where n=0 to 2), N—$R_1$;

and t=0–3.

13. The compound according to claim 1 wherein the tricyclic heteroaryl group is

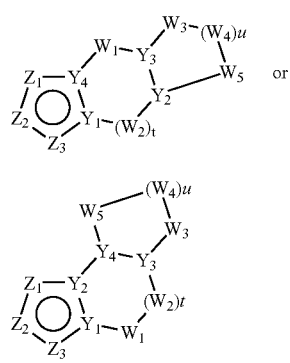

wherein $Z_1$, $Z_2$ and $Z_3$ are independently $CR_2$, N, O, S or N—$R_1$ provided one of $Z_1$–$Z_3$ is a carbon atom to which the remainder of the molecule is attached;

$Y_1$ and $Y_4$ are independently C or N;

$Y_2$ and $Y_3$ are independently CH or N;

$W_1$, $W_2$, $W_3$, $W_4$ and $W_5$ are independently $CR_4R_4$, $S(O)_r$ (r=0–2), O, or N—$R_1$ proviso that no S—S, S—O or O—O bond formation can occur to form a saturated ring;

$R_1$, $R_6$, and $R_7$ are as defined in claim 1;

$R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, $S(O)_n$-optionally substituted C1–C6 akyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1–C6 alkyiheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1–C6 alkyl, OH (provided both $R_4$ are not OH), C1–C6 alkoxy, —S—C1–C6 alkyl, $COOR_6$, —$NR_6R_7$, —$CONR_6R_7$; or $R_4R_4$ may together be =O or $R_4R_4$together with the carbon to which they are attached may form a spiro system of five to eight members with or without the presence of heteroatoms selected N, O, $S(O)_n$ (where n=0 to 2), N—$R_1$;

t=0 to 2; and u=1 to 3.

14. The compound according to claim 1 wherein the tricyclic heteroaryl group is

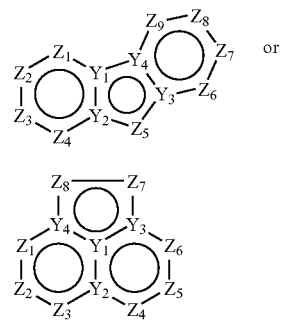

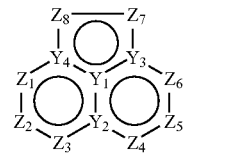

wherein $Z_1$, $Z_2$, $Z_3$, $Z_4$, $Z_5$, $Z_6$, $Z_7$, $Z_8$ and $Z_9$ are independently $CR_2$, N, O, S or N—$R_1$ provided one of the $Z_1$–$Z_9$ is a carbon atom to which the remainder of the molecule is attached; $R_1$, $R_6$, and $R_7$ are as defined in claim 1; $R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, $S(O)_q$-optionally substituted C1–C6 akyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine;

and $Y_1$, $Y_2$, $Y_3$ and $Y_4$ are independently C or N.

15. The compound according to claim 1 wherein the tricyclic heteroaryl group is

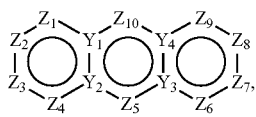

11-A

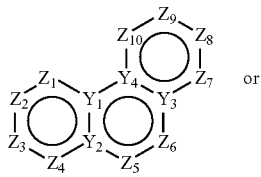

11-B or

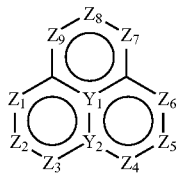

11-C wherein $Z_1$, $Z_2$, $Z_3$, $Z_4$, $Z_5$, $Z_6$, $Z_7$, $Z_8$, $Z_9$ and $Z_{10}$ are independently $CR_2$, N, O, S or N—$R_1$ provided one of $Z_1$–$Z_{10}$ is a carbon atom to which the remainder of the molecule is attached;

$R_1$, $R_6$, and $R_7$ are as defined in claim 1;

$R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, COOR$_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, S(O)$_q$-optionally substituted C1–C6 akyl, S(O)$_q$— optionally substituted aryl where q is 0, 1 or 2, CONR$_6R_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, SO$_2$NR$_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine; and $Y_1$, $Y_2$, $Y_3$ and $Y_4$ are independently C or N.

16. The compound according to claim 1 wherein the tricyclic heteroaryl group is

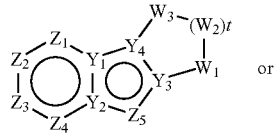

12-A or

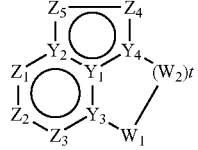

12-B wherein $Z_1$, $Z_2$, $Z_3$, $Z_4$ and $Z_5$ are independently $CR_2$, N, O, S or N—$R_1$ provided that one of $Z_1$–$Z_5$ is a carbon atom to which the remainder of the molecule is attached;

$Y_1$, $Y_2$, $Y_3$ and $Y_4$ are independently C or N;

$W_1$, $W_2$, $W_3$ are independently $CR_4R_4$ O, N—$R_1$, or S=(O)$_r$ (r=0–2) with the proviso that no S—S, S—O or O—O bond formation can occur to form a saturated ring;

$R_1$, $R_6$, and $R_7$ are as defined in claim 1;

$R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, COOR6, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, S(O)$_n$-optionally substituted C1–C6 akyl, S(O)$_q$— optionally substituted aryl where q is 0, 1 or 2, CONR$_6R_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, SO$_2$NR$_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1–C6 alkyl, OH (provided both $R_4$ are not OH), C1–C6 alkoxy, —S—C1–C6 alkyl, COOR$_6$, —NR$_6R_7$; —CONR$_6R_7$; or $R_4R_4$ may together be =O or $R_4R_4$together with the carbon to which they are attached may form a spiro system of five to eight members with or without the presence of heteroatoms selected N, O, S(O)$_n$ (where n=0 to 2), N—$R_1$;

and t=1–4.

17. The compound according to claim 1 wherein the tricyclic heteroaryl group is

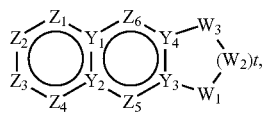
13-A

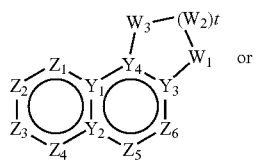
13-B

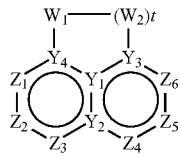
13-C wherein $Z_1$, $Z_2$ $Z_3$, $Z_4$, $Z_5$ and $Z_6$ are independently $CR_2$, N, O, S or N—$R_1$ provided one of $Z_1$–$Z_6$ is a carbon atom to which the remainder of the molecule is attached;

$Y_1$, $Y_2$, $Y_3$ and $Y_4$ are independently C or N;

$W_1$, $W_2$ and $W_3$ are independently $CR_4R_4$, $S(O)_r$ (r=0–2), O, or N—$R_1$ with the proviso that no S—S, S—O or O—O bond formation can occur to form a saturated ring;

$R_1$, $R_6$, and $R_7$ are as defined in claim 1;

$R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C3–C6 alkoxy, alkylenedioxy, optionally substituted aryloxy-C1–C6 alkyl amine, C1–C6 perfluoro alkyl, $S(O)_q$-optionally substituted C1–C6 akyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1–C6 alkyl, OH (provided both $R_4$ are not OH), C1–C6 alkoxy, —S—C1–C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, $S(O)_n$ (where n=0 to 2), N—$R_1$;

and t=1 to 3.

18. The compound according to claim 1 wherein the tricyclic heteroaryl group is

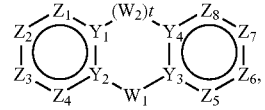
14-A

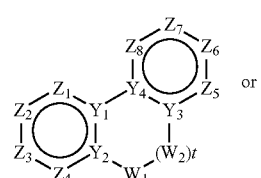
14-B

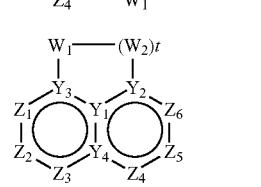
14-C wherein $Z_1$, $Z_2$, $Z_3$, $Z_4$, $Z_5$, $Z_6$, $Z_7$ and $Z_8$ are independently $CR_2$, N, O, S or N—$R_1$ provided one of $Z_1$–$Z_8$ is a carbon atom to which the remainder of the molecule is attached;

$Y_1$, $Y_2$, $Y_3$ and $Y_4$ are independently C or N;

$W_1$, and $W_2$ are independently $CR_4R_4$, $S(O)_r$ (r=0–2), O, or N—$R_1$ with the proviso that no S—S, S—O or O—O bond formation can occur to form a saturated ring;

$R_1$, $R_6$, and $R_7$ are as defined in claim 1;

$R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, $S(O)_q$-optionally substituted C1–C6 akyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1–C6 alkyl, OH (provided both $R_4$ are not OH), C1–C6 alkoxy, —S—C1–C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, $S(O)_n$ (where n=0 to 2), N—$R_1$;

and t=1 to 2.

19. The compound according to claim 1 wherein the tricyclic heteroaryl group is

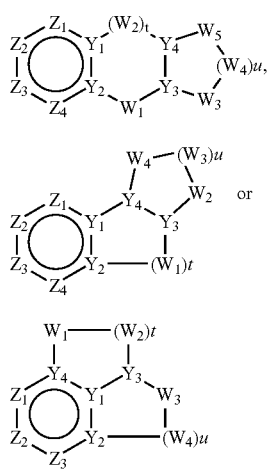

wherein $Z_1$, $Z_2$, $Z_3$ and 4 are independently $CR_2$, N, O, S or N—$R_1$ provided one of $Z_1$–$Z_4$ is a carbon atom to which the remainder of the molecule is attached;

$Y_1$, $Y_2$, $Y_3$ and $Y_4$ are independently C or N;

$W_1$, $W_2$, $W_3$, $W_4$ and $W_5$ are independently $CR_4R_4$, $S(O)_r$ (r=0–2), O, or N—$R_1$ with the proviso that no S—S, S—O or O—O bond formation can occur to form a saturated ring;

$R_1$, $R_6$, and $R_7$ are as defined in claim 1;

$R_2$ is hydrogen, optionally substituted C1–C6 alkyl, optionally substituted C2–C6 alkenyl, optionally substituted C2–C6 alkynyl, halogen, cyano, N—$R_6R_7$, optionally substituted C1–C6 alkoxy, hydroxy; optionally substituted aryl, optionally substituted heteroaryl, $COOR_6$, optionally substituted alkylaryloxyalkylamines, optionally substituted aryloxy, optionally substituted heteroaryloxy, optionally substituted C3–C6 alkenyloxy, optionally substituted C3–C6 alkynyloxy, C1–C6 alkylamino-C1–C6 alkoxy, alkylenedioxy, optionally substituted aryloxy-C1–C6 alkyl amine, C1–C6 perfluoro alkyl, $S(O)_q$-optionally substituted C1–C6 akyl, $S(O)_q$— optionally substituted aryl where q is 0, 1 or 2, $CONR_6R_7$, guanidino or cyclic guanidino, optionally substituted alkylaryl, optionally substituted arylalkyl, optionally substituted C1–C6 alkylheteroaryl, optionally substituted heteroaryl-C1–C6 alkyl, optionally substituted C1–C6 alkyl mono or bicyclic saturated heterocycles, optionally substituted arylalkenyl of 8 to 16 carbon atoms, $SO_2NR_6R_7$, optionally substituted arylalkyloxyalkyl, optionally substituted aryloxyalkyl, optionally substituted heteroaryloxyalkyl, optionally substituted aryloxyaryl, optionally substituted aryloxyheteroaryl, optionally substituted heteroaryloxyaryl, optionally substituted C1–C6alkyl aryloxyaryl, optionally substituted C1–C6 alkylaryloxyheteroaryl, optionally substituted aryloxyalkyl, optionally substituted heteroaryloxyalkyl, or optionally substituted alkylaryloxyalkylamine;

$R_4$ is H, optionally substituted C1–C6 alkyl, OH (provided both $R_4$ are not OH), C1–C6 alkoxy, —S—C1–C6 alkyl, $COOR_6$, —$NR_6R_7$, —$CONR_6R_7$; or $R_4R_4$ may together be =O or $R_4R_4$ together with the carbon to which they are attached may form a spiro system of five to eight members with or without the presence of heteroatoms selected N, O, $S(O)_n$ (where n=0 to 2), N—$R_1$;

t=1 to 3; and u=1 to 3.

20. A pharmaceutical composition comprising an effective amount of a compound of claim 1 and a pharmaceutically acceptable carrier.

21. A method of treating a bacterial infection which comprises providing an effective amount of a compound according to claim 1 or a composition according to claim 20.

* * * * *